United States Patent
Brenneman et al.

(10) Patent No.: US 10,004,722 B2
(45) Date of Patent: Jun. 26, 2018

(54) METHOD FOR TREATING HEPATIC ENCEPHALOPATHY OR A DISEASE ASSOCIATED WITH FREE RADICAL MEDIATE STRESS AND OXIDATIVE STRESS WITH NOVEL FUNCTIONALIZED 1,3-BENZENE DIOLS

(71) Applicant: KANNALIFE SCIENCES, INC., Huntington, NY (US)

(72) Inventors: Douglas E. Brenneman, North Wales, PA (US); William Alvin Kinney, Newtown, PA (US); Mark McDonnell, Lansdale, PA (US); Dean Petkanas, Huntington, NY (US)

(73) Assignee: KANNALIFE SCIENCES, INC., Huntington, NY (US)

( * ) Notice: Subject to any disclaimer, the term of this patent is extended or adjusted under 35 U.S.C. 154(b) by 0 days. days.

(21) Appl. No.: 15/436,956

(22) Filed: Feb. 20, 2017

(65) Prior Publication Data
US 2017/0157097 A1    Jun. 8, 2017

Related U.S. Application Data

(62) Division of application No. 14/781,081, filed as application No. PCT/US2015/010827 on Jan. 9, 2015, now Pat. No. 9,611,213.

(60) Provisional application No. 61/926,869, filed on Jan. 13, 2014.

(51) Int. Cl.
*A61K 31/4192* (2006.01)
*A61K 31/397* (2006.01)
*C07D 249/04* (2006.01)
*C07D 205/06* (2006.01)
*C07B 59/00* (2006.01)
*C07D 205/04* (2006.01)

(52) U.S. Cl.
CPC ........ *A61K 31/4192* (2013.01); *A61K 31/397* (2013.01); *C07B 59/002* (2013.01); *C07B 2200/05* (2013.01); *C07D 205/04* (2013.01); *C07D 205/06* (2013.01); *C07D 249/04* (2013.01)

(58) Field of Classification Search
CPC . C07B 2200/05; C07B 59/002; C07D 205/04; C07D 205/06; C07D 249/04; A61K 31/4192; A61K 31/397
See application file for complete search history.

(56) References Cited

U.S. PATENT DOCUMENTS

| | | | |
|---|---|---|---|
| 2010/0022631 | A1 | 1/2010 | Berry et al. |
| 2012/0172339 | A1 | 7/2012 | Makriyannis et al. |

OTHER PUBLICATIONS

Arias et al., "Mapping Metabolic Brain Activity in Three Models of Hepatic Encephalopathy," International Journal of Hypertension, vol. 2013, Article ID 390872, 7 pages, 2013. doi:10.1155/2013/390872.

(Continued)

*Primary Examiner* — Savitha M Rao
(74) *Attorney, Agent, or Firm* — Caesar Rivise, PC

(57) ABSTRACT

Pharmaceutical compositions of the invention include novel functionalized 1,3-benzenediols having a disease-modifying action in the treatment of hepatic encephalopathy and related conditions. Pharmaceutical compositions of the invention further include novel neuroprotective agents.

6 Claims, 1 Drawing Sheet

Mean plasma concentration-time profiles of KLS-13019 after single IV and PO administrations in CD1 mice (N=3/time point)

(56) References Cited

OTHER PUBLICATIONS

Bailey et al., "Acute and Chronic Ethanol Increases Reactive Oxygen Species Generation and Decreases Viability in Fresh, Isolated Rat Hepatocytes", Heptatology, vol. 28, No. 5, pp. 1318-1326 (1998).

Bengzon et al., "Neuronal apoptosis after brief and prolonged seizures", Progress in Brain Research, vol. 135, pp. 111-119 (2002).

Brewer, "Serum-free B27/neurobasal medium supports differentiated growth of neurons from the striatum, substantia nigra, septum, cerebral cortex, cerebellum, and dentate gyrus." Journal of neuroscience research 42.5 (1995): 674-683.

Cavus et al., "Decreased hippocampal volume on MRI is associated with increased extracellular glutamate in epilepsy patients", Epilepsia, vol. 49, No. 8, pp. 1358-1366 (2008).

Chen et al., "Cannabinoids protect cells from oxidative cell death: a receptor-independent mechanism." Journal of Pharmacology and Experimental Therapeutics 293.3 (2000): pp. 807-812.

Consroe et al., "Cannabidiol—Antiepileptic Drug Comparisons and Interactions in Experimentally Induced Seizure in Rats", The Journal of Pharmacology and Experimental Therapeutics, vol. 201, No. 1 (1977).

Cordoba, "New assessment of hepatic encephalopathy", Journal of Hepatology, vol. 54, pp. 1030-1040 (2011).

Ferriero, "Protecting Neurons", Epilepsia, vol. 46, Supp. 7, pp. 45-51 (2005).

Hamelink et al., "Comparison of Cannabidiol, Antioxidants, and Diuretics in Reversing Binge Ethanol-Induced Neurotoxicity", The Journal of Pharmacology and Experimental Therapeutics, vol. 314, No. 2, pp. 780-788 (2005).

Jarrett et al., "Mitochondrial DNA damage and impaired base excision repair", Neurobiol Dis., vol. 30, No. 1, pp. 130-138 (2008).

Nagayama et al., "Cannabinoids and Neuroprotection in Global and Focal Cerebral Ischemia and in Neuronal Cultures", The Journal of Neuroscience, vol. 19, No. 8, pp. 2987-2995 (1999).

Ong et al., "Correlation between Ammonia Levels and the Severity of Hepatic Encephalopathy", The American Journal of Medicine, vol. 114, pp. 188-193 (2003).

Petroski et al., Selective labeling of embryonic neurons cultured on astrocyte monolayers with 5(6)-carboxyfluorescein diacetate (CFDA), Journal of Neuroscience Methods, vol. 52, pp. 23-32 (1994).

Randall et al., Glutamate-induced Calcium Transient Triggers Delayed Calcium Overload and Neurotoxicity in Rat Hippocampal Neurons, The Journal of Neuroscience, vol. 12, No. 5, pp. 1882-1895 (1992).

Sarafian et al, "Synergistic cytotoxicity of $\Delta$9-tetrahydrocannabinol and butylated hydroxyanisole", Toxicology Letters, vol. 133, pp. 171-179 (2002).

Swinyard, "Laboratory Evaluation of Antiepilpetic Drugs—Review of Laboratory Methods", Epilepsia, vol. 10, pp. 107-119 (1969).

Van Den Pol et al., "Glutamate Hyperexcitability and Seizure-Like Activity Throughout the Brain and Spinal Cord Upon Relief from Chronic Glutamate Receptor Blockade in Culture", Neuroscience, vol. 74, No. 3, pp. 653-674 (1996).

Waldbaum et al., "Mitochondria, oxidative stress, and temporal lobe epilepsy", Epilepsy Research, vol. 88, pp. 23-45 (2010).

Warren, "The Differential Toxicity of Ammonium Salts", J Clin Invest., vol. 37, No. 4, pp. 497-501 (1958).

Wu et al., "Mitochondrial DNA Mutation-Elicited Oxidative Stress, Oxidative Damage, and Altered Gene Expression in Cultured Cells of Patients with MERRF Syndrome", Mol Neurobiol, vol. 41, pp. 256-266 (2010).

International Search Report for PCT/US2015/010827 dated Jun. 4, 2015.

Supplementary European Search Report from EP 15734870 dated Sep. 8, 2016.

Mean plasma concentration-time profiles of KLS-13019 after single IV and PO administrations in CD1 mice (N=3/time point)

Mean plasma concentration-time profiles of KLS-13019 after single 10 mg.kg PO administrations in CD1 mice (N=3/time point)

METHOD FOR TREATING HEPATIC ENCEPHALOPATHY OR A DISEASE ASSOCIATED WITH FREE RADICAL MEDIATE STRESS AND OXIDATIVE STRESS WITH NOVEL FUNCTIONALIZED 1,3-BENZENE DIOLS

CROSS-REFERENCE TO RELATED APPLICATIONS

This application is a division of U.S. application Ser. No. 14/781,081, filed Sep. 29, 2015, which is a 371 of PCT/US2015/010827, filed Jan. 9, 2015, which claims the benefit of U.S. Application Ser. No. 61/926,869, filed Jan. 13, 2014, all of which are incorporated herein by reference in their entireties.

FIELD OF INVENTION

The present invention describes novel functionalized 1,3-benzenediols and methods useful for the treatment of hepatic encephalopathy and related conditions. The present invention further describes a novel chemotype useful for the treatment of diseases associated with hepatic encephalopathy. The present invention further describes a novel chemotype useful as neuroprotective agents.

BACKGROUND OF THE INVENTION

Hepatic encephalopathy (HE) is a neuropsychiatric disorder that includes learning deficits and impairment of long-term memory. If left unchecked, HE can progress to hepatic coma (also referred to as coma hepaticum) and ultimately death (Cordoba, 2011). The pathogenesis of HE includes damage to the prelimbic cortex, striatum and the hippocampus (Aria et al., 2013). Hepatic encephalopathy is caused by accumulation of toxic substances in the bloodstream that are normally removed by the liver. It has been previously demonstrated that impaired liver function and liver disease is associated with the production of free radical and oxidative stress (Bailey and Cunningham, 1998). The accumulation of these free radicals and oxidative stress contribute to cognitive impairment, learning deficits, memory impairment, as well as damage and death of neuronal tissue.

An emerging concept is that neuroprotection by prevention of free radical mediated stress and oxidative stress will prevent the neural damage associated with hepatic encephalopathy and prevent cognitive impairment, learning deficits, memory impairment, as well as damage and death of neuronal tissue associated with HE. Compounds capable of acting as neuroprotective agents by blocking the damage caused by free radicals and oxidative stress will prevent the neural damage associated with hepatic encephalopathy and prevent cognitive impairment, learning deficits, memory impairment, as well as damage and death of neuronal tissue associated with HE. Free radical mediated stress and oxidative stress is also known to contribute to additional pathological conditions including, but not limited to epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS). Compounds capable of acting as neuroprotective agents will be useful for the treatment of epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS).

There is a long felt need for neuroprotective agents that are both disease-modifying and effective in treating patients that are experiencing HE. The present invention addresses the need to prevent free radical mediated stress and oxidative stress, as well as to prevent the neural damage associated with HE. The present invention further addresses the need to prevent cognitive impairment, learning deficits, memory impairment, as well as damage and death of neuronal tissue associated with HE. The present invention also addresses the long felt need for new treatments for and means of preventing diseases with free radical mediate stress and oxidative stress in their etiology, including, for example, epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS).

SUMMARY OF THE INVENTION

The present invention is directed toward novel functionalized 1,3-benzenediols, compounds of formula (I),

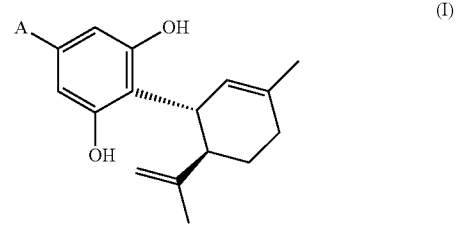

Including hydrates, solvates, pharmaceutically acceptable salts, prodrugs and complexes thereof, wherein:

A is selected from the group consisting of

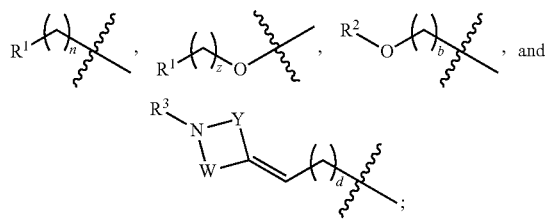

, and $z$ is 0, 1, or 2;

When A is

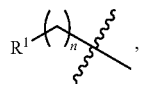

R¹ is selected from the group consisting of
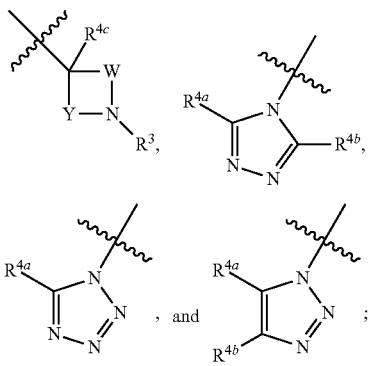
, and ;
When A is
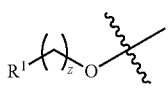
and z is 0, R¹ is
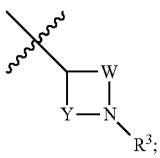
When A is
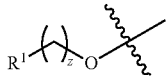
and z is 1, R¹ is
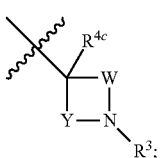
When A is
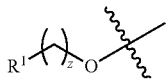
and z is 2, R¹ is selected from the group consisting of
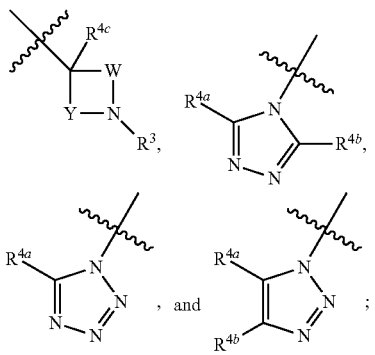
, and ;
When R¹ is
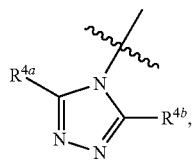
n is not 0;
When R¹ is
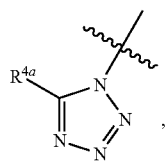
n is not 0;
When R¹ is
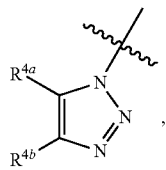
n is not 0;
R² is
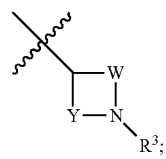
W is (CH$_2$)$_m$;
m is 1 or 2;
Y is (CH$_2$)$_q$;
q is 1 or 2;
n is 0, 1, 2, or 3;

b is 0, 1, 2, or 3;

d is 0, 1, 2, or 3;

$R^3$ is selected from the group consisting of $COR^5$, $CO_2R^6$, $CONR^{7a}R^{7b}$, $SO_2NR^{7a}R^{7b}$, $SO_2R^8$, and optionally substituted heteroaryl;

$R^{4a}$ and $R^{4b}$ are each independently selected from the group consisting of hydrogen and $C_{1-6}$ alkyl;

$R^{4c}$ is selected from the group consisting of hydrogen and OH;

$R^5$ is selected from the group consisting of hydrogen, $C_{1-6}$ alkyl, optional substituted heteroaryl, —$C(R^{9a}R^{9b})NR^{7a}R^{7b}$, and —$C(R^{9a}R^{9b})OR^{10}$;

$R^5$ is also selected from optional substituted $C_{1-6}$ alkyl;

$R^6$ is $C_{1-6}$ alkyl;

$R^6$ is also selected from optional substituted $C_{1-6}$ alkyl;

$R^{7a}$ and $R^{7b}$ are each independently selected from the group consisting of hydrogen and $C_{1-6}$ alkyl;

$R^{7a}$ and $R^{7b}$ are also each independently selected from optional substituted $C_{1-6}$ alkyl;

$R^8$ is selected from the group consisting of hydrogen, $C_{1-6}$ alkyl and optional substituted heteroaryl;

$R^8$ is also selected from optional substituted $C_{1-6}$ alkyl;

$R^{9a}$ and $R^{9b}$ are each independently selected from the group consisting of hydrogen, $C_{1-6}$ alkyl, $C_{3-7}$ branched alkyl, $CH_2OH$, $CH(OH)CH_3$, $CH_2Ph$, $CH_2(4\text{-OH-Ph})$, $(CH_2)_4NH_2$, $(CH_2)_3NHC(NH_2)NH$, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$.

$R^{10}$ is selected from the group consisting of hydrogen and $C_{1-6}$ alkyl.

The compounds of the present invention further include enantiomers of compounds of the formula (I).

The compounds of the present invention further include compounds of the formula (I) that are isotopically labeled with 1 to 10 deuterium atoms.

The compounds of the present invention include compounds having formula (II):

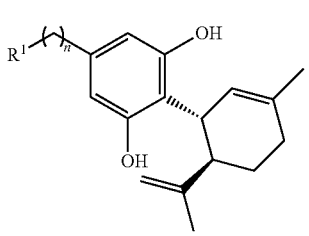

(II)

including hydrates, solvates, pharmaceutically acceptable salts, and complexes thereof.

The compounds of the present invention further include enantiomers of compounds of the formula (II).

The compounds of the present invention further include compounds of the formula (II) that are isotopically labeled with 1 to 10 deuterium atoms.

The compounds of the present invention include compounds having formula (III):

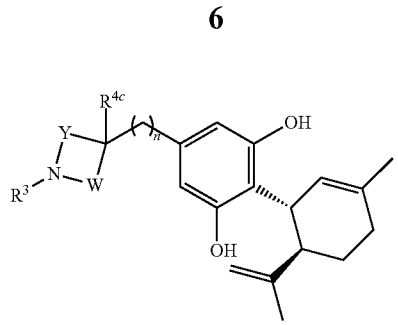

(III)

including hydrates, solvates, pharmaceutically acceptable salts, and complexes thereof.

The compounds of the present invention further include enantiomers of compounds of the formula (III).

The compounds of the present invention further include compounds of the formula (III) that are isotopically labeled with 1 to 10 deuterium atoms.

The compounds of the present invention include compounds having formula (IV):

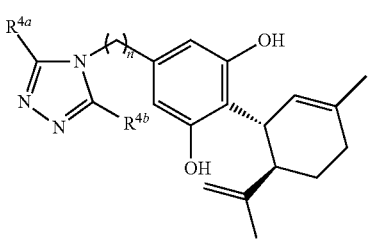

(IV)

including hydrates, solvates, pharmaceutically acceptable salts, and complexes thereof.

The compounds of the present invention further include enantiomers of compounds of the formula (IV).

The compounds of the present invention further include compounds of the formula (IV) that are isotopically labeled with 1 to 10 deuterium atoms.

The compounds of the present invention include compounds having formula (V):

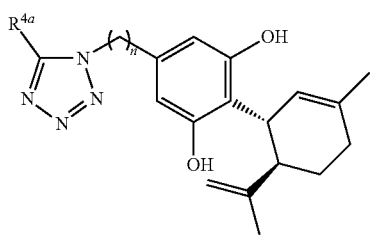

(V)

including hydrates, solvates, pharmaceutically acceptable salts, and complexes thereof.

The compounds of the present invention further include enantiomers of compounds of the formula (V).

The compounds of the present invention further include compounds of the formula (V) that are isotopically labeled with 1 to 10 deuterium atoms.

The compounds of the present invention include compounds having formula (VI):

(VI)

including hydrates, solvates, pharmaceutically acceptable salts, and complexes thereof.

The compounds of the present invention further include compounds of the formula (VI) that are isotopically labeled with 1 to 10 deuterium atoms.

The compounds of the present invention further include enantiomers of compounds of the formula (VI).

The compounds of the present invention include compounds having formula (VII):

(VII)

including hydrates, solvates, pharmaceutically acceptable salts, and complexes thereof.

The compounds of the present invention further include enantiomers of compounds of the formula (VII).

The compounds of the present invention further include compounds of the formula (VII) that are isotopically labeled with 1 to 10 deuterium atoms.

The compounds of the present invention include compounds having formula (VIII):

(VIII)

including hydrates, solvates, pharmaceutically acceptable salts, and complexes thereof.

The compounds of the present invention further include enantiomers of compounds of the formula (VIII).

The compounds of the present invention further include compounds of the formula (VIII) that are isotopically labeled with 1 to 10 deuterium atoms.

The compounds of the present invention include compounds having formula (IX):

(IX)

including hydrates, solvates, pharmaceutically acceptable salts, and complexes thereof.

The compounds of the present invention further include enantiomers of compounds of the formula (IX).

The compounds of the present invention further include compounds of the formula (IX) that are isotopically labeled with 1 to 10 deuterium atoms.

The compounds of the present invention include compounds having formula (X):

(X)

including hydrates, solvates, pharmaceutically acceptable salts, and complexes thereof.

The compounds of the present invention further include enantiomers of compounds of the formula (X).

The compounds of the present invention further include compounds of the formula (X) that are isotopically labeled with 1 to 10 deuterium atoms.

The present invention further relates to compositions comprising:
an effective amount of one or more compounds according to the present invention and an excipient.

The present invention also relates to a method for treating or preventing hepatic encephalopathy said method comprising administering to a subject an effective amount of a compound or composition according to the present invention.

The present invention yet further relates to a method for treating or preventing hepatic encephalopathy, wherein said method comprises administering to a subject a composition comprising an effective amount of one or more compounds according to the present invention and an excipient.

The present invention also relates to a method for treating or preventing disease or conditions associated with hepatic encephalopathy. Said methods comprise administering to a subject an effective amount of a compound or composition according to the present invention.

The present invention yet further relates to a method for treating or preventing disease or conditions associated with hepatic encephalopathy, wherein said method comprises administering to a subject a composition comprising an effective amount of one or more compounds according to the present invention and an excipient.

The present invention also relates to a method for treating or preventing diseases with free radical mediate stress and oxidative stress in their etiology, including, for example, epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS) said method comprising administering to a subject an effective amount of a compound or composition according to the present invention.

The present invention yet further relates to a method for treating or preventing diseases with free radical mediate stress and oxidative stress in their etiology, including, for example, epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS), wherein said method comprises administering to a subject a composition comprising an effective amount of one or more compounds according to the present invention and an excipient.

The present invention also relates to a method for treating or preventing disease or conditions associated with diseases with free radical mediate stress and oxidative stress in their etiology, including, for example, epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS). Said methods comprise administering to a subject an effective amount of a compound or composition according to the present invention.

The present invention yet further relates to a method for treating or preventing disease or conditions associated with diseases with free radical mediate stress and oxidative stress in their etiology, including, for example, epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS), wherein said method comprises administering to a subject a composition comprising an effective amount of one or more compounds according to the present invention and an excipient.

The present invention further relates to a process for preparing the functionalized 1,3-benzenediols of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

Figure 1:
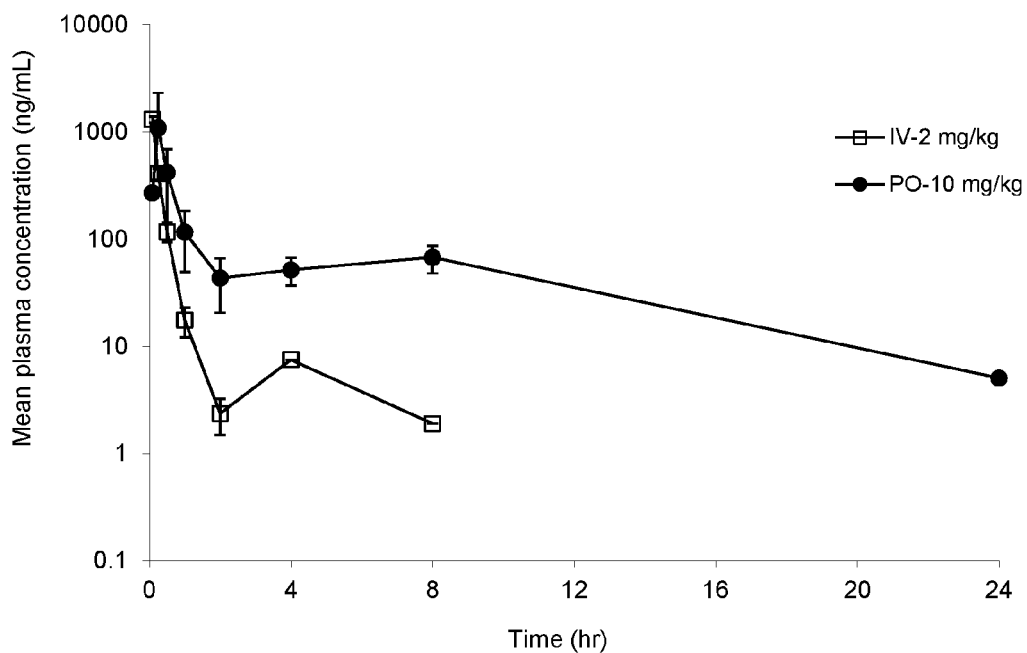
FIG. 1: Mean plasma concentration-time profiles of KLS-13019 (example 2) after single IV and PO administrations in CD1 mice (N=3/time point).

The functionalized 1,3-benzenediols of the present invention are capable of treating and preventing diseases associated with free radical mediated stress and oxidative stress including, for example, hepatic encephalopathy, Parkinson's disease, Alzheimer's, Huntington's disease, traumatic head injury, stroke, epilepsy, neuropathic pain, traumatic head injury, stroke, Chronic Traumatic Encephalopathy (CTE), Post Cardiac Arrest Hypoxic Ischemic Encephalopathy, and Epileptic Encephalopathy. It has been discovered that prevention of free radical mediated stress and oxidative stress will prevent damage and death of neuronal tissue, as well as prevent cognitive impairment, learning deficits, and memory impairment associated with damage and death of neuronal tissue. Without wishing to be limited by theory, it is believed that the neuroprotective agents of the disclosure can ameliorate, abate, otherwise cause to be controlled, diseases associated free radical mediated stress and oxidative stress. Diseases associated with free radical mediated stress and oxidative stress include, but are not limited to hepatic encephalopathy, epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, and neurodegenerative diseases such as Parkinson's disease, Alzheimer's, Huntington's disease, and amyotrophic lateral sclerosis (ALS).

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, isobutyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoroethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

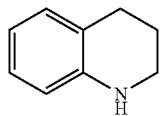

is, for the purposes of the present invention, considered a heterocyclic unit. 6,7-Dihydro-5H-cyclopentapyrimidine having the formula:

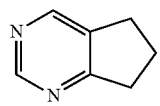

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

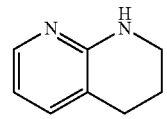

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{11}$, —SR$^{11}$, —N(R$^{11}$)$_2$, —NR$^{11}$C(O)R$^{11}$, —SO$_2$R$^{11}$, —SO$_2$OR$^{11}$, —SO$_2$N(R$^{11}$)$_2$, —C(O)R$^{11}$, —C(O)OR$^{11}$, —C(O)N(R$^{11}$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{11}$; wherein R$^{11}$, at each occurrence, independently is hydrogen, —OR$^{12}$, —SR$^{12}$, —C(O)R$^{12}$, —C(O)OR$^{12}$, —C(O)N (R$^{12}$)$_2$, —SO$_2$R$^{12}$, —S(O)$_2$OR$^{12}$, —N(R$^{12}$)$_2$, —NR$^{12}$C(O) R$^{12}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{11}$ units taken together with the atom(s) to which they are bound form an optionally substituted carbocycle or heterocycle wherein said carbocycle or heterocycle has 3 to 7 ring atoms; wherein $R^{12}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{12}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —$OR^{13}$; for example, —OH, —$OCH_3$, —$OCH_2CH_3$, —$OCH_2CH_2CH_3$;
ii) —$C(O)R^{13}$; for example, —$COCH_3$, —$COCH_2CH_3$, —$COCH_2CH_2CH_3$;
iii) —$C(O)OR^{13}$; for example, —$CO_2CH_3$, —$CO_2CH_2CH_3$, —$CO_2CH_2CH_2CH_3$;
iv) —$C(O)N(R^{13})_2$; for example, —$CONH_2$, —$CONHCH_3$, —$CON(CH_3)_2$;
v) —$N(R^{13})_2$; for example, —$NH_2$, —$NHCH_3$, —$N(CH_3)_2$, —$NH(CH_2CH_3)$;
vi) halogen: —F, —Cl, —Br, and —I;
vii) —$CH_eX_g$; wherein X is halogen, m is from 0 to 2, e+g=3; for example, —$CH_2F$, —$CHF_2$, —$CF_3$, —$CCl_3$, or —$CBr_3$;
viii) —$SO_2R^{13}$; for example, —$SO_2H$; —$SO_2CH_3$; —$SO_2C_6H_5$;
ix) $C_1$-$C_6$ linear, branched, or cyclic alkyl;
x) Cyano
xi) Nitro;
xii) $N(R^{13})C(O)R^{13}$;
xiii) Oxo (=O);
xiv) Heterocycle; and
xv) Heteroaryl.

wherein each $R^{13}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{13}$ units can be taken together to form a ring comprising 3-7 ring atoms. In certain aspects, each $R^{13}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the novel functionalized 1,3-benzenediols described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl -tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{12})_2$, each $R^{12}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "neuroprotection" shall mean the protecting of neurons in the brain, central nervous system or peripheral nervous system from death and/or damage. Preferably, the neurons are protected from death or damage caused by oxidative stress or excess glutamate.

As used herein, the term "neuroprotective agent" shall mean a compound that provides neuroprotection.

Except when noted, the terms "subject" or "patient" are used interchangeably and refer to mammals such as human patients and non-human primates, as well as experimental animals such as rabbits, rats, and mice, and other animals.

Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Novel Functionalized 1,3-Benzenediols of the Present Invention:

The compounds of the present invention are functionalized 1,3-benzenediols, and include all enantiomeric and diastereomeric forms and pharmaceutically accepted salts thereof having the formula:

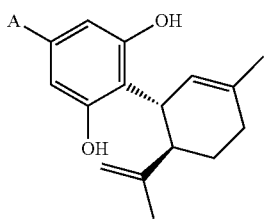

(I)

Including hydrates, solvates, pharmaceutically acceptable salts, prodrugs and complexes thereof, wherein:
A is selected from the group consisting of

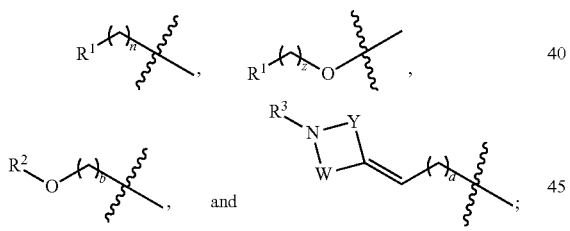

z is 0, 1, or 2;
When A is

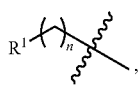

$R^1$ is selected from the group consisting of

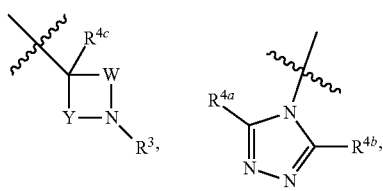

-continued

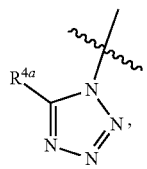 and 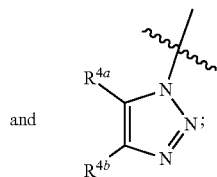

When A is

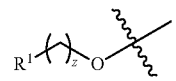

and z is 0, $R^1$ is

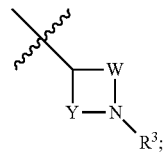

When A is

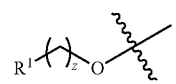

and z is 1, $R^1$ is

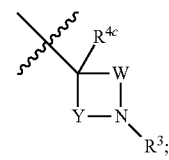

When A is

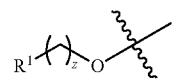

and z is 2, $R^1$ is selected from the group consisting of

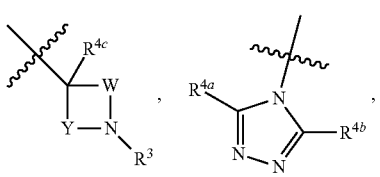

-continued

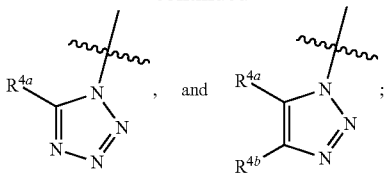

When R¹ is

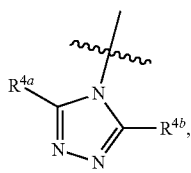

n is not 0;
When R¹ is

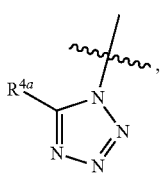

n is not 0;
When R¹ is

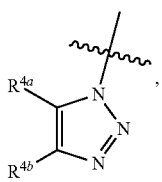

n is not 0;
R² is

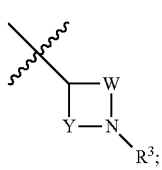

W is $(CH_2)_m$;
m is 1 or 2;
Y is $(CH_2)_q$;
q is 1 or 2;
n is 0, 1, 2, or 3:
b is 0, 1, 2, or 3;
d is 0, 1, 2, or 3;
R³ is selected from the group consisting of $COR^5$, $CO_2R^6$, $CONR^{7a}R^{7b}$, $SO_2NR^{7a}R^{7b}$, $SO_2R^8$, and optionally substituted heteroaryl;
$R^{4a}$ and $R^{4b}$ are each independently selected from the group consisting of hydrogen and $C_{1-6}$ alkyl;

$R^{4c}$ is selected from the group consisting of hydrogen and OH;
R⁵ is selected from the group consisting of hydrogen, $C_{1-6}$ alkyl, optional substituted heteroaryl, $—C(R^{9a}R^{9b})NR^{7a}R^{7b}$, and $—C(R^{9a}R^{9b})OR^{10}$;
R⁵ is also selected from optional substituted $C_{1-6}$ alkyl;
R⁶ is $C_{1-6}$ alkyl;
R⁶ is also selected from optional substituted $C_{1-6}$ alkyl;
$R^{7a}$ and $R^{7b}$ are each independently selected from the group consisting of hydrogen and $C_{1-6}$ alkyl;
$R^{7a}$ and $R^{7b}$ are also each independently selected from optional substituted $C_{1-6}$ alkyl;
R⁸ is selected from the group consisting of hydrogen, $C_{1-6}$ alkyl and optional substituted heteroaryl;
R⁸ is also selected from optional substituted $C_{1-6}$ alkyl;
$R^{9a}$ and $R^{9b}$ are each independently selected from the group consisting of hydrogen, $C_{1-6}$ alkyl, $C_{3-7}$ branched alkyl, $CH_2OH$, $CH(OH)CH_3$, $CH_2Ph$, $CH_2(4\text{-OH-Ph})$, $(CH_2)_4NH_2$, $(CH_2)_3NHC(NH_2)NH$, $CH_2(3\text{-indole})$, $CH_2(5\text{-imidazole})$, $CH_2CO_2H$, $CH_2CH_2CO_2H$, $CH_2CONH_2$, and $CH_2CH_2CONH_2$.
$R^{10}$ is selected from the group consisting of hydrogen and $C_{1-6}$ alkyl.

The compounds of the present invention further include enantiomers of compounds of the formula (I).

The compounds of the present invention further include compounds of the formula (I) that are isotopically labeled with 1 to 10 deuterium atoms.

The compounds of the present invention include compounds having formula (II):

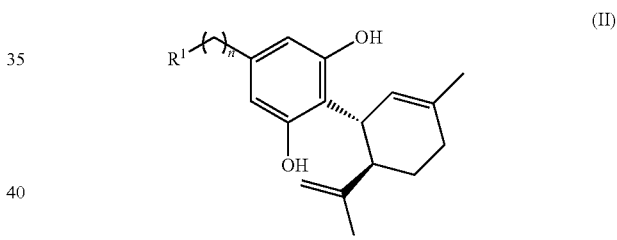

(II)

including hydrates, solvates, pharmaceutically acceptable salts, and complexes thereof.

The compounds of the present invention further include enantiomers of compounds of the formula (II).

The compounds of the present invention further include compounds of the formula (II) that are isotopically labeled with 1 to 10 deuterium atoms.

The compounds of the present invention include compounds having formula (III):

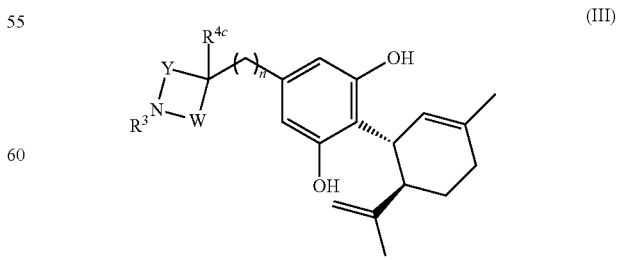

(III)

including hydrates, solvates, pharmaceutically acceptable salts, and complexes thereof.

The compounds of the present invention further include enantiomers of compounds of the formula (III).

The compounds of the present invention further include compounds of the formula (III) that are isotopically labeled with 1 to 10 deuterium atoms.

The compounds of the present invention include compounds having formula (IV):

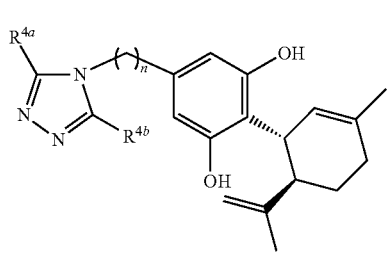

(IV)

including hydrates, solvates, pharmaceutically acceptable salts, and complexes thereof.

The compounds of the present invention further include enantiomers of compounds of the formula (IV).

The compounds of the present invention further include compounds of the formula (IV) that are isotopically labeled with 1 to 10 deuterium atoms.

The compounds of the present invention include compounds having formula (V):

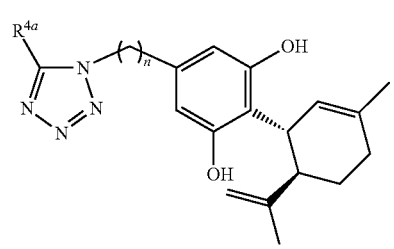

(V)

including hydrates, solvates, pharmaceutically acceptable salts, and complexes thereof.

The compounds of the present invention further include enantiomers of compounds of the formula (V).

The compounds of the present invention further include compounds of the formula (V) that are isotopically labeled with 1 to 10 deuterium atoms.

The compounds of the present invention include compounds having formula (VI):

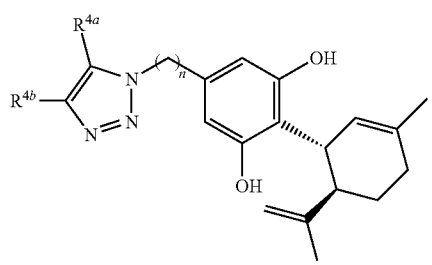

(VI)

including hydrates, solvates, pharmaceutically acceptable salts, and complexes thereof.

The compounds of the present invention further include enantiomers of compounds of the formula (VI).

The compounds of the present invention further include compounds of the formula (VI) that are isotopically labeled with 1 to 10 deuterium atoms.

The compounds of the present invention include compounds having formula (VII):

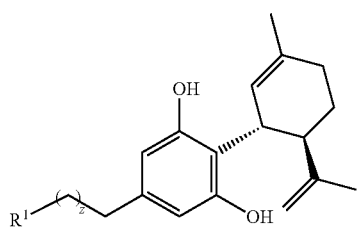

(VII)

including hydrates, solvates, pharmaceutically acceptable salts, and complexes thereof.

The compounds of the present invention further include enantiomers of compounds of the formula (VII).

The compounds of the present invention further include compounds of the formula (VII) that are isotopically labeled with 1 to 10 deuterium atoms.

The compounds of the present invention include compounds having formula (VIII):

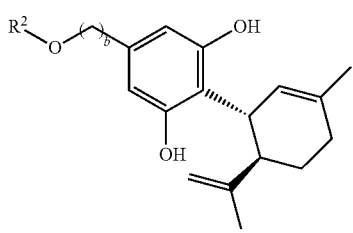

(VIII)

including hydrates, solvates, pharmaceutically acceptable salts, and complexes thereof.

The compounds of the present invention further include enantiomers of compounds of the formula (VIII).

The compounds of the present invention further include compounds of the formula (VIII) that are isotopically labeled with 1 to 10 deuterium atoms.

The compounds of the present invention include compounds having formula (IX):

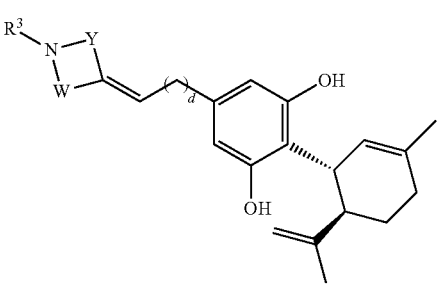

(IX)

including hydrates, solvates, pharmaceutically acceptable salts, and complexes thereof.

The compounds of the present invention further include enantiomers of compounds of the formula (IX).

The compounds of the present invention further include compounds of the formula (IX) that are isotopically labeled with 1 to 10 deuterium atoms.

The compounds of the present invention include compounds having formula (X):

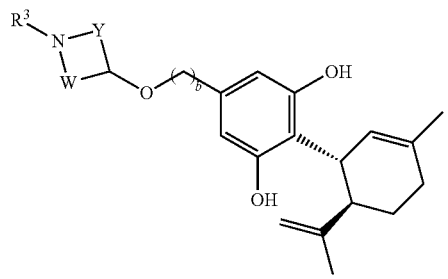

(X)

including hydrates, solvates, pharmaceutically acceptable salts, and complexes thereof.

The compounds of the present invention further include enantiomers of compounds of the formula (X).

The compounds of the present invention further include compounds of the formula (X) that are isotopically labeled with 1 to 10 deuterium atoms.

In some embodiments A is

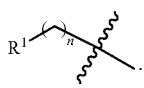

In some embodiments A is

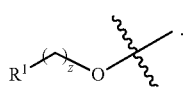

In some embodiments A is

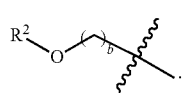

In some embodiments A is

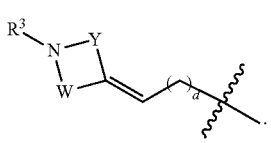

In some embodiments z is 0.
In some embodiments z is 1.
In some embodiments z is 2.

In some embodiments $R^1$ is

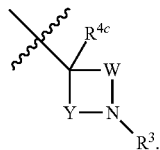

In some embodiments $R^1$ is

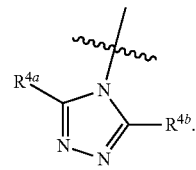

In some embodiments $R^1$ is

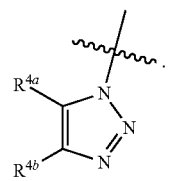

In some embodiments $R^1$ is

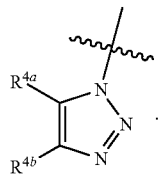

In some embodiments $R^2$ is

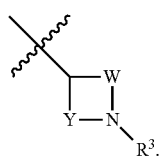

In some embodiments n is 0.
In some embodiments n is 1.
In some embodiments n is 2.
In some embodiments n is 3.
In some embodiments b is 0.
In some embodiments b is 1.
In some embodiments b is 2.
In some embodiments b is 3.
In some embodiments d is 0.
In some embodiments d is 1.
In some embodiments d is 2.
In some embodiments d is 3.
In some embodiments W is $(CH_2)$.
In some embodiments W is $(CH_2)_2$.

In some embodiments m is 1.
In some embodiments m is 2.
In some embodiments Y is (CH$_2$).
In some embodiments Y is (CH$_2$)$_2$.
In some embodiments q is 1.
In some embodiments q is 2.
In some embodiments R$^3$ is COR$^5$.
In some embodiments R$^3$ is CO$_2$R$^6$.
In some embodiments R$^3$ is CONR$^{7a}$R$^{7b}$.
In some embodiments R$^3$ is SO$_2$NR$^{7a}$R$^{7b}$.
In some embodiments R$^3$ is SO$_2$R$^8$.
In some embodiments R$^3$ is optionally substituted heteroaryl.
In some embodiments R$^{4a}$ is hydrogen.
In some embodiments R$^{4a}$ is C$_{1-6}$ alkyl.
In some embodiments R$^{4b}$ is hydrogen.
In some embodiments R$^{4b}$ is C$_{1-6}$ alkyl.
In some embodiments R$^{4c}$ is OH.
In some embodiments R$^{4c}$ is hydrogen.
In some embodiments R$^5$ is hydrogen.
In some embodiments R$^5$ is C$_{1-6}$ alkyl.
In some embodiments R$^5$ is optionally substituted heteroaryl.
In some embodiments R$^5$ is —C(R$^{9a}$R$^{9b}$)NR$^{7a}$R$^{7b}$.
In some embodiments R$^5$ is —C(R$^{9a}$R$^{9b}$)OR$^{10}$.
In some embodiments R$^5$ is optional substituted C$_{1-6}$ alkyl.
In some embodiments R$^6$ is C$_{1-6}$ alkyl.
In some embodiments R$^6$ is optional substituted C$_{1-6}$ alkyl.
In some embodiments R$^{7a}$ is hydrogen.
In some embodiments R$^{7a}$ is C$_{1-6}$ alkyl.
In some embodiments R$^{7a}$ is optional substituted C$_{1-6}$ alkyl.
In some embodiments R$^{7b}$ is hydrogen.
In some embodiments R$^{7b}$ is C$_{1-6}$ alkyl.
In some embodiments R$^{7b}$ is optional substituted C$_{1-6}$ alkyl.
In some embodiments R$^8$ is hydrogen.
In some embodiments R$^8$ is C$_{1-6}$ alkyl.
In some embodiments R$^8$ is optionally substituted heteroaryl.
In some embodiments R$^8$ is optional substituted C$_{1-6}$ alkyl.
In some embodiments R$^{9a}$ is hydrogen.
In some embodiments R$^{9a}$ is C$_{1-6}$ alkyl.
In some embodiments R$^{9a}$ is C$_{3-7}$ branched alkyl.
In some embodiments R$^{9a}$ is CH$_2$OH.
In some embodiments R$^{9a}$ is CH(OH)CH$_3$.
In some embodiments R$^{9a}$ is CH$_2$Ph.
In some embodiments R$^{9a}$ is CH$_2$(4-OH-Ph).
In some embodiments R$^{9a}$ is (CH$_2$)$_4$NH$_2$.
In some embodiments R$^{9a}$ is (CH$_2$)$_3$NHC(NH$_2$)NH.
In some embodiments R$^{9a}$ is CH$_2$(3-indole).
In some embodiments R$^{9a}$ is CH$_2$(5-imidazole).
In some embodiments R$^{9a}$ is CH$_2$CO$_2$H.
In some embodiments R$^{9a}$ is CH$_2$CH$_2$CO$_2$H.
In some embodiments R$^{9a}$ is CH$_2$CONH$_2$.
In some embodiments R$^{9a}$ is CH$_2$CH$_2$CONH$_2$.
In some embodiments R$^{9b}$ is hydrogen.
In some embodiments R$^{9b}$ is C$_{1-6}$ alkyl.
In some embodiments R$^{9b}$ is C$_{3-7}$ branched alkyl.
In some embodiments R$^{9b}$ is CH$_2$OH.
In some embodiments R$^{9b}$ is CH(OH)CH$_3$.
In some embodiments R$^{9b}$ is CH$_2$Ph.
In some embodiments R$^{9b}$ is CH$_2$(4-OH-Ph).
In some embodiments R$^{9b}$ is (CH$_2$)$_4$NH$_2$.
In some embodiments R$^{9b}$ is (CH$_2$)$_3$NHC(NH$_2$)NH.
In some embodiments R$^{9b}$ is CH$_2$(3-indole).
In some embodiments R$^{9b}$ is CH$_2$(5-imidazole).
In some embodiments R$^{9b}$ is CH$_2$CO$_2$H.
In some embodiments R$^{9b}$ is CH$_2$CH$_2$CO$_2$H.
In some embodiments R$^{9b}$ is CH$_2$CONH$_2$.
In some embodiments R$^{9b}$ is CH$_2$CH$_2$CONH$_2$.
In some embodiments R$^{10}$ is hydrogen.
In some embodiments R$^{10}$ is C$_{1-6}$ alkyl.

Compounds of the present invention include compounds having the formula (III) or a pharmaceutically acceptable salt form thereof:

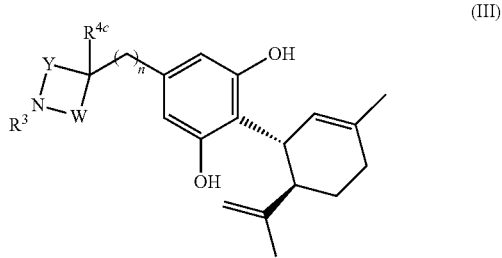

(III)

wherein non-limiting examples of R$^3$, R$^{4c}$, W and n are defined herein below in Table 1.

TABLE 1

| Entry | R$^3$ | R$^{4c}$ | Y | W | N |
|---|---|---|---|---|---|
| 1 | COCH$_3$ | H | CH$_2$ | CH$_2$ | 1 |
| 2 | CO$_2$CH$_3$ | H | CH$_2$ | CH$_2$ | 1 |
| 3 | CO$_2$CH$_2$CH$_3$ | H | CH$_2$ | CH$_2$ | 1 |
| 4 | CON(CH$_3$)$_2$ | H | CH$_2$ | CH$_2$ | 1 |
| 5 | SO$_2$N(CH$_3$)$_2$ | H | CH$_2$ | CH$_2$ | 1 |
| 6 | SO$_2$CH$_3$ | H | CH$_2$ | CH$_2$ | 1 |
| 7 | COCH$_3$ | H | CH$_2$ | CH$_2$CH$_2$ | 1 |
| 8 | CO$_2$CH$_3$ | H | CH$_2$ | CH$_2$CH$_2$ | 1 |
| 9 | CO$_2$CH$_2$CH$_3$ | H | CH$_2$ | CH$_2$CH$_2$ | 1 |
| 10 | CON(CH$_3$)$_2$ | H | CH$_2$ | CH$_2$CH$_2$ | 1 |
| 11 | SO$_2$N(CH$_3$)$_2$ | H | CH$_2$ | CH$_2$CH$_2$ | 1 |
| 12 | SO$_2$CH$_3$ | H | CH$_2$ | CH$_2$CH$_2$ | 1 |
| 13 | COCH$_3$ | H | CH$_2$CH$_2$ | CH$_2$ | 1 |
| 14 | CO$_2$CH$_3$ | H | CH$_2$CH$_2$ | CH$_2$ | 1 |
| 15 | CO$_2$CH$_2$CH$_3$ | H | CH$_2$CH$_2$ | CH$_2$ | 1 |
| 16 | CON(CH$_3$)$_2$ | H | CH$_2$CH$_2$ | CH$_2$ | 1 |
| 17 | SO$_2$N(CH$_3$)$_2$ | H | CH$_2$CH$_2$ | CH$_2$ | 1 |
| 18 | SO$_2$CH$_3$ | H | CH$_2$CH$_2$ | CH$_2$ | 1 |
| 19 | COCH$_3$ | H | CH$_2$CH$_2$ | CH$_2$CH$_2$ | 1 |
| 20 | CO$_2$CH$_3$ | H | CH$_2$CH$_2$ | CH$_2$CH$_2$ | 1 |
| 21 | CO$_2$CH$_2$CH$_3$ | H | CH$_2$CH$_2$ | CH$_2$CH$_2$ | 1 |
| 22 | CON(CH$_3$)$_2$ | H | CH$_2$CH$_2$ | CH$_2$CH$_2$ | 1 |
| 23 | SO$_2$N(CH$_3$)$_2$ | H | CH$_2$CH$_2$ | CH$_2$CH$_2$ | 1 |
| 24 | SO$_2$CH$_3$ | H | CH$_2$CH$_2$ | CH$_2$CH$_2$ | 1 |

Compounds of the present invention include compounds having the formula (II) or a pharmaceutically acceptable salt form thereof:

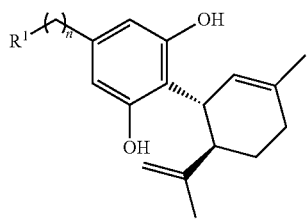

(II)

wherein non-limiting examples of $R^1$ and n are defined herein below in Table 2.

TABLE 2

| Entry | $R^1$ | n |
|---|---|---|
| 1 | (pyrazol-1-yl) | 1 |
| 2 | (1,2,3-triazol-1-yl) | 1 |
| 3 | (1,2,4-triazol-1-yl) | 1 |
| 4 | (pyrazol-1-yl) | 2 |
| 5 | (tetrazol-1-yl) | 2 |
| 6 | (1,2,4-triazol-1-yl) | 2 |

Compounds of the present invention include compounds having the formula (IX) or a pharmaceutically acceptable salt form thereof:

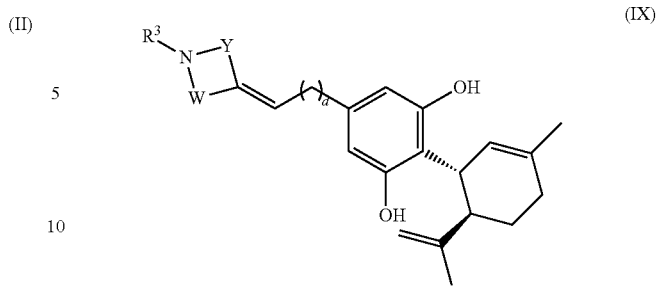

(IX)

wherein non-limiting examples of $R^3$, Y, W, and d are defined herein below in Table 3.

TABLE 3

| Entry | $R^3$ | Y | W | d |
|---|---|---|---|---|
| 1 | $COCH_3$ | $CH_2$ | $CH_2$ | 1 |
| 2 | $CO_2CH_3$ | $CH_2$ | $CH_2$ | 1 |
| 3 | $CO_2CH_2CH_3$ | $CH_2$ | $CH_2$ | 1 |
| 4 | $CON(CH_3)_2$ | $CH_2$ | $CH_2$ | 1 |
| 5 | $SO_2N(CH_3)_2$ | $CH_2$ | $CH_2$ | 1 |
| 6 | $SO_2CH_3$ | $CH_2$ | $CH_2$ | 1 |
| 7 | $COCH_3$ | $CH_2$ | $CH_2CH_2$ | 1 |
| 8 | $CO_2CH_3$ | $CH_2$ | $CH_2CH_2$ | 1 |
| 9 | $CO_2CH_2CH_3$ | $CH_2$ | $CH_2CH_2$ | 1 |
| 10 | $CON(CH_3)_2$ | $CH_2$ | $CH_2CH_2$ | 1 |
| 11 | $SO_2N(CH_3)_2$ | $CH_2$ | $CH_2CH_2$ | 1 |
| 12 | $SO_2CH_3$ | $CH_2$ | $CH_2CH_2$ | 1 |
| 13 | $COCH_3$ | $CH_2CH_2$ | $CH_2$ | 1 |
| 14 | $CO_2CH_3$ | $CH_2CH_2$ | $CH_2$ | 1 |
| 15 | $CO_2CH_2CH_3$ | $CH_2CH_2$ | $CH_2$ | 1 |
| 16 | $CON(CH_3)_2$ | $CH_2CH_2$ | $CH_2$ | 1 |
| 17 | $SO_2N(CH_3)_2$ | $CH_2CH_2$ | $CH_2$ | 1 |
| 18 | $SO_2CH_3$ | $CH_2CH_2$ | $CH_2$ | 1 |
| 19 | $COCH_3$ | $CH_2CH_2$ | $CH_2CH_2$ | 1 |
| 20 | $CO_2CH_3$ | $CH_2CH_2$ | $CH_2CH_2$ | 1 |
| 21 | $CO_2CH_2CH_3$ | $CH_2CH_2$ | $CH_2CH_2$ | 1 |
| 22 | $CON(CH_3)_2$ | $CH_2CH_2$ | $CH_2CH_2$ | 1 |
| 23 | $SO_2N(CH_3)_2$ | $CH_2CH_2$ | $CH_2CH_2$ | 1 |
| 24 | $SO_2CH_3$ | $CH_2CH_2$ | $CH_2CH_2$ | 1 |

Compounds of the present invention include compounds having the formula (X) or a pharmaceutically acceptable salt form thereof:

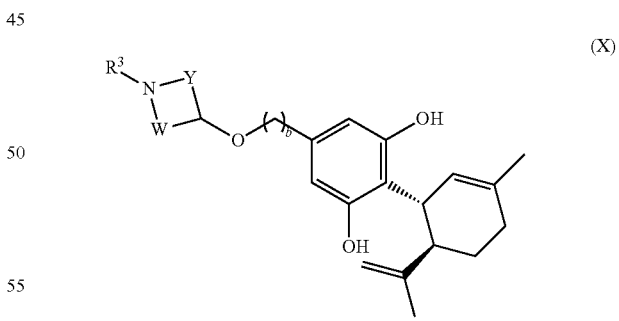

(X)

wherein non-limiting examples of $R^3$, Y, W, and b are defined herein below in Table 4.

TABLE 4

| Entry | $R^3$ | Y | W | B |
|---|---|---|---|---|
| 1 | $COCH_3$ | $CH_2$ | $CH_2$ | 1 |
| 2 | $CO_2CH_3$ | $CH_2$ | $CH_2$ | 1 |
| 3 | $CO_2CH_2CH_3$ | $CH_2$ | $CH_2$ | 1 |

TABLE 4-continued

| Entry | R³ | Y | W | B |
|---|---|---|---|---|
| 4 | CON(CH₃)₂ | CH₂ | CH₂ | 1 |
| 5 | SO₂N(CH₃)₂ | CH₂ | CH₂ | 1 |
| 6 | SO₂CH₃ | CH₂ | CH₂ | 1 |
| 7 | COCH₃ | CH₂ | CH₂CH₂ | 1 |
| 8 | CO₂CH₃ | CH₂ | CH₂CH₂ | 1 |
| 9 | CO₂CH₂CH₃ | CH₂ | CH₂CH₂ | 1 |
| 10 | CON(CH₃)₂ | CH₂ | CH₂CH₂ | 1 |
| 11 | SO₂N(CH₃)₂ | CH₂ | CH₂CH₂ | 1 |
| 12 | SO₂CH₃ | CH₂ | CH₂CH₂ | 1 |
| 13 | COCH₃ | CH₂CH₂ | CH₂ | 1 |
| 14 | CO₂CH₃ | CH₂CH₂ | CH₂ | 1 |
| 15 | CO₂CH₂CH₃ | CH₂CH₂ | CH₂ | 1 |
| 16 | CON(CH₃)₂ | CH₂CH₂ | CH₂ | 1 |
| 17 | SO₂N(CH₃)₂ | CH₂CH₂ | CH₂ | 1 |
| 18 | SO₂CH₃ | CH₂CH₂ | CH₂ | 1 |
| 19 | COCH₃ | CH₂CH₂ | CH₂CH₂ | 1 |
| 20 | CO₂CH₃ | CH₂CH₂ | CH₂CH₂ | 1 |
| 21 | CO₂CH₂CH₃ | CH₂CH₂ | CH₂CH₂ | 1 |
| 22 | CON(CH₃)₂ | CH₂CH₂ | CH₂CH₂ | 1 |
| 23 | SO₂N(CH₃)₂ | CH₂CH₂ | CH₂CH₂ | 1 |
| 24 | SO₂CH₃ | CH₂CH₂ | CH₂CH₂ | 1 |

For the purposes of demonstrating the manner in which the compounds of the present invention are named and referred to herein, the compound having the formula:

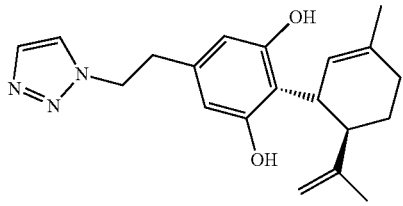

has the chemical name 5-(2-(1H-1,2,3-triazol-1-yl)ethyl)-2-((1R,6R)-3-methyl-6-(prop-1-en-2-yl)cyclohex-2-enyl)benzene-1,3-diol.

For the purposes of demonstrating the manner in which the compounds of the present invention are named and referred to herein, the compound having the formula:

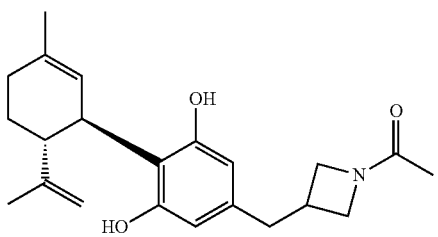 [SMILES: C=C(C)[C@@H]1CCC(C)=C[C@H]1c1c(O)cc(CC2CN(C(C)=O)C2)cc1O]

has the chemical name 1-(3-(3,5-dihydroxy-4-((1R,6R)-3-methyl-6-(prop-1-en-2-yl)cyclohex-2-enyl)benzyl)azetidin-1-yl)ethanone.

For the purposes of demonstrating the manner in which the compounds of the present invention are named and referred to herein, the compound having the formula:

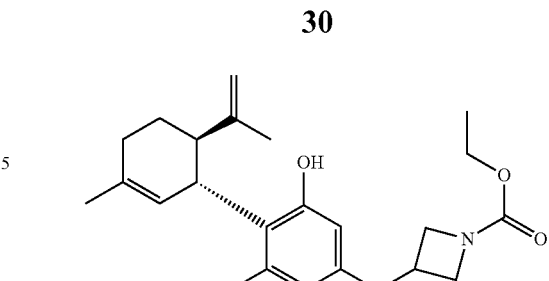

has the chemical name ethyl 3-(3,5-dihydroxy-4-((1R,6R)-3-methyl-6-(prop-1-en-2-yl)cyclohex-2-enyl)benzyl)azetidine-1-carboxylate.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the and one or more excipients of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^{1}$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes below.

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the processes outlined in schemes 1-48.

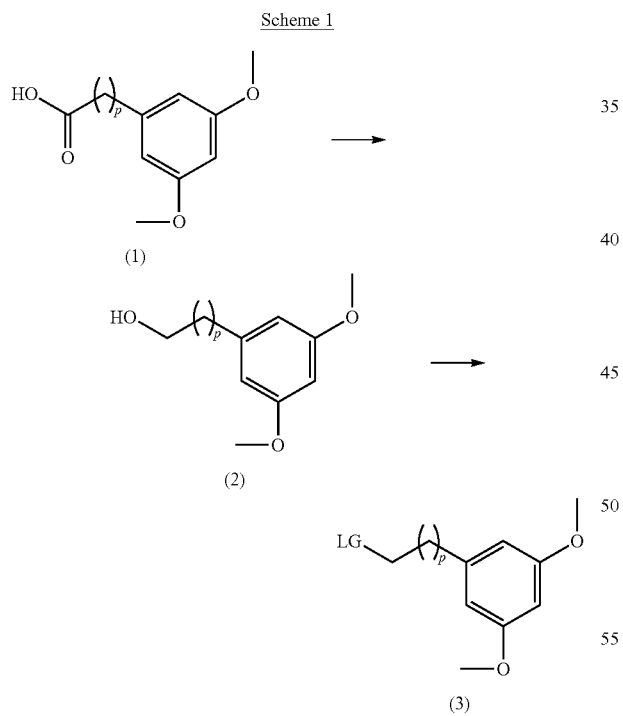

A suitably substituted compound of formula (1), a known compound or compound prepared by known methods, wherein p is 0, 1, or 2, is reacted with a reducing agent such as lithium aluminum hydride, sodium borohydride, sodium cyanoborohydride, lithium borohydride, and the like, in an organic solvent such as tetrahydrofuran, 1,4-dioxane, dichloromethane, chloroform, 1,2-dichloroethane, and the like, optionally with heating, optionally with microwave irradiation to provide a compound of the formula (2). A compound of the formula 2 is then converted into a compound of the formula (3) wherein LG is a leaving group such as iodine, bromine, methanesulfonate, tosylate and the like by one of the following methods. A compound of the formula (2) is reacted with iodine in the presence of triphenyl phosphine, in the presence of imidazole, in an organic solvent such as tetrahydrofuran, 1,4-dioxane, dichloromethane, chloroform, 1,2-dichloroethane, and the like, optionally with heating, optionally with microwave irradiation to provide a compound of the formula (3) wherein LG is an iodine atom. Alternatively, a compound of the formula (2) is reacted with bromine in the presence of triphenyl phosphine, in the presence of imidazole, in an organic solvent such as tetrahydrofuran, 1,4-dioxane, dichloromethane, chloroform, 1,2-dichloroethane, and the like, optionally with heating, optionally with microwave irradiation to provide a compound of the formula (3) wherein LG is an bromine atom. Alternatively, a compound of the formula (2) is reacted with carbon tetrabromide in the presence of triphenyl phosphine, in the presence of imidazole, in an organic solvent such as tetrahydrofuran, 1,4-dioxane, dichloromethane, chloroform, 1,2-dichloroethane, and the like, optionally with heating, optionally with microwave irradiation to provide a compound of the formula (3) wherein LG is an bromine atom. Alternatively, a compound of the formula (2) is reacted with methanesulfonyl chloride in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (3) wherein LG is a methanesulfonate. Alternatively, a compound of the formula (2) is reacted with toluenesulfonyl chloride in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (3) wherein LG is a toluenesulfonate.

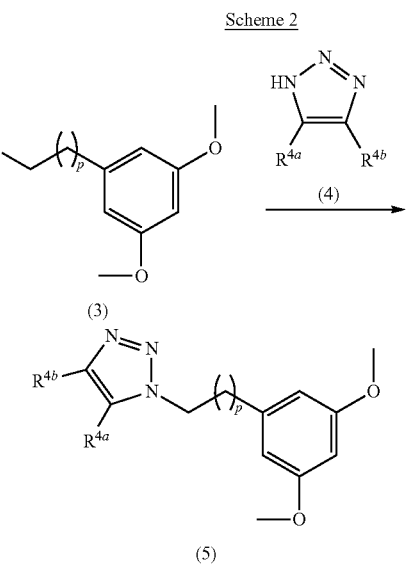

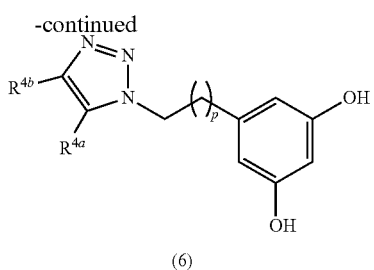

(6)

A compound of the formula (3) is reacted with a compound of the formula (4), a known compound or compound prepared by known methods, in the presence of a base such as sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (5). A compound of the formula (5) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (6). Alternatively, a compound of the formula (5) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (6).

Scheme 3

A compound of the formula (6) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (8).

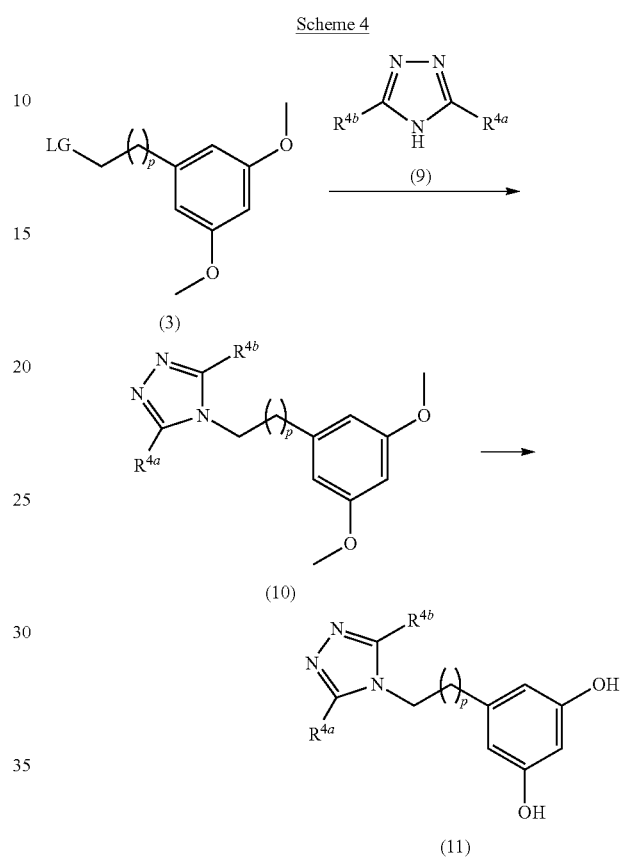

A compound of the formula (3) is reacted with a compound of the formula (9), a known compound or compound prepared by known methods, in the presence of a base such as sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (10). A compound of the formula (10) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (11). Alternatively, a compound of the formula (10) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (11).

Scheme 5

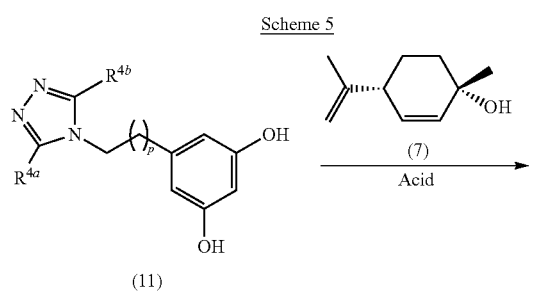

(11)

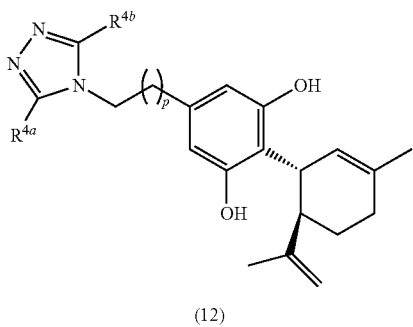

(12)

A compound of the formula (11) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (12).

Scheme 6

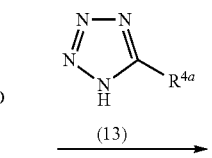

(3)

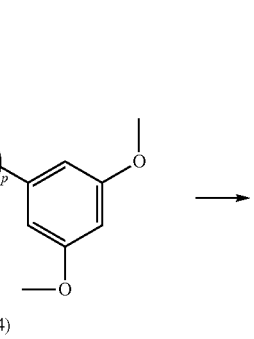

(14)

-continued

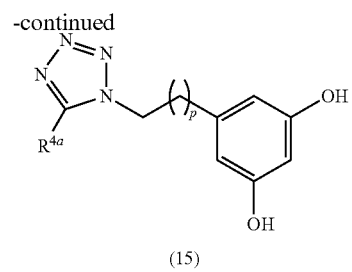

(15)

A compound of the formula (3) is reacted with a compound of the formula (13), a known compound or compound prepared by known methods, in the presence of a base such as sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (14). A compound of the formula (14) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (15). Alternatively, a compound of the formula (14) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (15).

Scheme 7

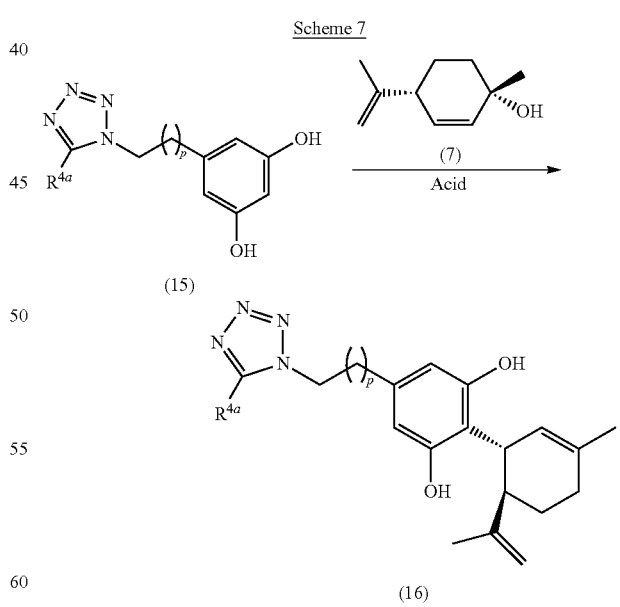

A compound of the formula (15) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (16).

Scheme 8

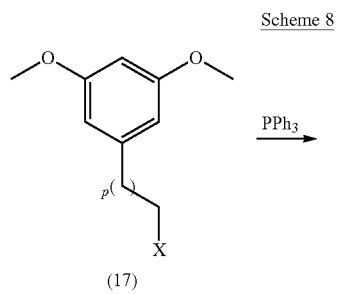

(17)

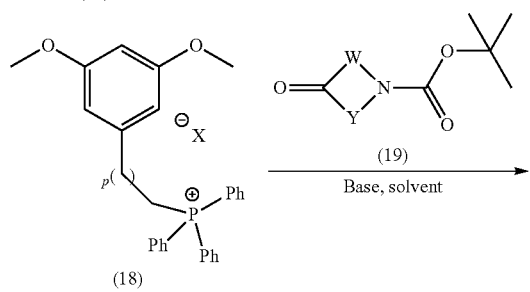

(18) → (19) Base, solvent

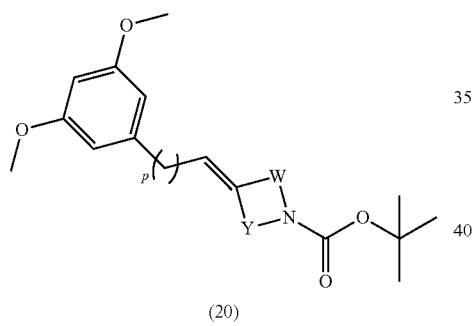

(20)

Sheme 9

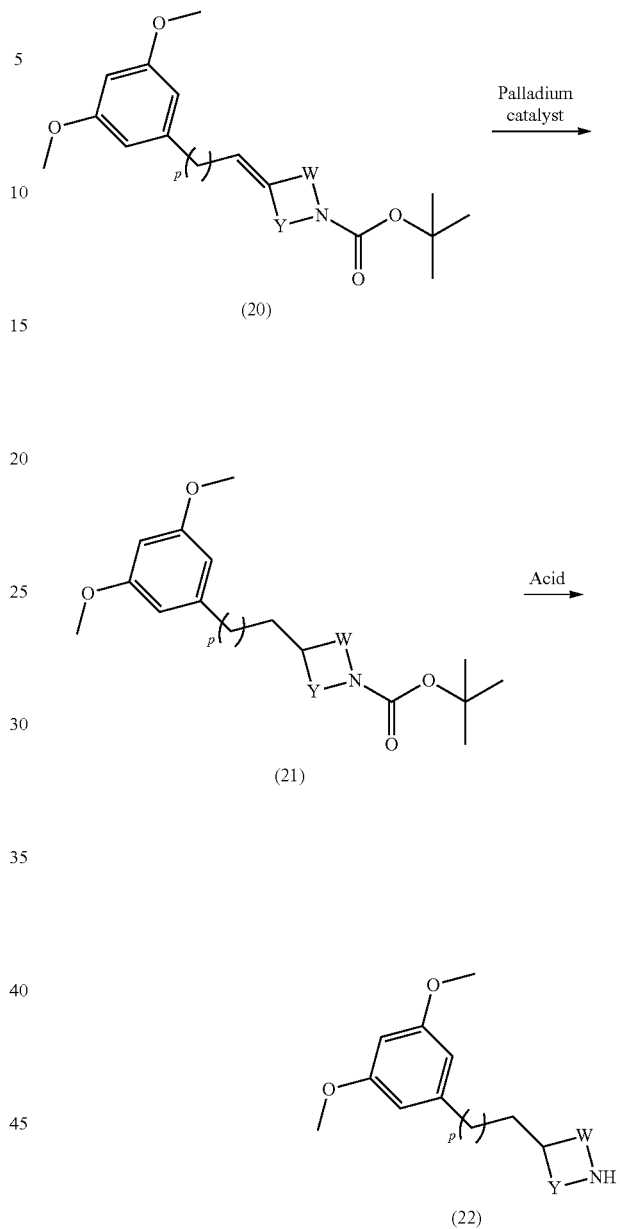

A compound of the formula (17) wherein X is a halogen, a known compound or a compound made by known methods, wherein p is 0, 1, or 2, is reacted with triphenylphosphine in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (18). A compound of the formula (18) wherein X is a halogen, is reacted with a compound of the formula (19), a known compound or a compound prepared by known methods, in the presence of a base such as n-butyl lithium, sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (20).

A compound of the formula (20) is reacted with hydrogen in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (21). A compound of the formula (21) is then reacted with an acid such as hydrochloric acid, sulfuric acid, trifluoroacetic acid, and the like, in an organic solvent such as methanol, ethanol, tetrahydrofuran, 1,4-dioxane, dichloromethane, chloroform, 1,2-dichloroethane, N,N-dimethylformamide, and the like, to provide a compound of the formula (22).

Scheme 10

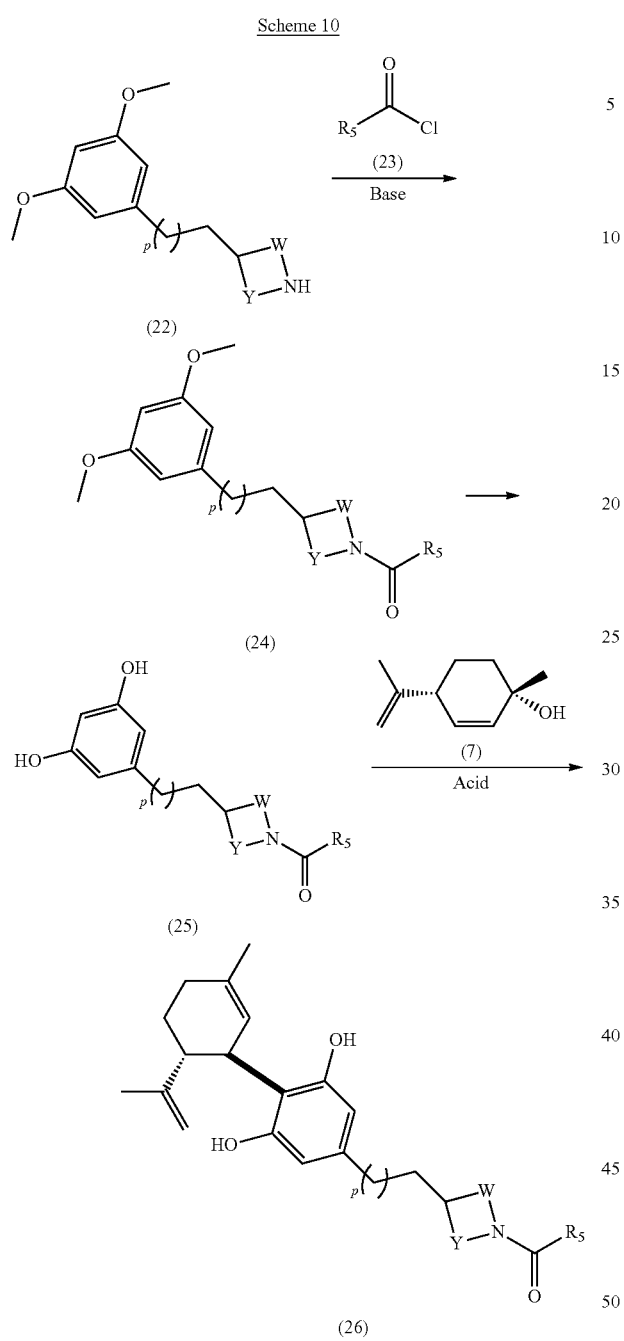

Alternatively, a compound of the formula (24) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (25). A compound of the formula (25) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (26).

Scheme 11

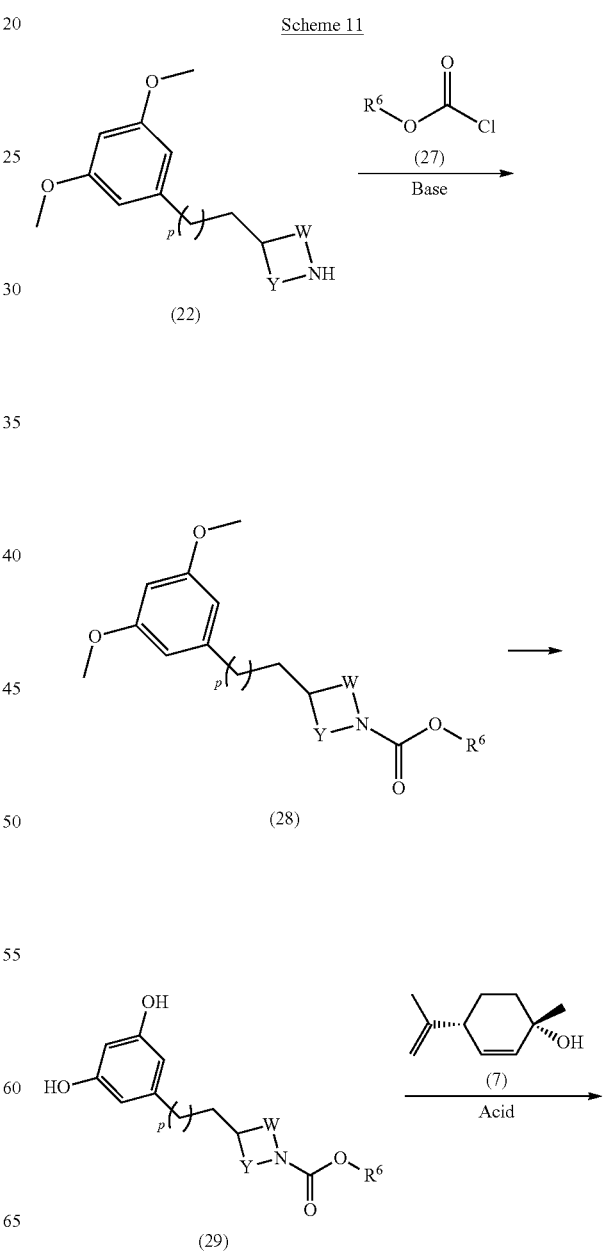

A compound of the formula (22) is reacted with a compound of the formula (23), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (24). A compound of the formula (24) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (25).

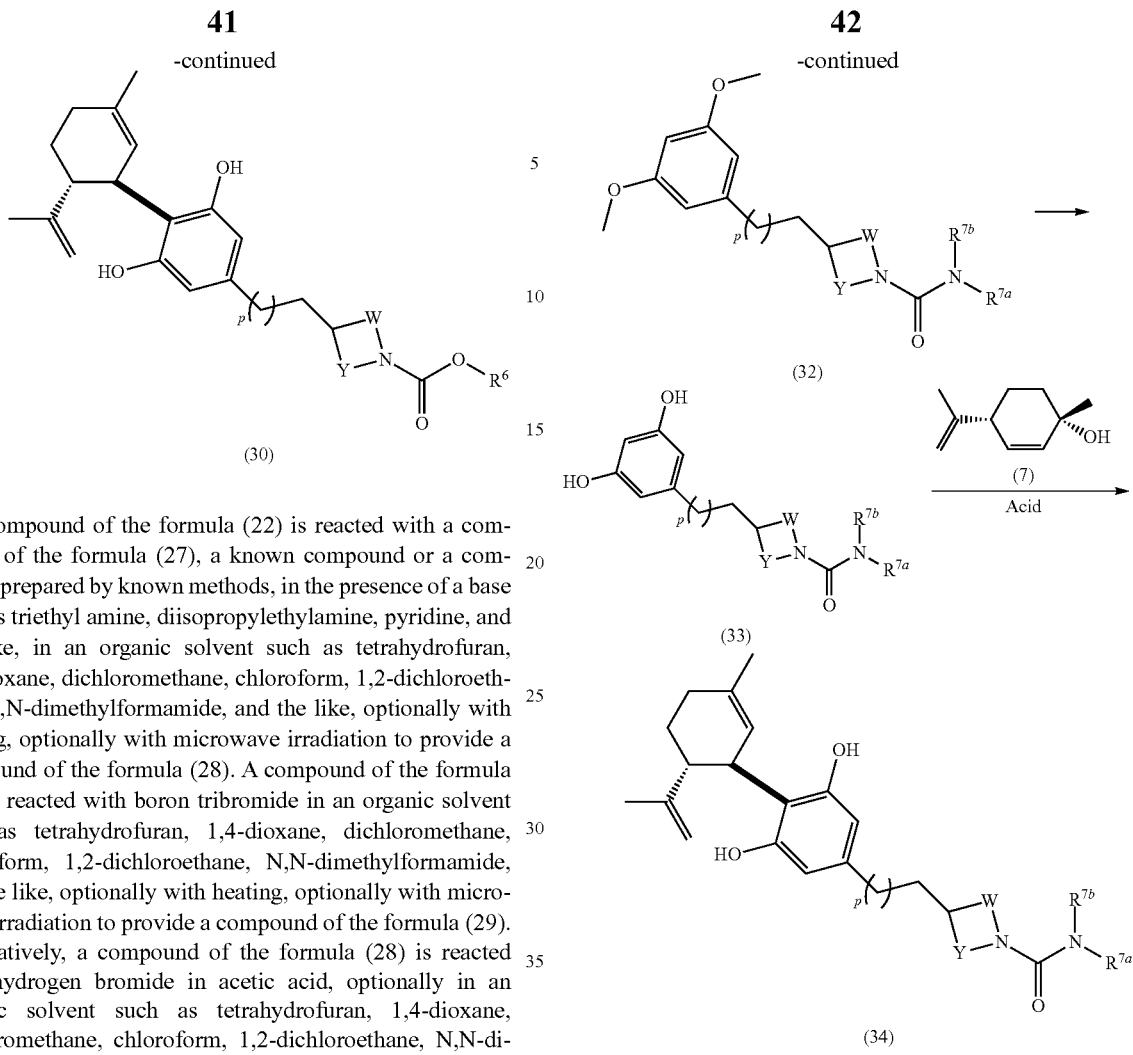

A compound of the formula (22) is reacted with a compound of the formula (27), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (28). A compound of the formula (28) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (29). Alternatively, a compound of the formula (28) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (29). A compound of the formula (29) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (30).

Scheme 12

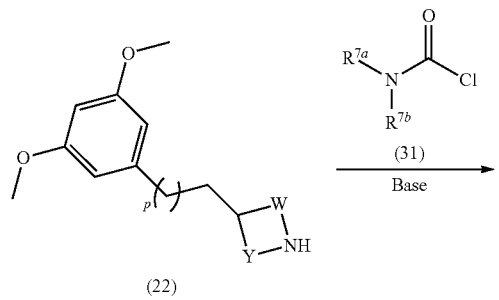

A compound of the formula (22) is reacted with a compound of the formula (31), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (32). A compound of the formula (32) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (33). Alternatively, a compound of the formula (32) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (33). A compound of the formula (33) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N- dimethylformamide, and the like, optionally with heating, optionally with microwave irradiation to provide a compound of the formula (34).

Scheme 13

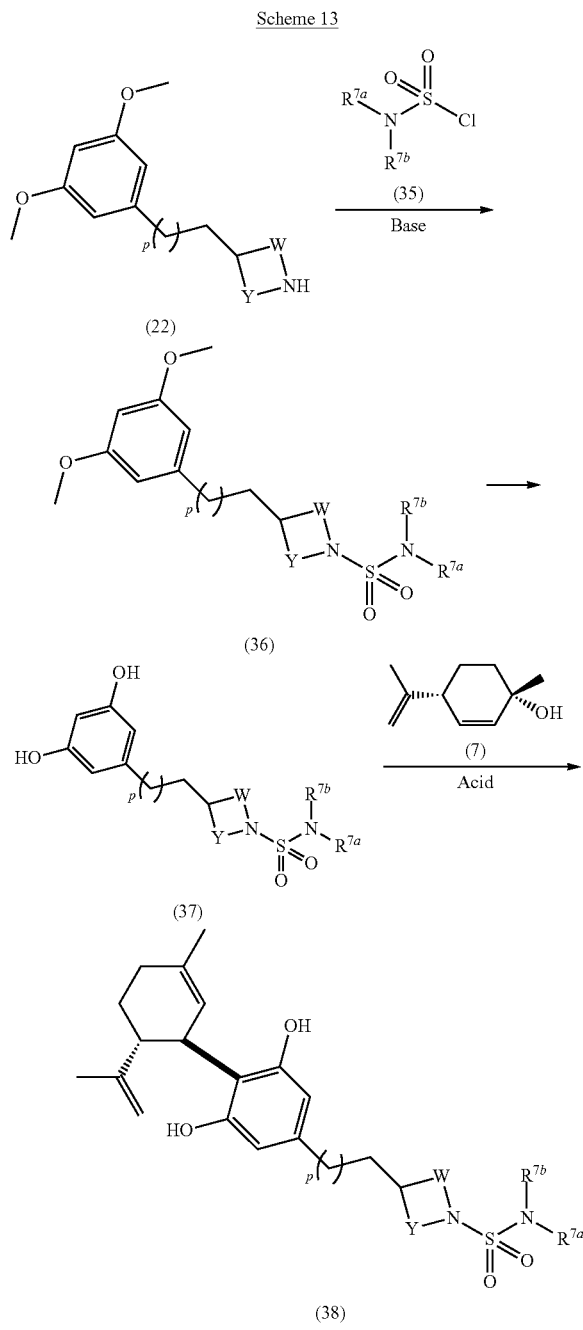

chloroform, 1,2-dichloroethane, N,N-dimethylformamide, and the like, optionally with heating, optionally with microwave irradiation to provide a compound of the formula (37). Alternatively, a compound of the formula (36) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (37). A compound of the formula (37) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (38).

Scheme 14

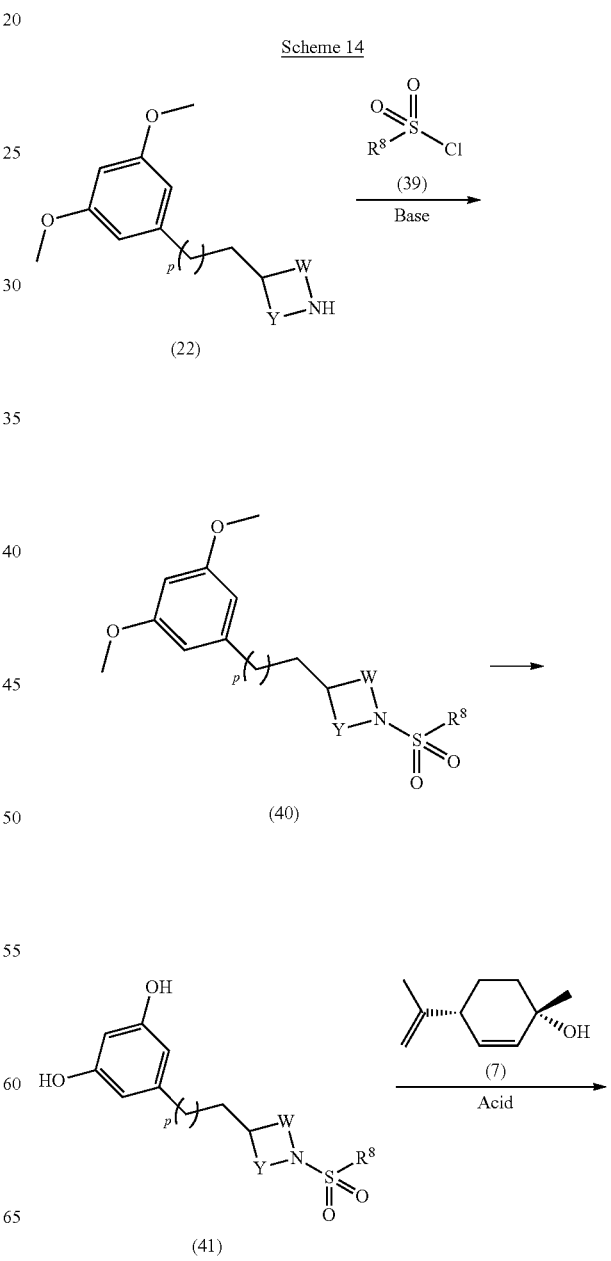

A compound of the formula (22) is reacted with a compound of the formula (35), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (36). A compound of the formula (36) is reacted with boron tribromide in an organic solvent such as tetrahydrofuran, 1,4-dioxane, dichloromethane,

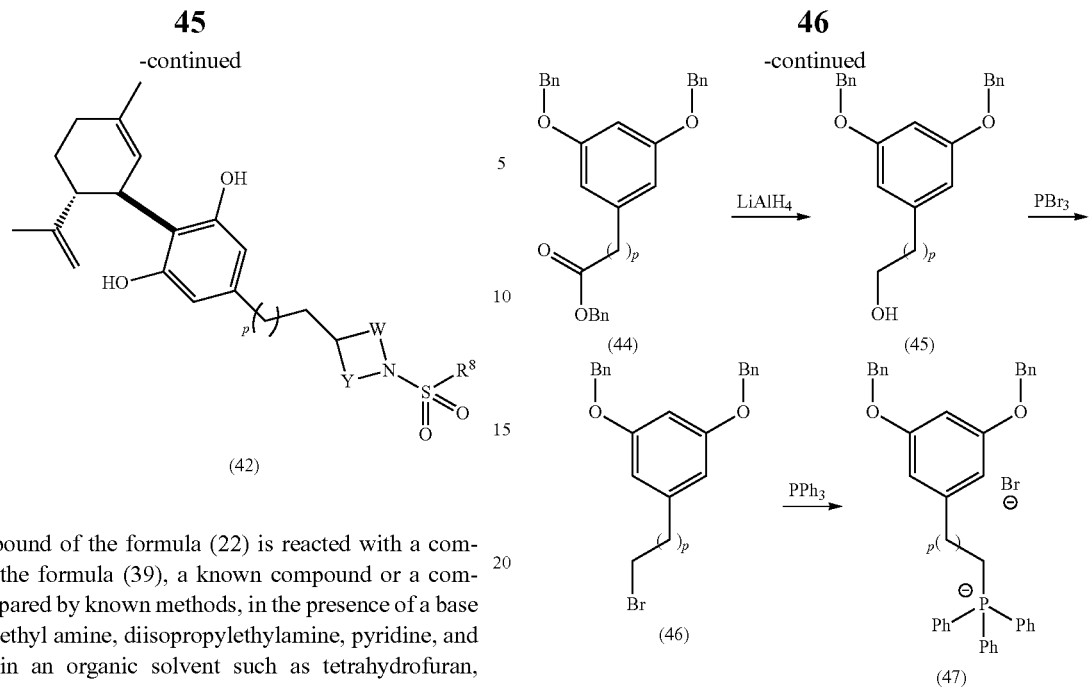

(42)

A compound of the formula (22) is reacted with a compound of the formula (39), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (40). A compound of the formula (40) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (41). Alternatively, a compound of the formula (40) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (41). A compound of the formula (41) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (42).

A compound of the formula (43) wherein p is 0, 1, or 2 is reacted with benzyl chloride in an organic solvent such as tetrahydrofuran, 1,4-dioxane, dichloromethane, chloroform, 1,2-dichloroethane, benzene, toluene, N,N-dimethylformamide, and the like, in the presence of a base such as potassium carbonate, sodium carbonate, lithium carbonate, sodium bicarbonate, potassium bicarbonate, lithium bicarbonate, and the like, optionally with heating, optionally with microwave irradiation to provide a compound of the formula (44). A compound of the formula (44) is then reacted with a reducing agent such as lithium aluminum hydride, lithium borohydride, sodium borohydride, sodium cyanoborohydride, and the like in an organic solvent such as tetrahydrofuran, 1,4-dioxane, dichloromethane, chloroform, 1,2-dichloro ethane, benzene, toluene, N,N-dimethylformamide, and the like to provide a compound of the formula (45). A compound of the formula (45) is then reacted with phosphorous tribromide in an organic solvent such as acetonitrile, tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (46). A compound of the formula (46) is then reacted with triphenyl phosphine in an organic solvent such as acetonitrile, tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (47).

Scheme 15

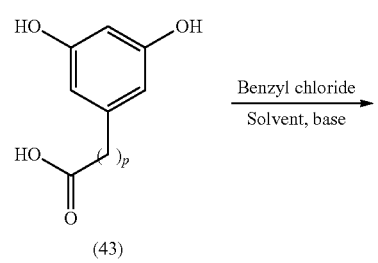

(43)

Scheme 16

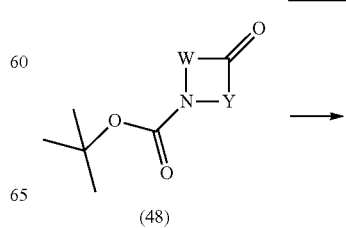

(48)

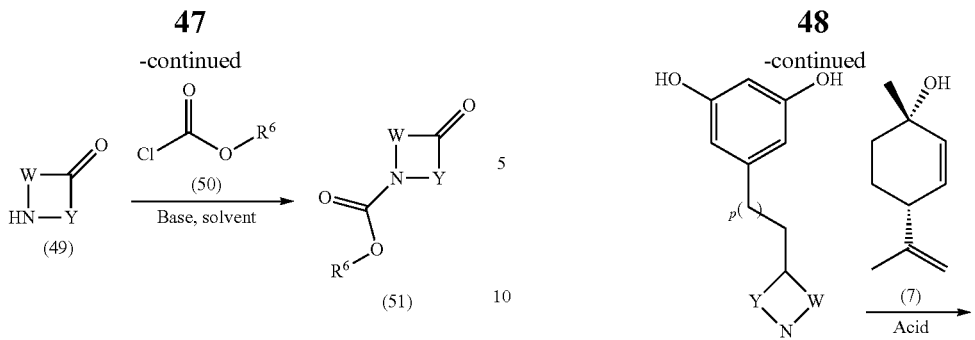

A compound of the formula (48), a known compound or a compound prepared by known means, is reacted with an acid such as trifluoroacetic acid, hydrochloric acid, sulfuric acid, and the like, in an organic solvent such as acetonitrile, tetrahydrofuran, 1,4-dioxane, dichloromethane, chloroform, 1,2-dichloroethane, methanol, ethanol, N,N-dimethylformamide, and the like, to provide a compound of the formula (49). A compound of the formula (49) is then reacted with a compound of the formula (50), in an organic solvent such as tetrahydrofuran, 1,4-dioxane, dichloromethane, chloroform, 1,2-dichloroethane, benzene, toluene, N,N-dimethylformamide, and the like, optionally in the presence of a base such as potassium carbonate, sodium carbonate, lithium carbonate, sodium bicarbonate, potassium bicarbonate, lithium bicarbonate, and the like, optionally with heating, optionally with microwave irradiation to provide a compound of the formula (51).

Scheme 17

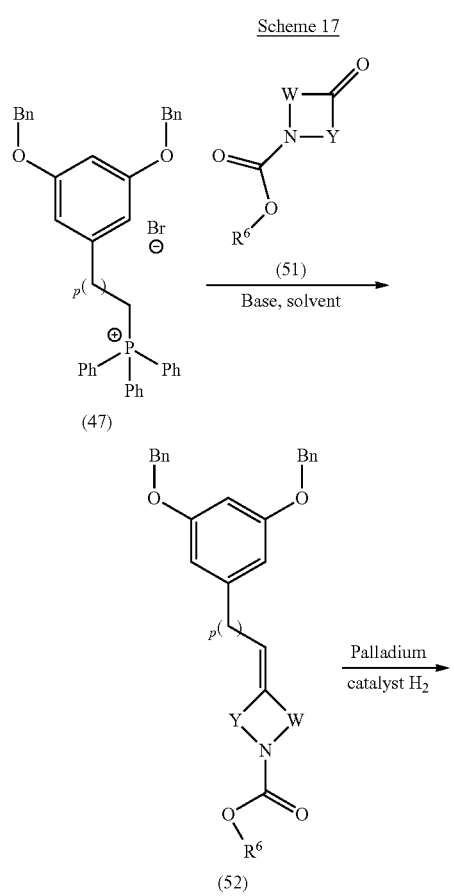

A compound of the formula (47) is reacted with a compound of the formula (51) in the presence of a base such as n-butyl lithium, sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (52). A compound of the formula (52) is reacted with hydrogen in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (53). A compound of the formula (53) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (54).

Scheme 18

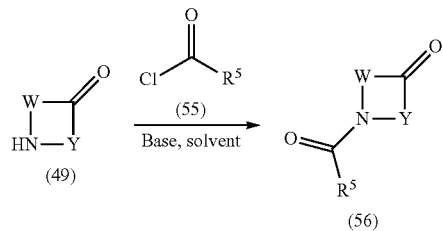

A compound of the formula (49) is reacted with a compound of the formula (55), in an organic solvent such as tetrahydrofuran, 1,4-dioxane, dichloromethane, chloroform, 1,2-dichloroethane, benzene, toluene, N,N-dimethylformamide, and the like, optionally in the presence of a base such as potassium carbonate, sodium carbonate, lithium carbonate, sodium bicarbonate, potassium bicarbonate, lithium bicarbonate, and the like, optionally with heating, optionally with microwave irradiation to provide a compound of the formula (56).

Scheme 19

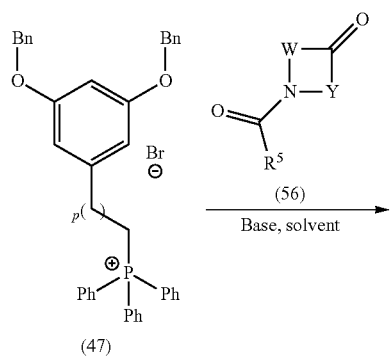

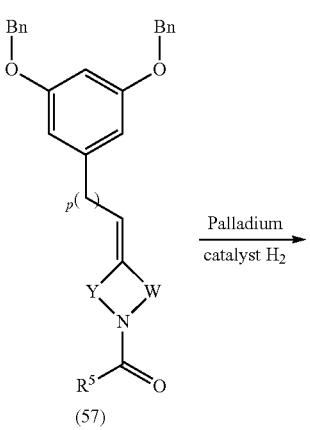

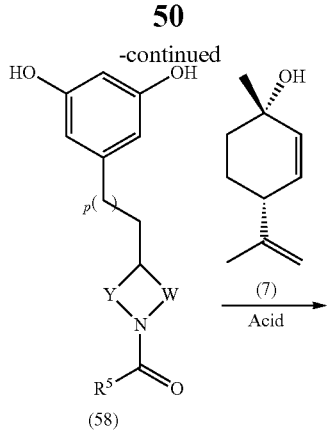

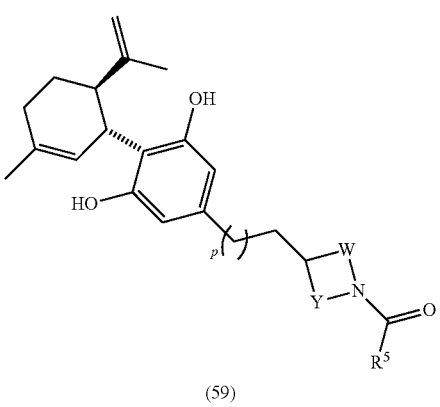

A compound of the formula (56) is reacted with a compound of the formula (47) in the presence of a base such as n-butyl lithium, sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (57). A compound of the formula (57) is reacted with hydrogen in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (58). A compound of the formula (58) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (59).

Scheme 20

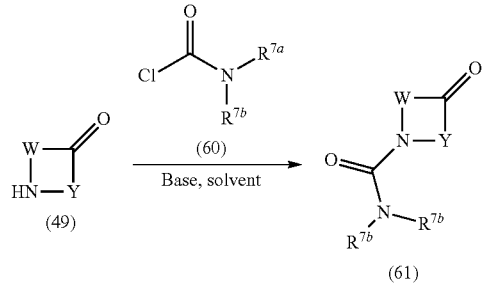

A compound of the formula (49) is reacted with a compound of the formula (60), in an organic solvent such as tetrahydrofuran, 1,4-dioxane, dichloromethane, chloroform, 1,2-dichloroethane, benzene, toluene, N,N-dimethylformamide, and the like, optionally in the presence of a base such as potassium carbonate, sodium carbonate, lithium carbonate, sodium bicarbonate, potassium bicarbonate, lithium bicarbonate, and the like, optionally with heating, optionally with microwave irradiation to provide a compound of the formula (61).

Scheme 21

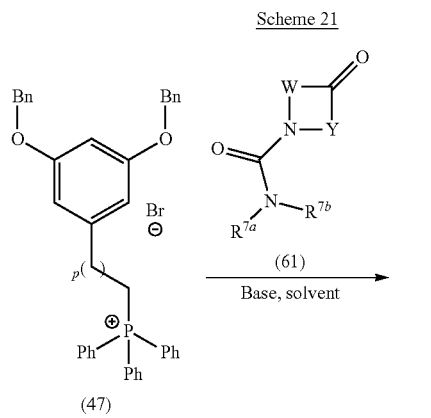

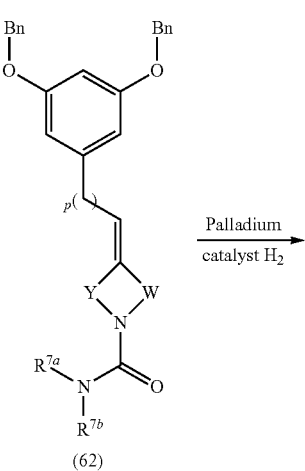

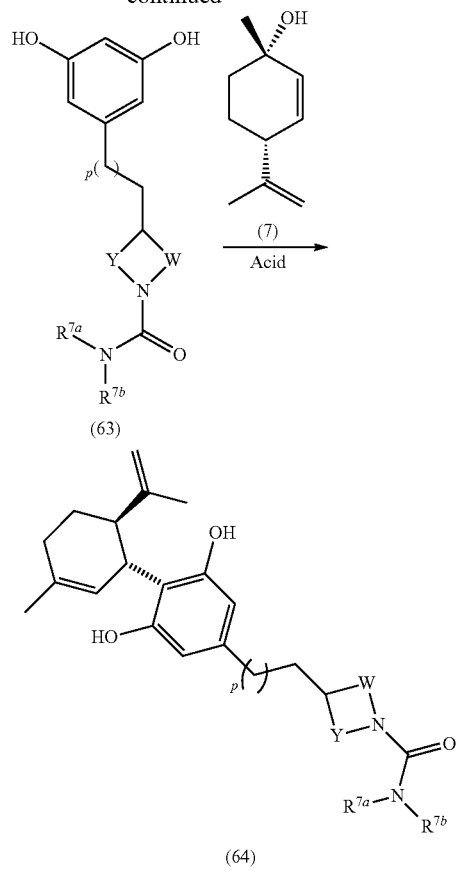

A compound of the formula (61) is reacted with a compound of the formula (47) in the presence of a base such as n-butyl lithium, sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (62). A compound of the formula (62) is reacted with hydrogen in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (63). A compound of the formula (63) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (64).

Scheme 22

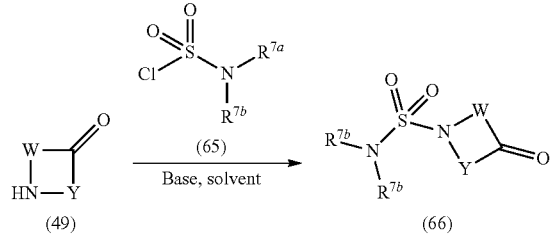

A compound of the formula (49) is reacted with a compound of the formula (65), in an organic solvent such as tetrahydrofuran, 1,4-dioxane, dichloromethane, chloroform, 1,2-dichloroethane, benzene, toluene, N,N-dimethylformamide, and the like, optionally in the presence of a base such as potassium carbonate, sodium carbonate, lithium carbonate, sodium bicarbonate, potassium bicarbonate, lithium bicarbonate, and the like, optionally with heating, optionally with microwave irradiation to provide a compound of the formula (66).

Scheme 23

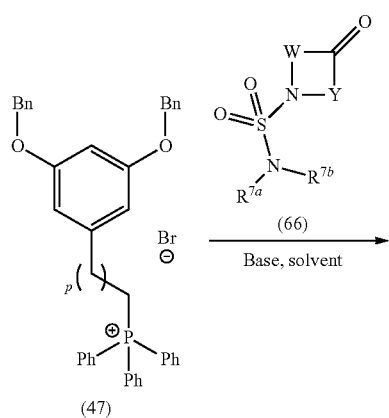

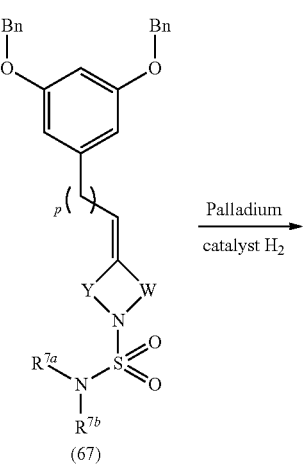

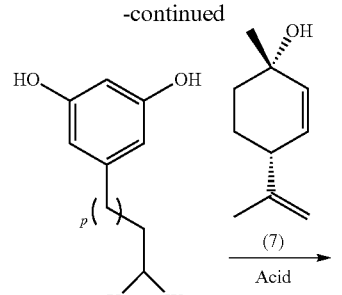

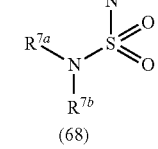

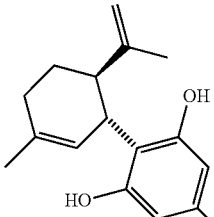

A compound of the formula (66) is reacted with a compound of the formula (47) in the presence of a base such as n-butyl lithium, sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (67). A compound of the formula (67) is reacted with hydrogen in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (68). A compound of the formula (68) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (69).

Scheme 24

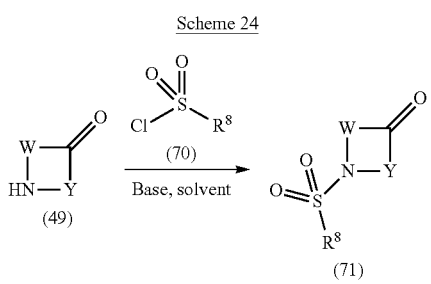

A compound of the formula (49) is reacted with a compound of the formula (70), in an organic solvent such as tetrahydrofuran, 1,4-dioxane, dichloromethane, chloroform, 1,2-dichloroethane, benzene, toluene, N,N-dimethylformamide, and the like, optionally in the presence of a base such as potassium carbonate, sodium carbonate, lithium carbonate, sodium bicarbonate, potassium bicarbonate, lithium bicarbonate, and the like, optionally with heating, optionally with microwave irradiation to provide a compound of the formula (71).

Scheme 25

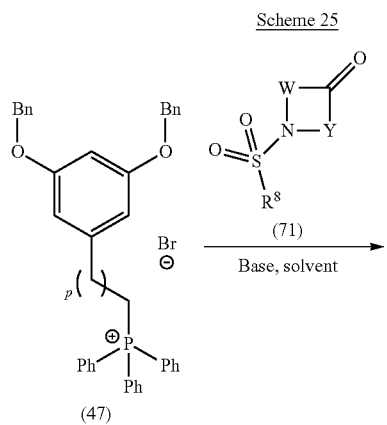

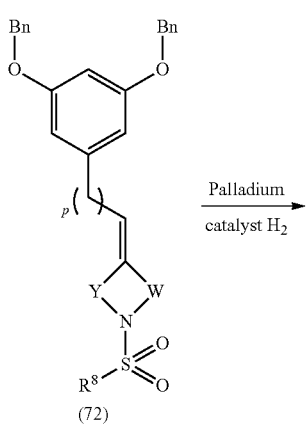

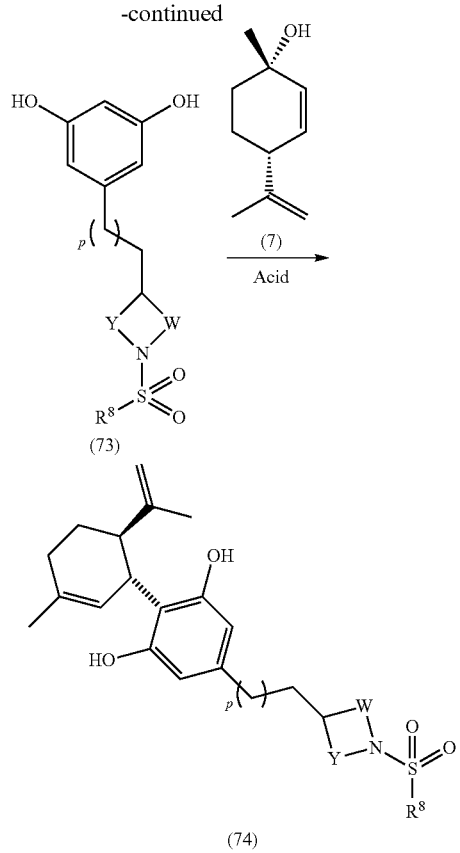

A compound of the formula (71) is reacted with a compound of the formula (47) in the presence of a base such as n-butyl lithium, sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (72). A compound of the formula (72) is reacted with hydrogen in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis (acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (73). A compound of the formula (73) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (74).

Scheme 26

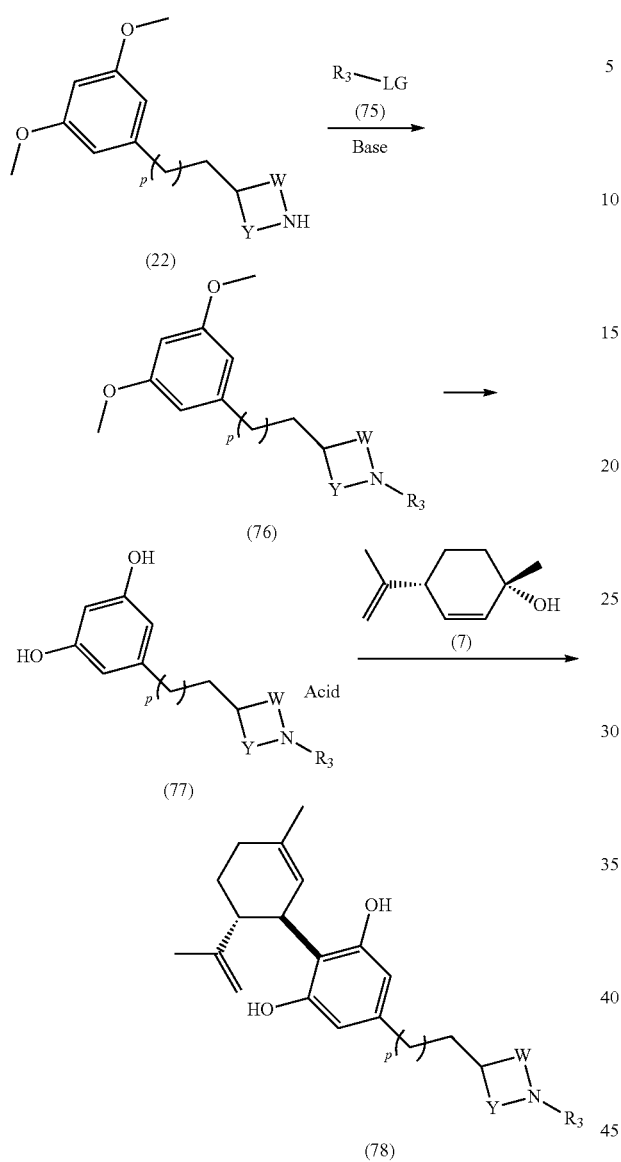

furan, 1,4-dioxane, dichloromethane, chloroform, 1,2-dichloroethane, N,N-dimethylformamide, and the like, optionally with heating, optionally with microwave irradiation to provide a compound of the formula (77). A compound of the formula (77) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (78).

Scheme 27

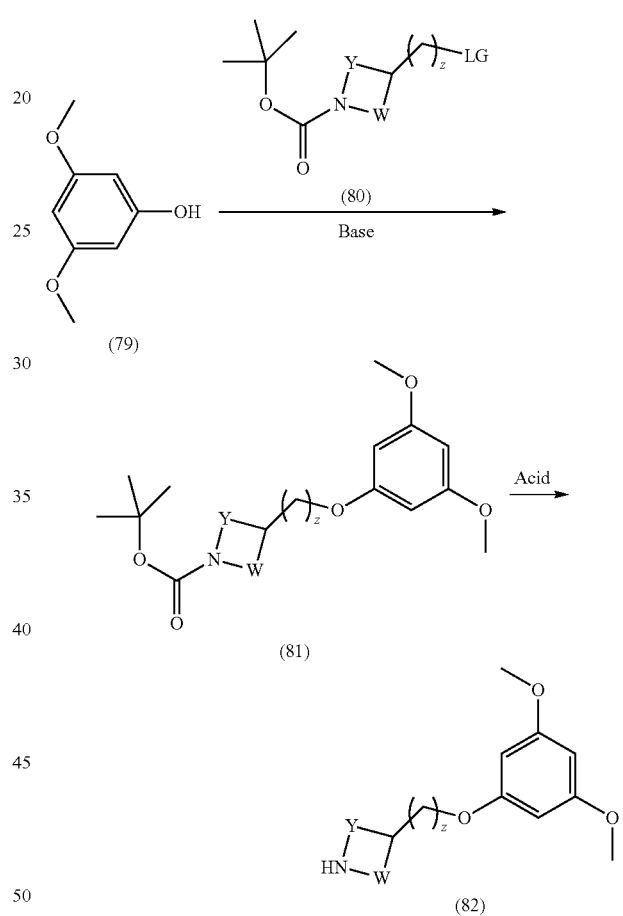

A compound of the formula (22) is reacted with a compound of the formula (75), a known compound or a compound prepared by known methods, wherein $R^3$ is an optionally substituted heteroaryl and wherein LG is a leaving group such as iodine, bromine, methanesulfonate, tosylate and the like in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (76). A compound of the formula (76) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (77). Alternatively, a compound of the formula (76) is reacted with hydrogen bromide in acetic acid, optionally in an organic solvent such as tetrahydro- A compound of the formula (79) is reacted with a compound of the formula (80), a known compound or compound prepared by known methods, wherein LG is a leaving group such as iodine, bromine, methanesulfonate, tosylate and the like, in the presence of a base such as sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (81). A compound of the formula (81) is then reacted with an acid such as hydrochloric acid, sulfuric acid, trifluoroacetic acid, and the like, in an organic solvent such as methanol, ethanol, tetrahydrofuran, 1,4-dioxane, dichloromethane, chloroform, 1,2-dichloroethane, N,N-dimethylformamide, and the like, to provide a compound of the formula (82)

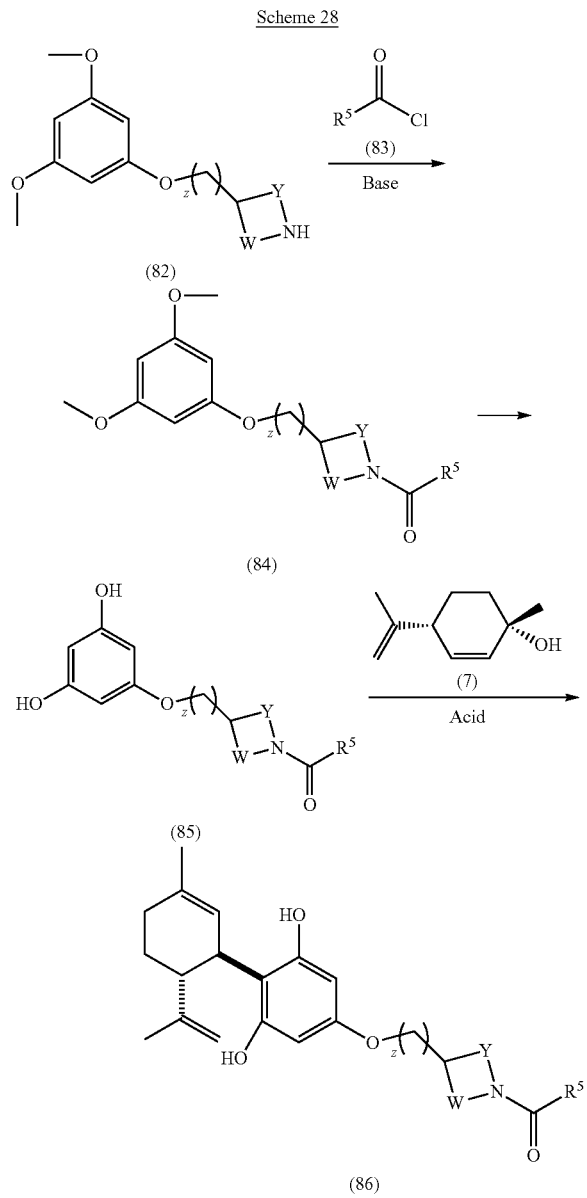

A compound of the formula (82) is reacted with a compound of the formula (83), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (84). A compound of the formula (84) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (85).

Alternatively, a compound of the formula (84) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (85). A compound of the formula (85) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (86).

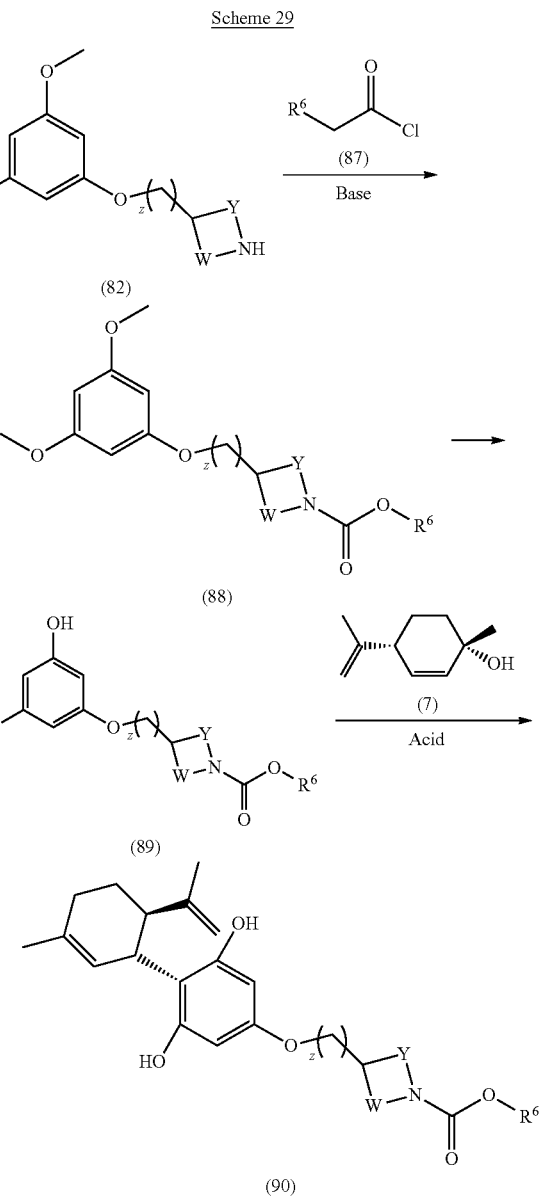

A compound of the formula (82) is reacted with a compound of the formula (87), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (88). A compound of the formula (88) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (89). Alternatively, a compound of the formula (88) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (89). A compound of the formula (89) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (90).

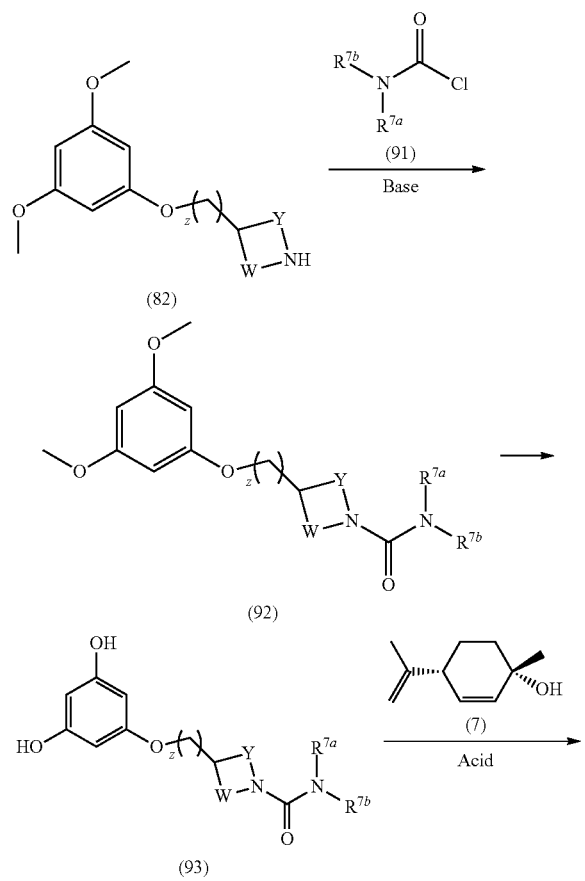

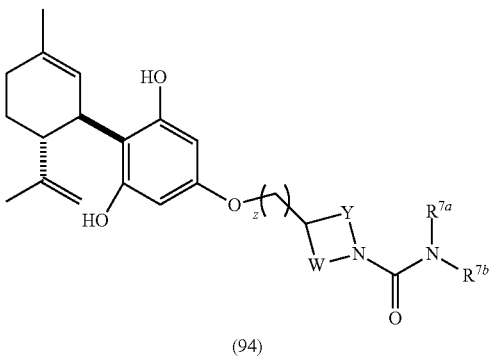

A compound of the formula (82) is reacted with a compound of the formula (91), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (92). A compound of the formula (92) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (93). Alternatively, a compound of the formula (92) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (93). A compound of the formula (93) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (94).

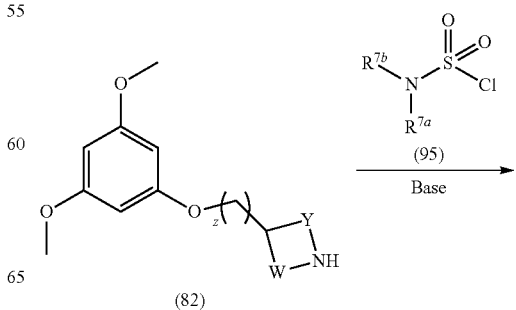

Scheme 32

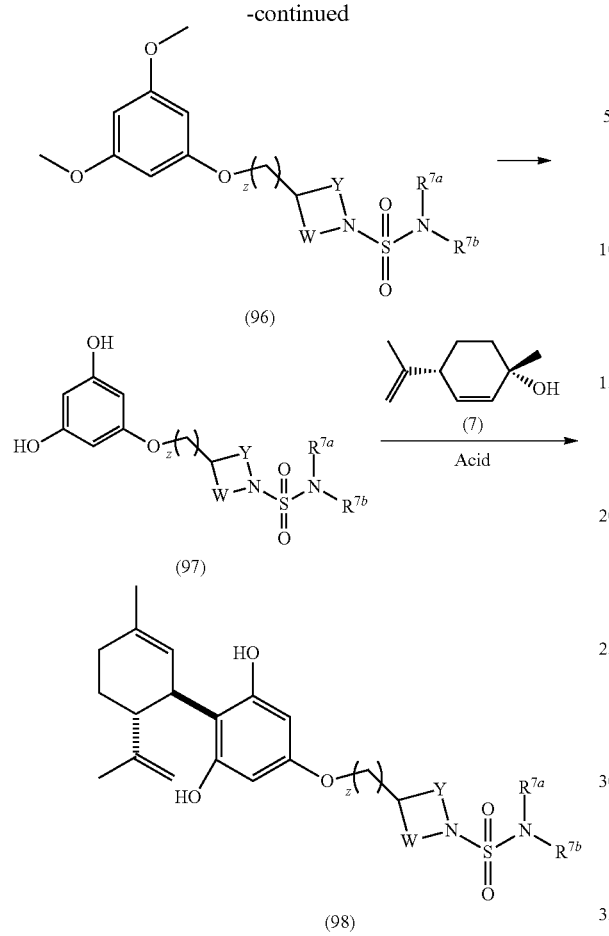

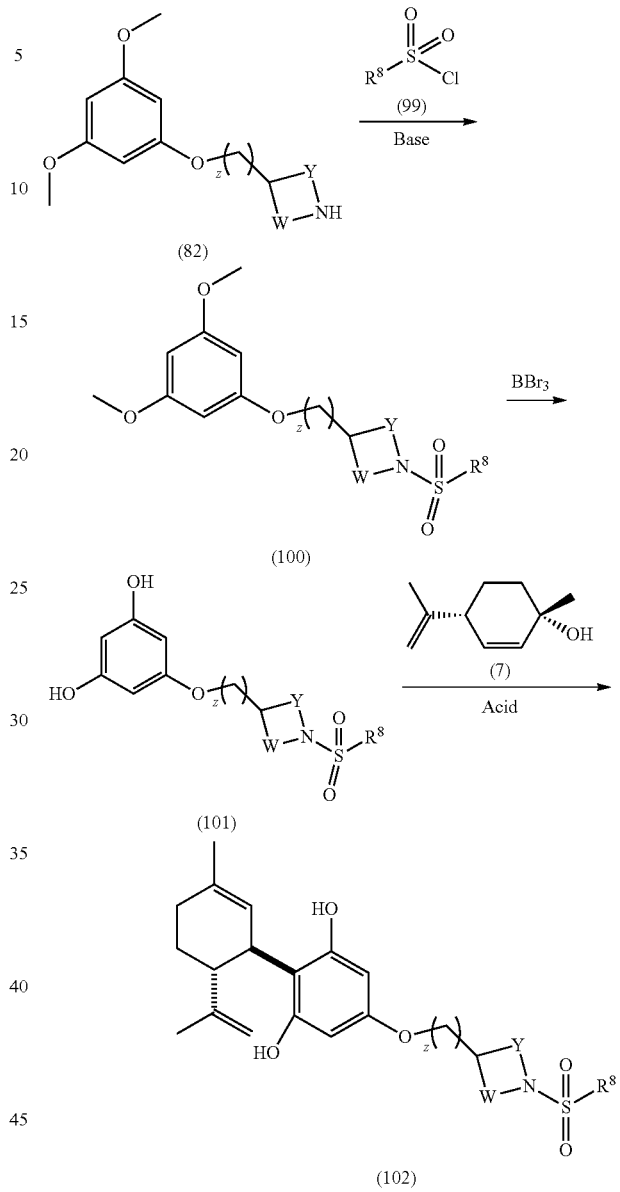

A compound of the formula (82) is reacted with a compound of the formula (95), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (96). A compound of the formula (96) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (97). Alternatively, a compound of the formula (96) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (97). A compound of the formula (97) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (98).

A compound of the formula (82) is reacted with a compound of the formula (99), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (100). A compound of the formula (100) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (101). A compound of the formula (101) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (102).

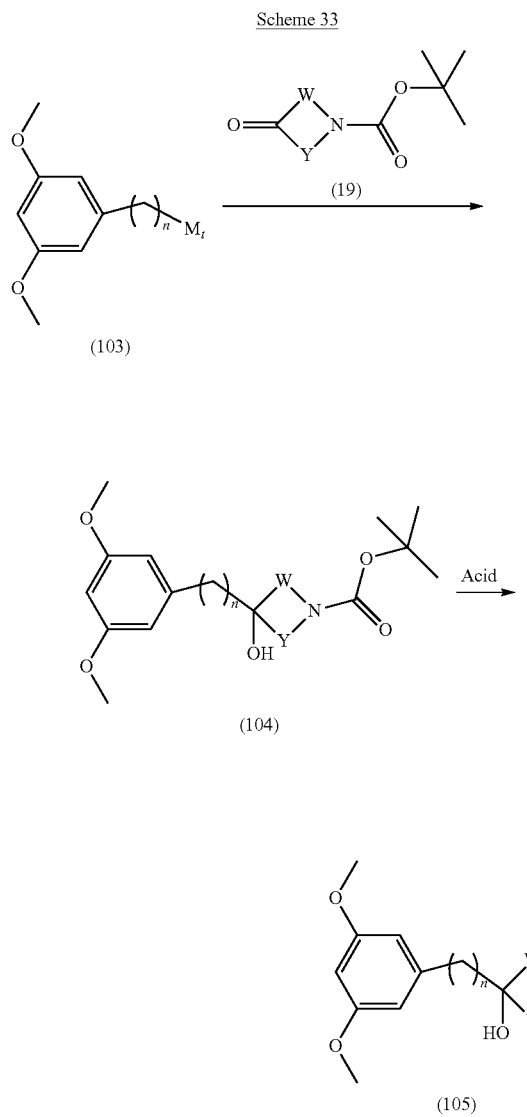

(103)

(104)

(105)

Scheme 33

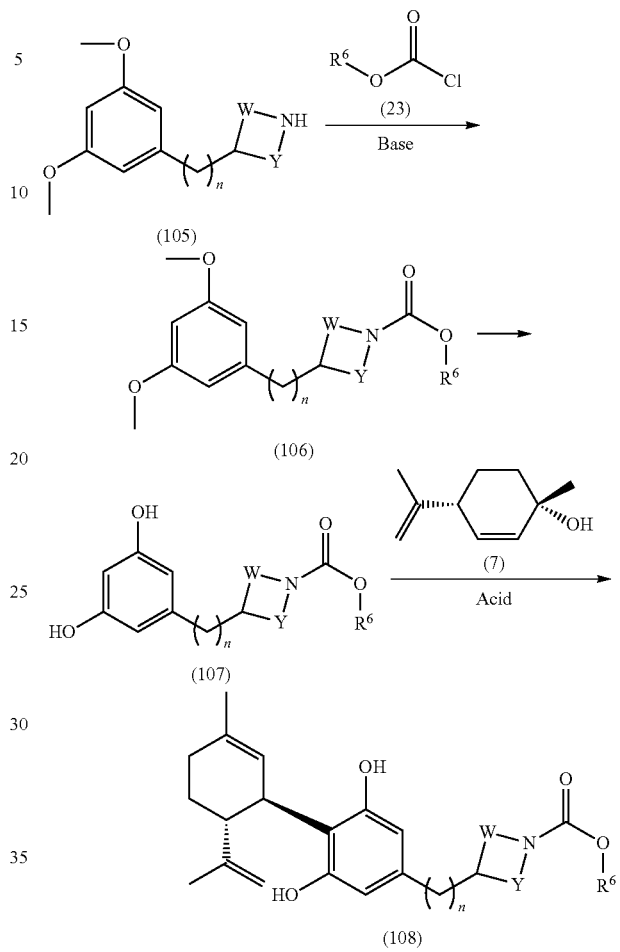

Scheme 35

(105)

(106)

(107)

(108)

A compound of the formula (103), a known compound or a compound prepared by known methods where in $M_t$ is a metal salt such as MgCl, MgBr, ZnCl, Li, and the like, is reacted with a compound of the formula (19), a known compound or compound prepared by known methods, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (104). A compound of the formula (104) is then reacted with an acid such as hydrochloric acid, sulfuric acid, trifluoroacetic acid, and the like, in an organic solvent such as methanol, ethanol, tetrahydrofuran, 1,4-dioxane, dichloromethane, chloroform, 1,2-dichloroethane, N,N-dimethylformamide, and the like, to provide a compound of the formula (105).

A compound of the formula (105) is reacted with a compound of the formula (23), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (106). A compound of the formula (106) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (107). Alternatively, a compound of the formula (106) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (107). A compound of the formula (107) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (108).

Scheme 36

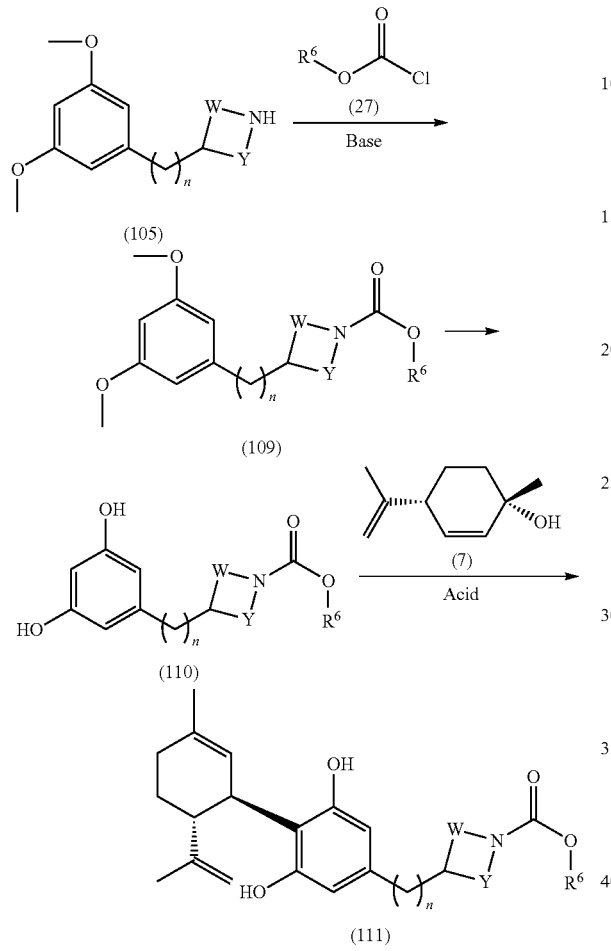

p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (111).

Scheme 37

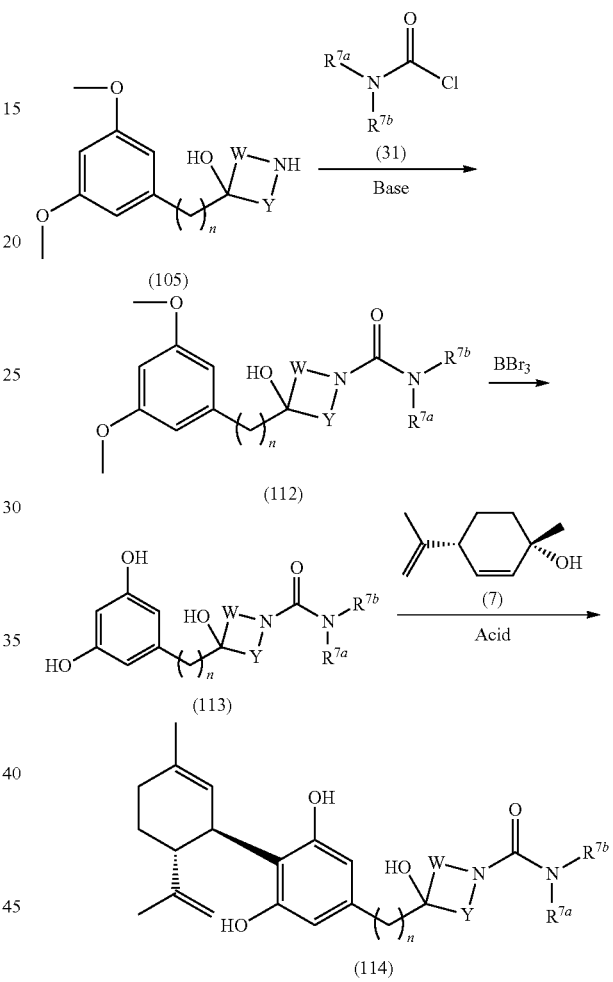

A compound of the formula (105) is reacted with a compound of the formula (27), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (109). A compound of the formula (109) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (110). Alternatively, a compound of the formula (109) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (110). A compound of the formula (110) is then reacted with a compound of the formula (7) optionally in the presence of an acid such as A compound of the formula (105) is reacted with a compound of the formula (31), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (112). A compound of the formula (112) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (113). A compound of the formula (113) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (114).

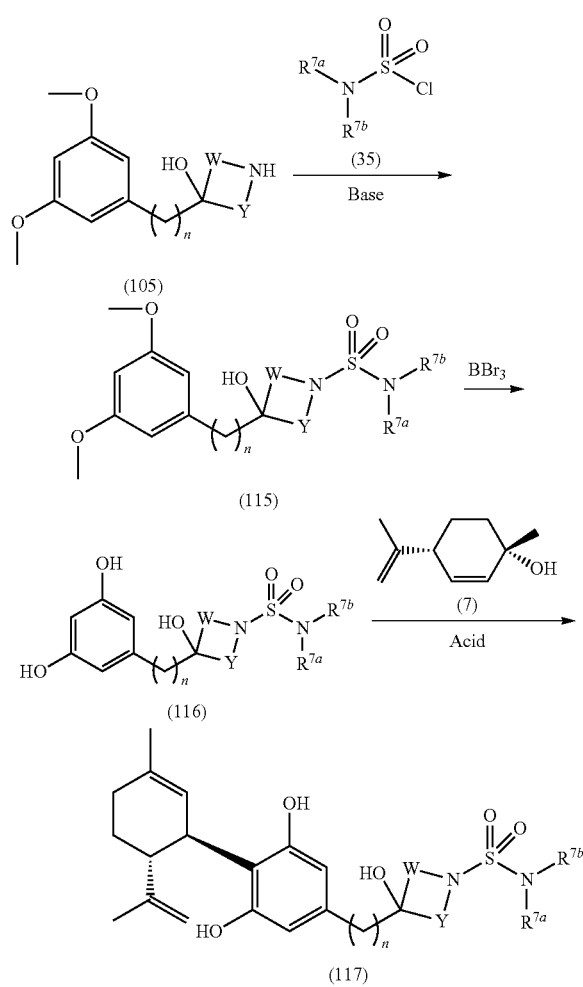

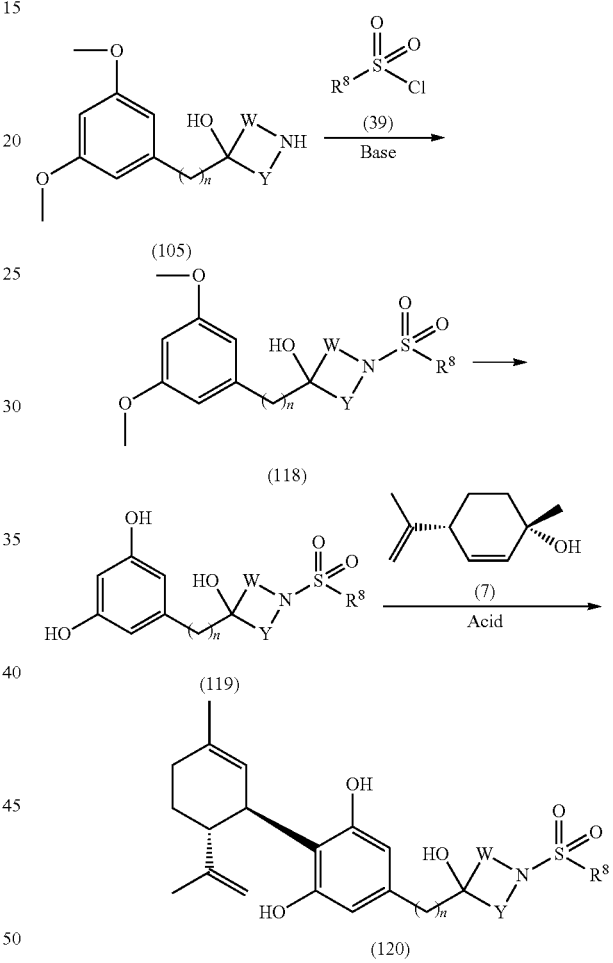

A compound of the formula (105) is reacted with a compound of the formula (35), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (115). A compound of the formula (115) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (116). Alternatively, a compound of the formula (115) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (116). A compound of the formula (116) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (117).

A compound of the formula (105) is reacted with a compound of the formula (39), a known compound or a compound prepared by known methods, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (118). A compound of the formula (118) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (119). Alternatively, a compound of the formula (118) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (119). A compound of the formula (119) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (120).

(121) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (122). Alternatively, a compound of the formula (121) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (122). A compound of the formula (122) is then reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (123).

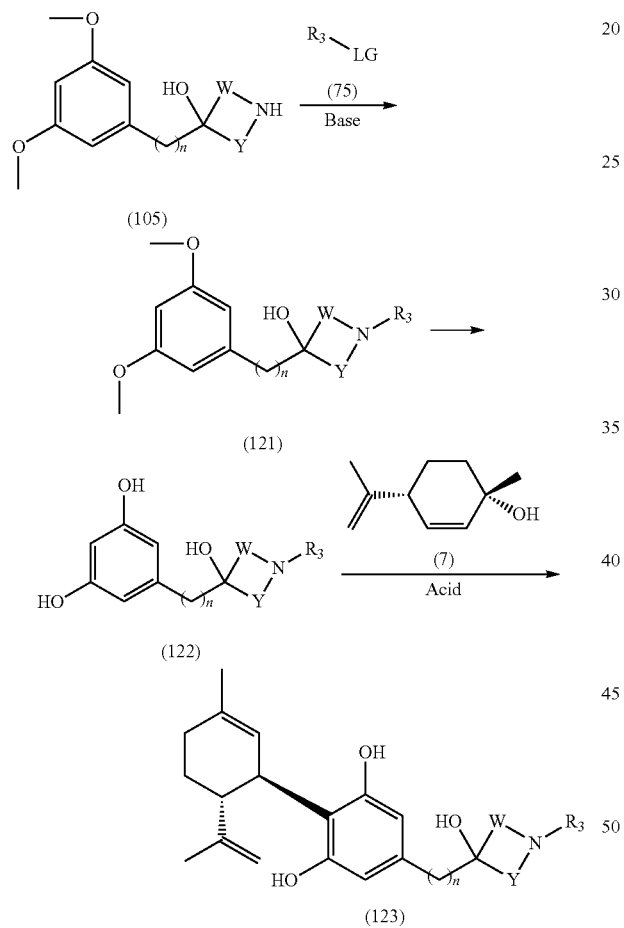

Scheme 40

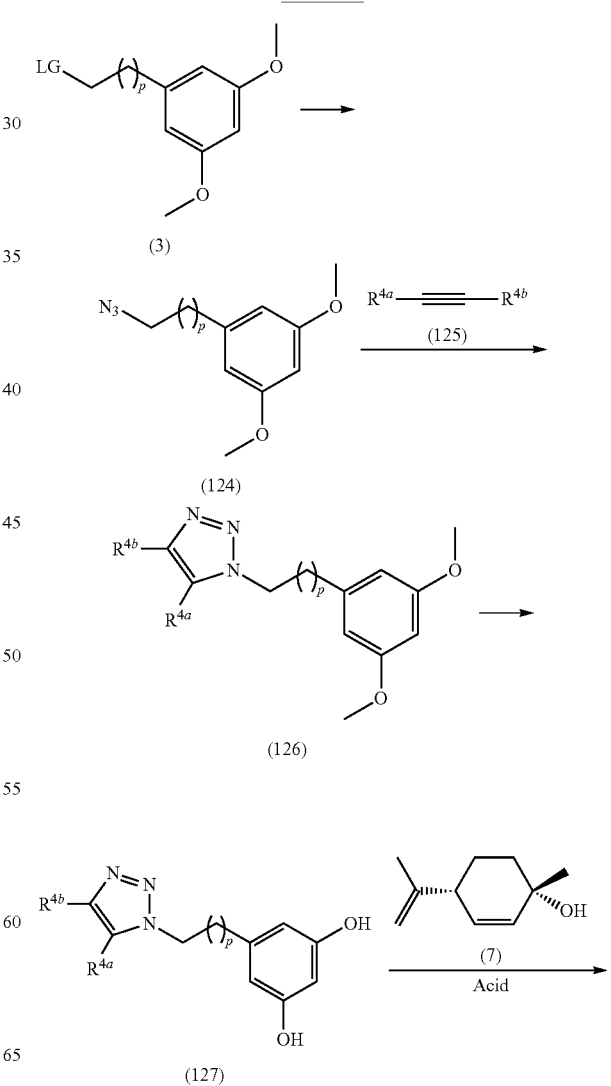

Scheme 41

A compound of the formula (105) is reacted with a compound of the formula (75), a known compound or a compound prepared by known methods, wherein $R^3$ is an optionally substituted heteroaryl and wherein LG is a leaving group such as iodine, bromine, methanesulfonate, tosylate and the like in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (121). A compound of the formula

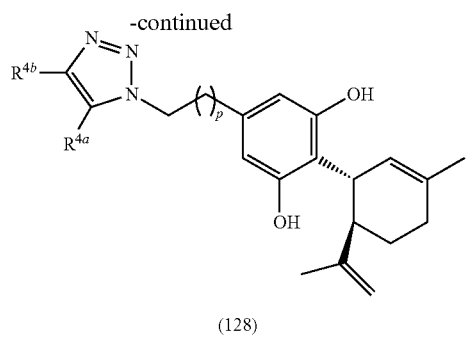

(128)

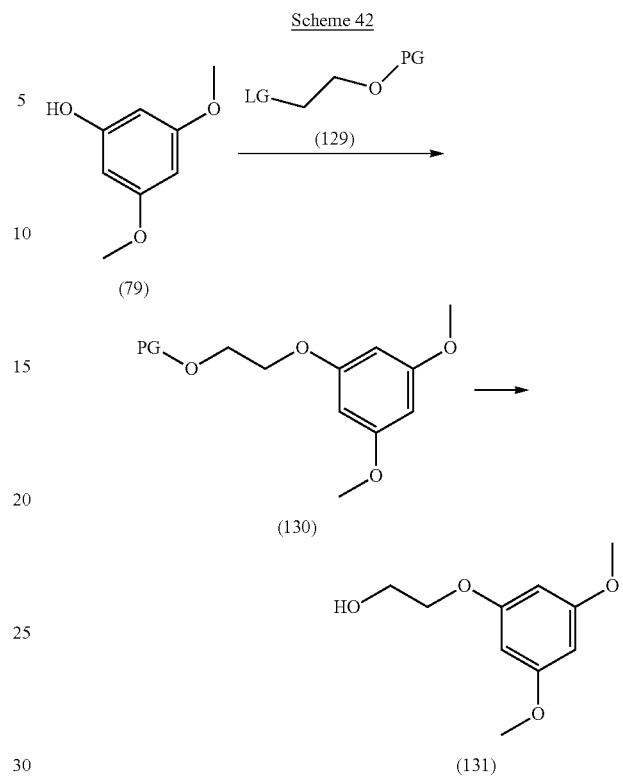

Scheme 42

A compound of the formula (3) wherein p is 0, 1, or 2 is reacted with an azide salt such as sodium azide, lithium azide, potassium azide, tetramethylammonium azide and the like, in an organic solvent such as tetrahydrofuran, 1,4-dioxane, methanol, ethanol, isopropanol, dichloromethane, chloroform, 1,2-dichloroethane, N,N-dimethylformamide, and the like, optionally with heating, optionally with microwave irradiation to provide a compound of the formula (124). A compound of the formula (124) is then reacted with an acetylene (125) optionally in the presence of a copper (I) salt such as copper (I) bromide, copper (I) chloride, copper (I) iodide, and the like, optionally in the presence of a ruthenium catalyst such as Benzeneruthenium(II) chloride, Bis(2,2'-bipyridine)-(5-aminophenanthroline)ruthenium bis (hexafluorophosphate), Bis(cyclopentadienyl)ruthenium(II), Bis(cyclopentadienylruthenium dicarbonyl) dimer, Carbonyldihydridotris(triphenylphosphine) ruthenium(II), Chloropentaammineruthenium(II) chloride, cis-Dichlorobis(2,2'-bipyridine)ruthenium(II), Dichlorotetrakis (triphenylphosphine)ruthenium(II), and the like in an organic solvent such as methanol, ethanol, tetrahydrofuran, 1,4-dioxane, dichloromethane, chloroform, 1,2-dichloroethane, N,N-dimethylformamide, and the like, to provide a compound of the formula (126). A compound of the formula (126) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (127). Alternatively, a compound of the formula (126) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (127). A compound of the formula (127) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (128).

A compound of the formula (79) is reacted with a compound of the formula (129), a known compound or a compound prepared by known methods, wherein LG is a leaving group such as chlorine, bromine, iodine, methanesulfonate, trifluoromethanesulfonate, toluenesulfonate, and the like and PG is a protecting group such as tert-butyloxycarbonyl, carbobenzyloxy, and the like, optionally in the presence of a base such as a base such as sodium hydride, potassium hydride, potassium carbonate, sodium carbonate, lithium carbonate, sodium bicarbonate, potassium bicarbonate, lithium bicarbonate, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (130). The protecting group of a compound of the formula (130) is then removed by reacting the compound of the formula (130) with an acid such as hydrogen chloride, trifluoroacetic acid, and the like in organic solvent such as tetrahydrofuran, 1,4-dioxane, dichloromethane, chloroform, 1,2-dichloroethane, N,N-dimethylformamide, and the like, to provide a compound of the formula (131). Alternatively, the protecting group of a compound of the formula (130) is then removed by reacting the compound of the formula (130) with hydrogen in the presence of a catalyst such as palladium on activated carbon, platinum oxide and the like in an organic solvent such as ethyl acetate, methanol, ethanol, tetrahydrofuran, 1,4-dioxane, and the like to provide a compound of the formula (131). Alternatively, the protecting group of a compound of the formula (130) is then removed by reacting the compound of the formula (130) with a base such as sodium hydroxide, potassium carbonate and the like, in a solvent like water, methanol, tetrahydrofuran 1,4-dioxane, dimethylformamide, and the like to provide a compound of the formula (131).

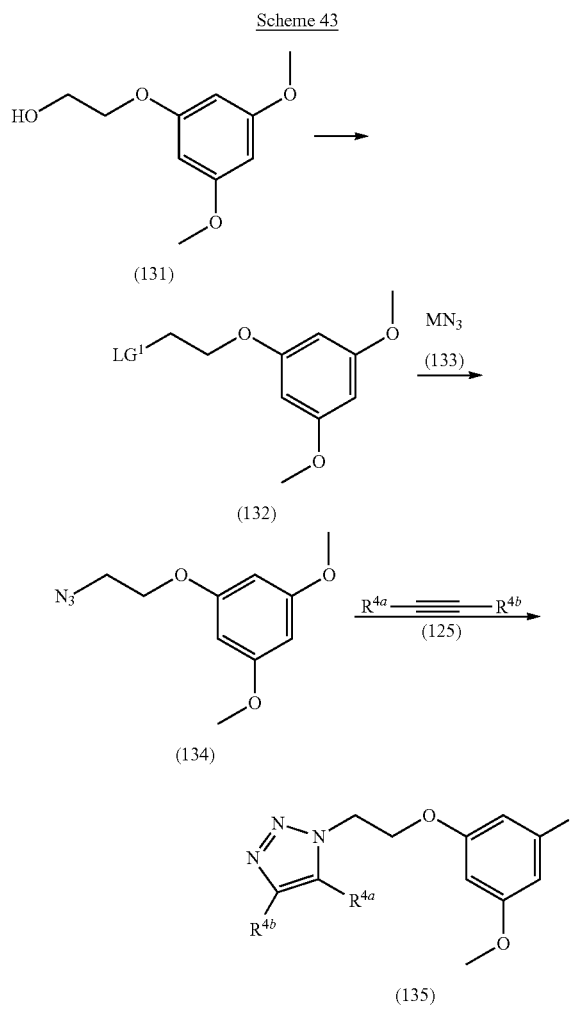

A compound of the formula (131) is then converted to a compound of the formula (132) wherein $LG^1$ is a leaving group such as methanesulfonate, trifluoromethanesulfonate, toluenesulfonate, and the like by reacting a compound of the formula (131) with a corresponding sulfonyl chloride such as methanesulfonyl chloride, trifluoromethanesulfonyl chloride, toluenesulfonyl chloride, and the like, in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (132). A compound of the formula (132) is then reacted with a compound of the formula (133) wherein M is a counterion such as sodium, lithium, potassium, tetramethylammonium, and the like, in an organic solvent such as tetrahydrofuran, 1,4-dioxane, methanol, ethanol, isopropanol, dichloromethane, chloroform, 1,2-dichloroethane, N,N-dimethylformamide, and the like, optionally with heating, optionally with microwave irradiation to provide a compound of the formula (134).

A compound of the formula (134) is then reacted with an acetylene (125) optionally in the presence of a copper (I) salt such as copper (I) bromide, copper (I) chloride, copper (I) iodide, and the like, optionally in the presence of a ruthenium catalyst such as Benzeneruthenium(II) chloride, Bis (2,2'-bipyridine)-(5-aminophenanthroline)ruthenium bis (hexafluorophosphate), Bis(cyclopentadienyl) ruthenium (II), Bis(cyclopentadienylruthenium dicarbonyl) dimer, Carbonyldihydridotris (triphenylphosphine) ruthenium(II), Chloropentaammineruthenium(II) chloride, cis -Dichlorobis (2,2'-bipyridine)ruthenium(II), Dichlorotetrakis(triphenylphosphine)ruthenium(II), and the like in an organic solvent such as methanol, ethanol, tetrahydrofuran, 1,4-dioxane, dichloromethane, chloroform, 1,2-dichloroethane, N,N-dimethylformamide, and the like, to provide a compound of the formula (135).

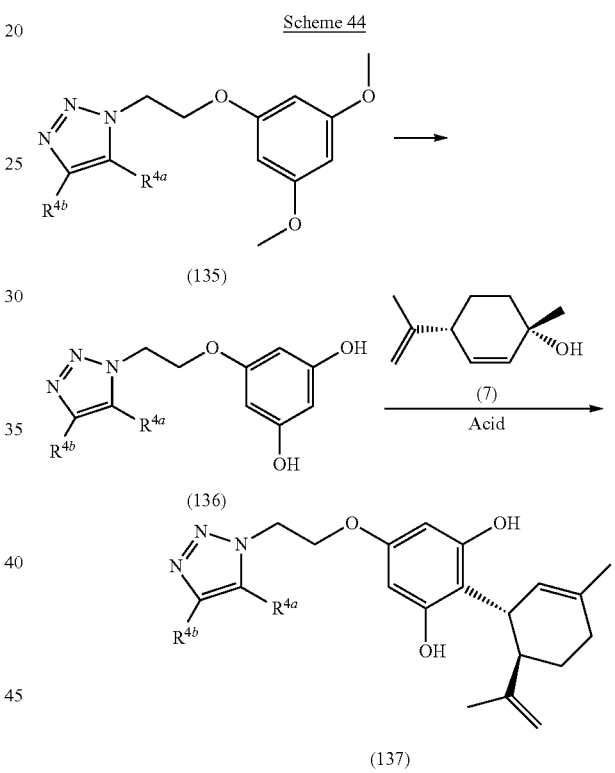

A compound of the formula (135) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (136). Alternatively, a compound of the formula (135) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (136). A compound of the formula (136) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (137).

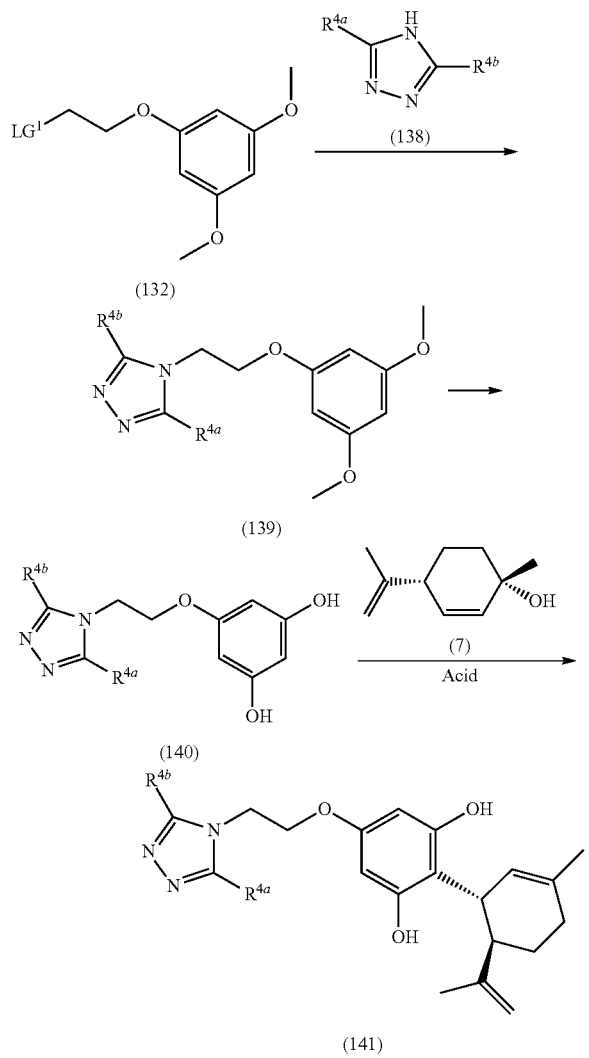

Scheme 44

A compound of the formula (132) is then reacted with a compound of the formula (138), a known compound or a compound prepared by known means, optionally in the presence of a base such as sodium hydride, potassium hydride, potassium carbonate, sodium carbonate, lithium carbonate, sodium bicarbonate, potassium bicarbonate, lithium bicarbonate, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (139). A compound of the formula (139) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (140). Alternatively, a compound of the formula (139) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (140). A compound of the formula (140) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (141).

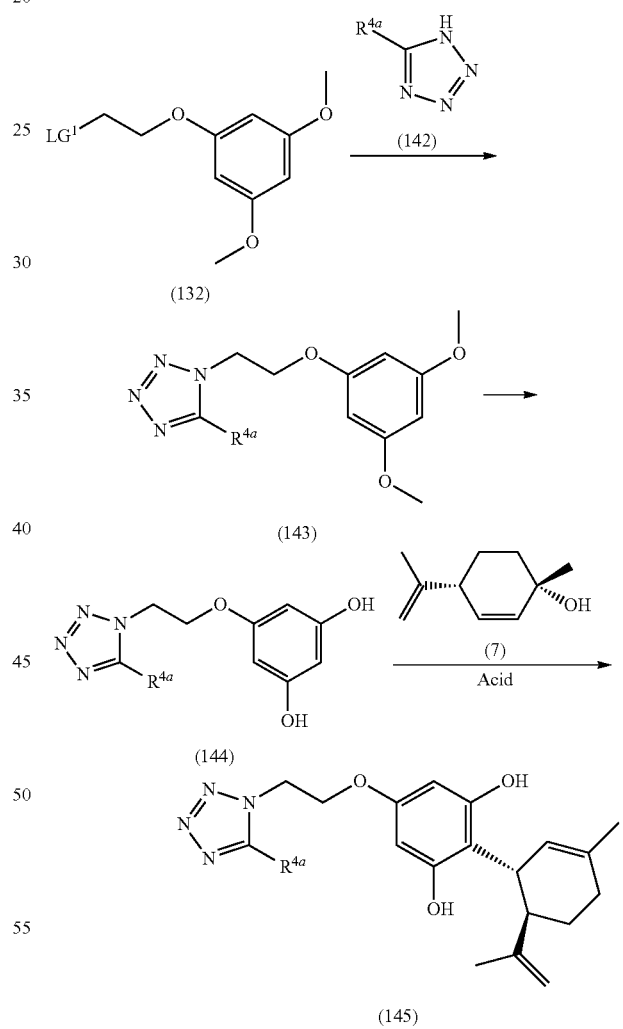

Scheme 45

A compound of the formula (132) is then reacted with a compound of the formula (142), a known compound or a compound prepared by known means, optionally in the presence of a base such as sodium hydride, potassium hydride, potassium carbonate, sodium carbonate, lithium carbonate, sodium bicarbonate, potassium bicarbonate, lithium bicarbonate, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (143). A compound of the formula (143) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (144). Alternatively, a compound of the formula (143) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (144). A compound of the formula (144) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (145).

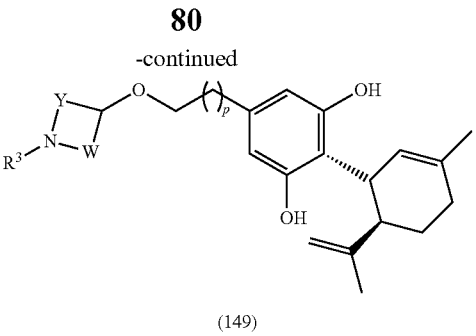

(149)

A compound of the formula (3) wherein p is 0, 1, or 2, is reacted with a compound of the formula (146), a known compound or a compound prepared by known methods, optionally in the presence of a base such as a base such as sodium hydride, potassium hydride, potassium carbonate, sodium carbonate, lithium carbonate, sodium bicarbonate, potassium bicarbonate, lithium bicarbonate, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (147). A compound of the formula (147) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (148). Alternatively, a compound of the formula (147) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (148). A compound of the formula (148) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (149).

Scheme 46

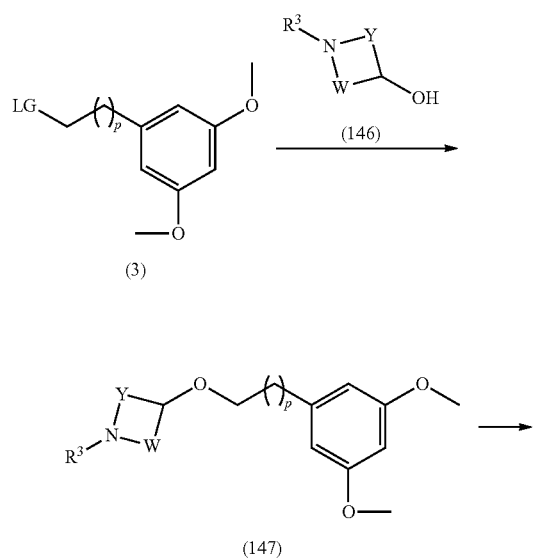

Scheme 47

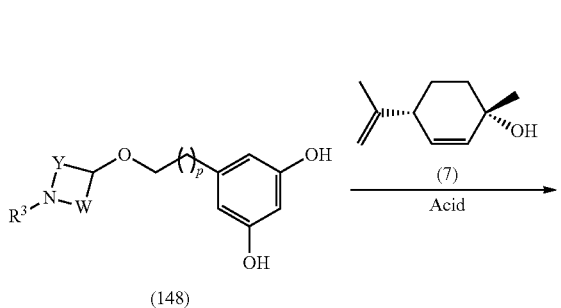

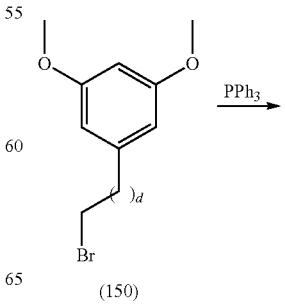

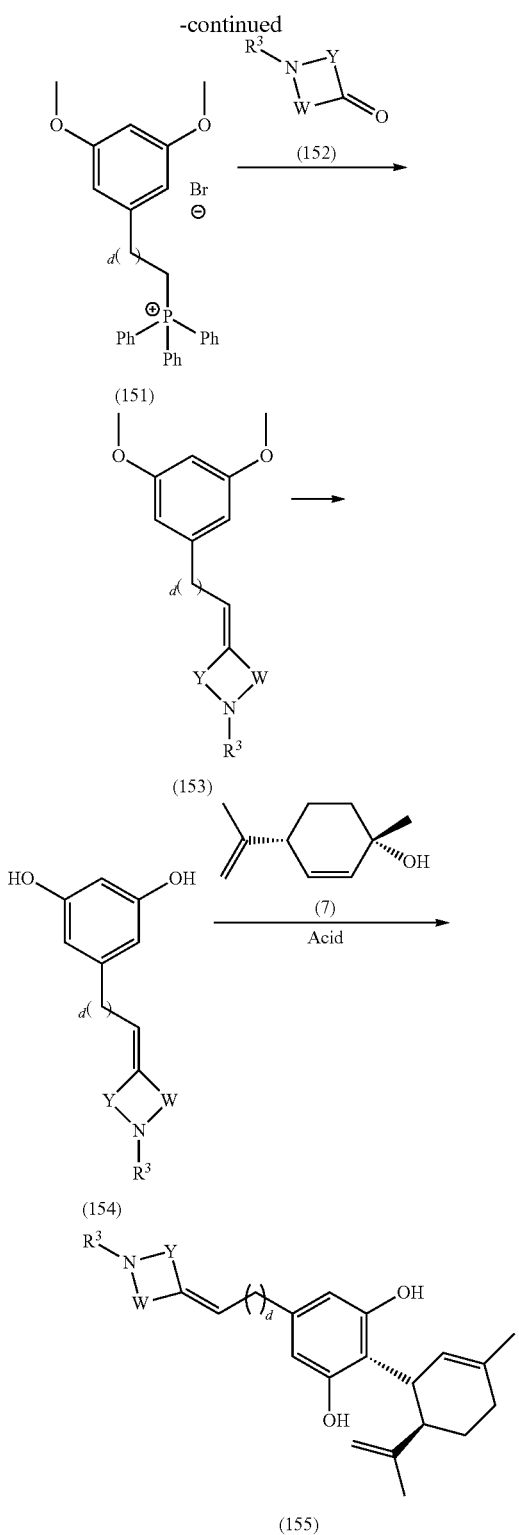

(151) is reacted with a compound of the formula (152), a known compound or a compound prepared by known means, in the presence of a base such as n-butyl lithium, sodium hydride, potassium hydride, lithium diisopropyl amide, potassium diisopropyl amide, sodium diisopropyl amide, lithium hexamethyldisilazide, potassium hexamethyldisilazide, sodium hexamethyldisilazide, and the like, in an organic solvent such as toluene, benzene, tetrahydrofuran, 1,4-dioxane, dichloromethane, chloroform, 1,2-dichloroethane, N,N-dimethylformamide, and the like, optionally with heating, optionally with microwave irradiation to provide a compound of the formula (153). A compound of the formula (153) is reacted with hydrogen bromide in acetic acid, optionally in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (154). Alternatively, a compound of the formula (153) is reacted with boron tribromide in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (154). A compound of the formula (154) is reacted with a compound of the formula (7) optionally in the presence of an acid such as p-toluenesulfonic acid, sulfuric acid, hydrochloric acid, and the like, optionally in the presence of boron trifluoride etherate, in an organic solvent such as tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (155).

Scheme 48

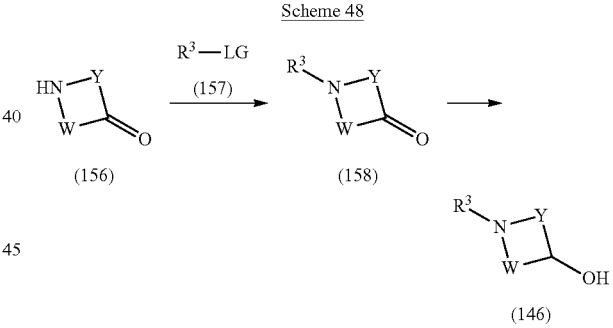

A compound of the formula (156), a known compound or a compound prepared by known means, is reacted with a compound of the formula (157), a known compound or a compound prepared by known means wherein LG is a leaving group such as chlorine, bromine, iodine, methanesulfonate, trifluoromethanesulfonate, toluenesulfonate, and the like, optionally in the presence of a base such as triethyl amine, diisopropylethylamine, pyridine, and the like, in an organic solvent such as tetrahydrofuran, 1,4-dioxane, dichloromethane, chloroform, 1,2-dichloroethane, N,N-dimethylformamide, and the like, optionally with heating, optionally with microwave irradiation to provide a compound of the formula (158). A compound of the formula (158) is then reacted with a reducing agent such as lithium aluminum hydride, sodium borohydride, sodium cyanoborohydride, lithium borohydride, and the like, in an organic solvent such as tetrahydrofuran, 1,4-dioxane, dichloromethane, chloroform, 1,2-dichloroethane, and the like, optionally A compound of the formula (150), a known compound or a compound prepared by known means, is reacted with triphenyl phosphine in an organic solvent such as acetonitrile, tetrahydrofuran, 1,4-dioxane, dichloromethane, chloroform, 1,2-dichloroethane, benzene, toluene, N,N-dimethylformamide, and the like, optionally with heating, optionally with microwave irradiation to provide a compound of the formula (151). A compound of the formula with heating, optionally with microwave irradiation to provide a compound of the formula (146).

The examples provided below provide representative methods for preparing exemplary compounds of the present invention. The skilled practitioner will know how to substitute the appropriate reagents, starting materials and purification methods known to those skilled in the art, in order to prepare the compounds of the present invention.

¹H-NMR spectra were obtained on a Varian Mercury 300-MHz NMR. Mass spectral data were determined with a Waters Alliance 2695 HPLC/MS (Waters Symmetry C18, 4.6×75 mm, 3.5 μm) with a 2996 diode array detector from 210-400 nm. Preparative HPLC purifications were performed using a Shimadzu LC-8A HPLC system equipped with a Phenomenex Luna 5μ C18(2), 100A, AXIA Packed, 250×21.2 mm HPLC column. Gradients elution using water and methanol over 30 minutes (66% water/methanol to 20% water in methanol) at a rate of 15 mL/minute were employed, and an UV detector set for 220 nM identified compounds for collection.

EXAMPLES

Examples 1-3 provides methods for preparing representative compounds of formula (I). The skilled practitioner will know how to substitute the appropriate reagents, starting materials and purification methods known to those skilled in the art, in order to prepare additional compounds of the present invention.

Example 1

Synthesis of 5-(2-(1H-1,2,3-triazol-1-yl)ethyl)-2-((1R,6R)-3-methyl-6-(prop-1-en-2-yl)cyclohex-2-enyl)benzene-1,3-diol

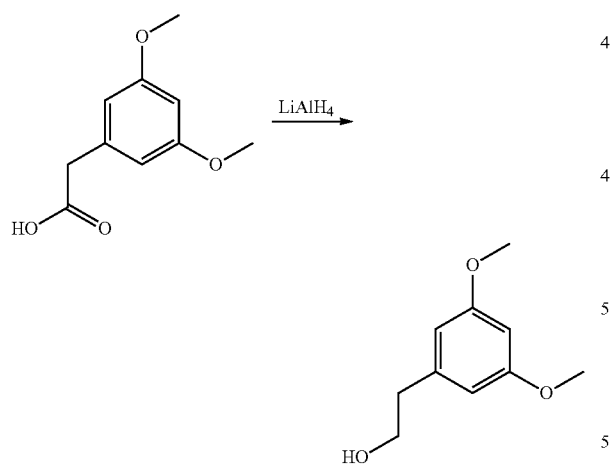

Step 1: Synthesis of 2-(3,5-dimethoxy-phenyl)-ethanol: To a suspension of LiAlH₄ (0.43 g, 11.33 mmol, 1.1 eq) in tetrahydrofuran (25 ml) was added a solution of (3,5-Dimethoxy-phenyl)-acetic acid (2 g, 10.19 mmol, 1.0 eq) in tetrahydrofuran (20 mL) dropwise at the rate of keeping the inner temperature below 30° C. and the mixture was continued stirring for additional 30 minutes. Thin layer chromatography analysis indicated the consumption of (3,5-Dimethoxy-phenyl)-acetic acid. Water (1 mL) was added slowly to quench the reaction, followed by 15% aqueous KOH (1 mL) and water (3 mL). The solid formed was filtered off and the filtered cake was washed with tetrahydrofuran (2×30 mL). The combined filtrate was dried over Na₂SO₄, concentrated to obtain the crude 2-(3,5-Dimethoxy-phenyl)-ethanol as yellow oil which was used without further purification. H-NMR (300 MHz, CDCl₃) δ 6.41-6.31 (m, 3H), 3.71 (s, 6H), 3.59 (m, 2H), 2.66 (t, J=7.2 Hz, 2H).

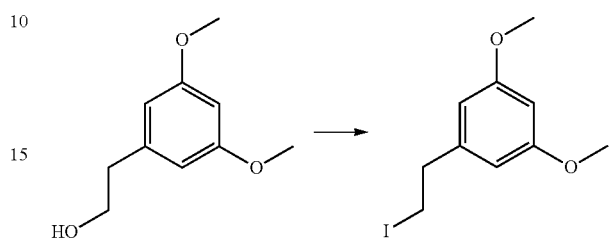

Step 2: Synthesis of 1-(2-Iodo-ethyl)-3,5-dimethoxy-benzene: To a mixture of triphenylphosphine (4.56 g, 17.38 mmol, 1.5 eq), iodine (4.41 g, 17.37 mmol, 1.5 eq) and imidazole (1.97 g, 28.93 mmol, 2.5 eq) in dichloromethane (80 mL) was added a solution of 2-(3,5-dimethoxy-phenyl)-ethanol (2.11 g, 11.57 mmol, 1.0 eq) in dichloromethane (25 mL) and the resulting mixture was continued stirring for at room temperature for 45 minutes. Thin layer chromatography analysis indicated the complete consumption of 2-(3,5-dimethoxy-phenyl)-ethanol. An aqueous solution of NaHSO₃ (100 mL) was added to quench the reaction. The water phase was extracted by diethyl ether (3×100 mL). The combined organic phase was dried over Na₂SO₄, filtered and concentrated to give crude 1-(2-Iodo-ethyl)-3,5-dimethoxy-benzene as yellow oil. The crude material was purified by column chromatography to provide 1-(2-Iodo-ethyl)-3,5-dimethoxy-benzene as the yellow oil. H-NMR (300 MHz, CDCl₃) δ 6.39-6.36 (m, 3H), 6.36 (s, 6H), 3.36 (t, J=8.1 Hz, 2H), 3.14 (t, J=7.8 Hz, 2H).

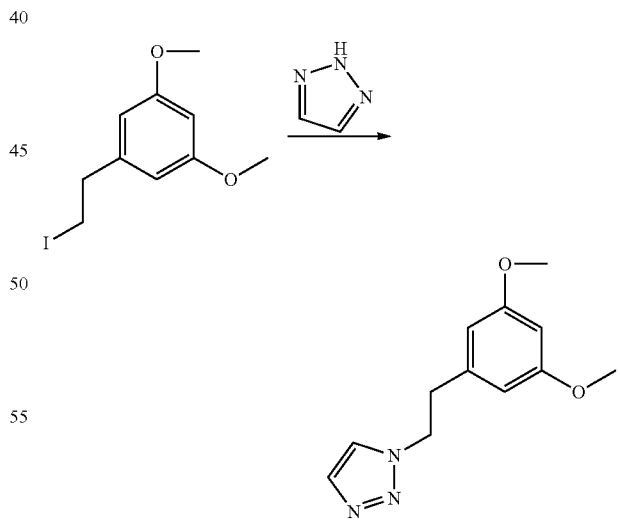

Step 3: Synthesis of 1-[2-(3,5-Dimethoxy-phenyl)-ethyl]-1H-[1,2,3]triazole: To a solution of 2H-1,2,3-triazole (0.28 g, 4.05 mmol, 1.0 eq) in N,N-dimethylacetamide (72 mL) was added NaH (60%, 0.2 g, 5.0 mmol, 1.2 eq) and stirred at room temperature for 30 minutes. 1-(2-Iodo-ethyl)-3,5-dimethoxy-benzene (1.2 g, 4.1 mmol, 1.0 eq) was added and the resulting mixture was stirred at room temperature for 14 hours. Thin layer chromatography analysis showed the completion of the reaction. Water (100 mL) was added to quench the reaction. The water phase was extracted with ethyl acetate (3×50 mL). The ethyl acetate phase was back washed with brine (3×50 mL), dried and concentrated to give the crude product. The crude product was purified by column chromatography with ethyl acetate/hexane to give 1-[2-(3,5-Dimethoxy-phenyl)-ethyl]-1H-[1,2,3]triazole.
H-NMR (300 MHz, CDCl$_3$) δ 7.64 (s, 1H), 7.31 (s, 1H), 4.63 (t, J=7.2 Hz, 2H), 3.75 (s, 6H), 3.16 (t, J=7.2 Hz, 3H).

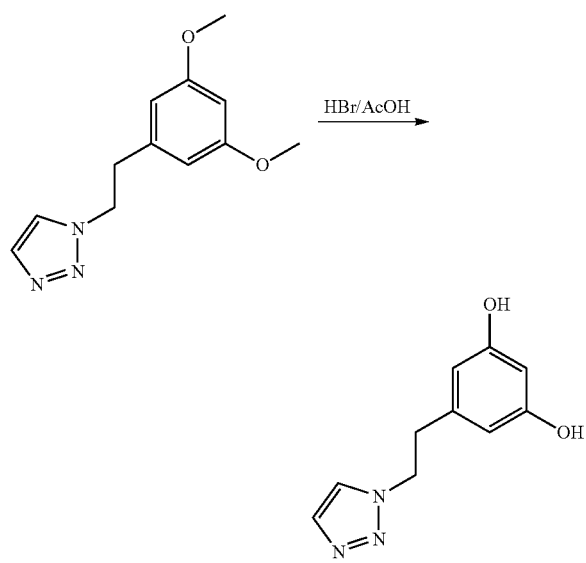

Step 4: Synthesis of 5-(2-[1,2,3]Triazol-1-yl-ethyl)-benzene-1,3-diol: A solution of 1-[2-(3,5-Dimethoxy-phenyl)-ethyl]-1H-[1,2,3]triazole (0.13 g, 0.56 mmol, 1.0 eq) in 40% HBr/acetic acid (1:1) (6 mL) was refluxed for 12 hours under the protection by nitrogen. Thin layer chromatography analysis indicated the completion of the reaction. The reaction mixture was concentrated to dryness. The residue was dissolved in ethyl acetate (10 ml) and treated with a solution of saturated NaHCO$_3$ to adjust the pH to 5-6. The organic phase was separated and the aqueous phase was extracted by ethyl acetate (2×5 mL). The combined organic phase was dried over Na$_2$SO$_4$, filtered and concentrated to give crude 5-(2-[1,2,3]Triazol-1-yl-ethyl)-benzene-1,3-diol as yellow solid. The crude 5-(2-[1,2,3]Triazol-1-yl-ethyl)-benzene-1, 3-diol was used directly for the next step without further purification. H-NMR (300 MHz, CD$_3$OD) δ 7.76 (s, 1H), 7.66 (s, 1H), 6.09 (m, 3H), 4.64 (t, J=7.0 Hz, 2H), 3.05 (t, J=7.0 Hz, 2H).

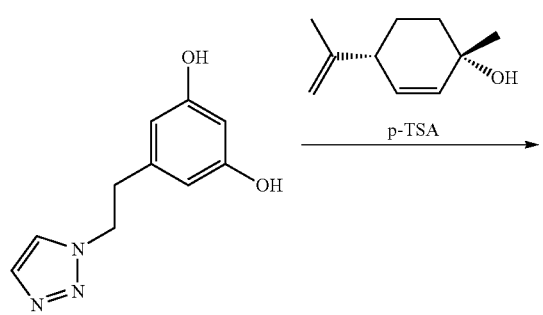

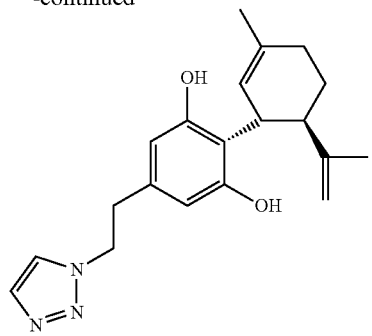

Step 5: Synthesis of 5-(2-(1H-1,2,3-triazol-1-yl)ethyl)-2-((1R,6R)-3-methyl-6-(prop-1-en-2-yl)cyclohex-2-enyl)benzene-1,3-diol: To the mixture of 5-(2-[1,2,3]Triazol-1-yl-ethyl)-benzene-1,3-diol (200 mg, 0.98 mmol, 1.0 eq) and p-toluenesulfonic acid (74 mg, 0.43 mmol, 0.4 eq) in a mixed solvent of tetrahydrofuran/dichloromethane (4:1) (10 mL) was slowly added 4-(R)-Isopropenyl-1-(S)-methyl-cyclohex-2-enol (223 mg, 1.46 mmol, 1.5 eq). The reaction mixture was still a suspension. Acetic acid (2 mL) was then added and the reaction was stirred at room temperature for 0.5 hour. The reaction mixture was diluted with ethyl acetate (10 mL). The pH value was adjusted to ~7 by the addition of the saturated NaHCO$_3$ solution. The organic phase was separated and the water phase was extracted by ethyl acetate (2×10 mL). The combined organic phase was dried over Na$_2$SO$_4$, filtered and concentrated to give crude product. The crude product was purified through preparative HPLC to give 5-(2-(1H-1,2,3-triazol-1-yl)ethyl)-2-((1R,6R)-3-methyl-6-(prop-1-en-2-yl)cyclohex-2-enyl)benzene-1,3-diol. LCMS (ESI): m/z 340 (M+1), m/z 362 (M+Na). H-NMR (300 MHz, CD$_3$OD) δ 7.63 (s, 1H), 7.61 (s, 1H), 6.04 (s, 2H), 5.26 (s, 1H), 4.61 (t, J=6.9 Hz, 2H), 4.45 (d, J=3 Hz, 2H), 4.00-3.92 (m, 1H), 3.00-2.90 (m, 3H), 2.30-2.00 (m, 2H), 1.80-1.70 (m, 2H), 1.68 (s, 3H), 1.64 (s, 3H).

Example 2

Synthesis of 1-(3-(3,5-dihydroxy-4-((1R,6R)-3-methyl-6-(prop-1-en-2-yl)cyclohex-2-enyl)benzyl)azetidin-1-yl)ethanone (KLS-13019)

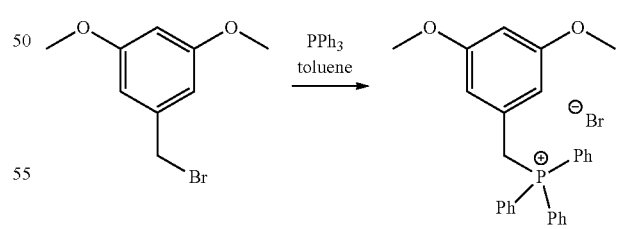

Step 1: Synthesis of (3,5-Dimethoxy-benzyl)-triphenylphosphonium bromide: A solution of 1-Bromomethyl-3,5-dimethoxy-benzene (12 g, 51.92 mmol, 1.0 eq) and triphenylphosphine (15 g, 57.18 mmol, 1.1 eq) in toluene (100 mL) was refluxed for 4 hours. Thin layer chromatography analysis indicated that the starting material was consumed completely. The reaction mixture was cooled to room temperature and the resulting solid was collected by filtration. The solid was sonicated in methanol/petroleum ether (1:20, 220 mL) for one hour, filtered and the filter cake was washed by petroleum ether (3×20 mL) to give a crude product (3,5-dimethoxy-benzyl)-triphenyl-phosphonium bromide as white solid. The crude (3,5-dimethoxy-benzyl)-triphenyl-phosphonium bromide was used directly for the next step without further purification. H-NMR (300 MHz, CDCl₃) δ 7.94-7.89 (m, 3H), 7.79-7.65 (m, 12H), 6.43 (s, 1H), 6.12 (t, J=2.4 Hz, 2H), 5.08 (s, 1H), 5.03 (s, 1H), 3.50 (s, 6H).

Step 2: Synthesis of 3-(3,5-Dimethoxy-benzylidene)-azetidine-1-carboxylic acid tert-butyl ester

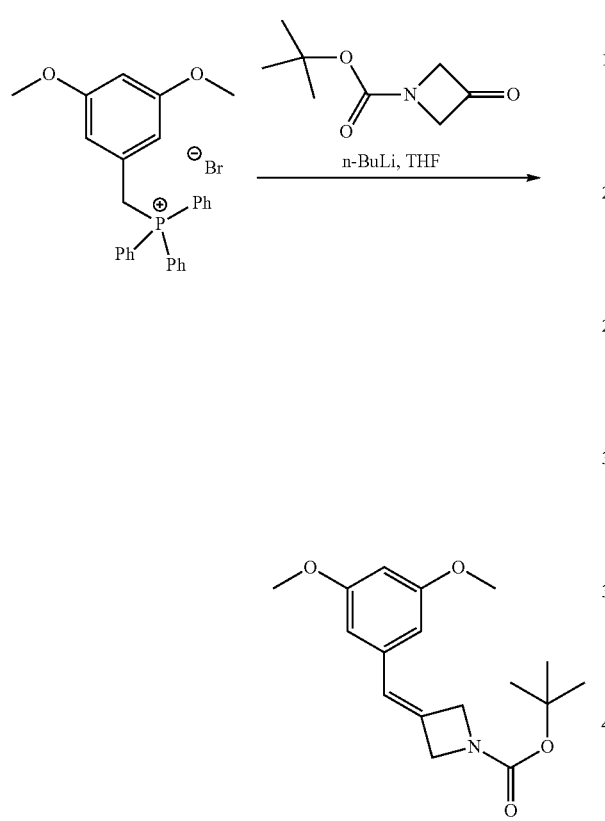

To a suspension of (3,5-dimethoxy-benzyl)-triphenyl-phosphonium bromide (23.07 g, 46.76 mmol, 2.0 eq) in anhydrous tetrahydrofuran (150 mL) was added n-butyl lithium (2.5M in tetrahydrofuran, 21 mL, 52.5 mmol, 2.2 eq) dropwise at 0° C. After stirred for 20 minutes, the solution of 3-Oxo-azetidine-1-carboxylic acid tert-butyl ester (4 g, 23.36 mmol, 1.0 eq) in dry tetrahydrofuran (50 mL) was added dropwise. The cooling bath was removed after the addition and the reaction mixture was stirred at room temperature for one hour. Thin layer chromatography analysis showed the consumption of the 3-Oxo-azetidine-1-carboxylic acid tert-butyl ester. Water (200 mL) was added to quench the reaction. The quenched reaction mixture was extracted with ethyl acetate (3×100 mL), dried and concentrated to dryness. The crude residue was purified by column chromatography (ethyl acetate/Hexane=1/15) to give pure product 3-(3,5-Dimethoxy -benzylidene)-azetidine-1-carboxylic acid tert-butyl ester as pale yellow oil that solidified on standing. H-NMR (300 MHz, CDCl₃) δ 6.38-6.36 (m, 1H), 6.27 (s, 2H), 6.21 (s, 1H), 4.85-4.83 (m, 2H), 4.66-4.64 (m, 2H), 3.80 (s, 6H), 1.50 (s, 9H).

Step 3: Synthesis of 3-(3,5-Dimethoxy-benzyl)-azetidine-1-carboxylic acid tert-butyl ester

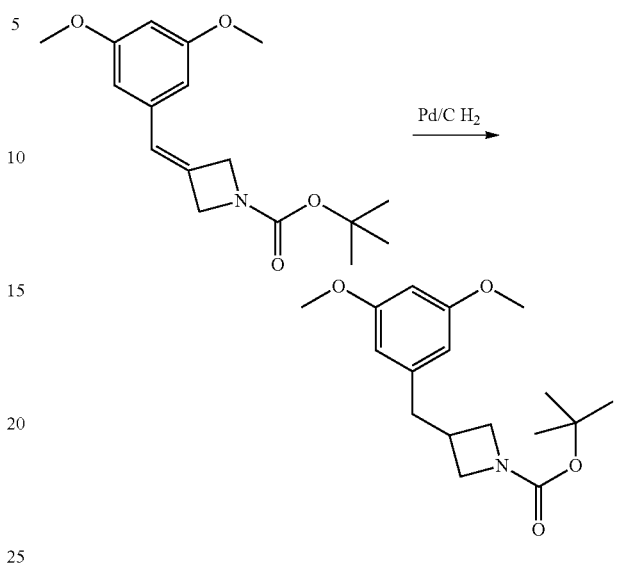

After purged with nitrogen, a suspension of 3-(3,5-Dimethoxy-benzylidene)-azetidine-1-carboxylic acid tert-butyl ester (4.5 g, 14.73 mmol, 1.0 eq) and 10% palladium on carbon (4 g) in ethyl acetate (800 mL) was stirred under a hydrogen atmosphere (balloon) at room temperature for 4 hours. Thin layer chromatography indicated the full consumption of 3-(3,5-Dimethoxy-benzylidene)-azetidine-1-carboxylic acid tert-butyl ester. The palladium on carbon catalyst was filtered off through Celite. The filtrate was concentrated to give crude 3-(3,5-Dimethoxy-benzyl)-azetidine-1-carboxylic acid tert-butyl ester, which was directly used for the next step without further purification. H-NMR (300 MHz, CDCl3) δ 6.32-6.29 (m, 3H), 4.03-3.97 (m, 2H), 3.78 (s, 6H), 3.67-3.62 (m, 2H), 2.86-2.76 (m, 3H), 1.47 (s, 9H).

Step 4: Synthesis of 3-(3,5-Dimethoxy-benzyl)-azetidine:

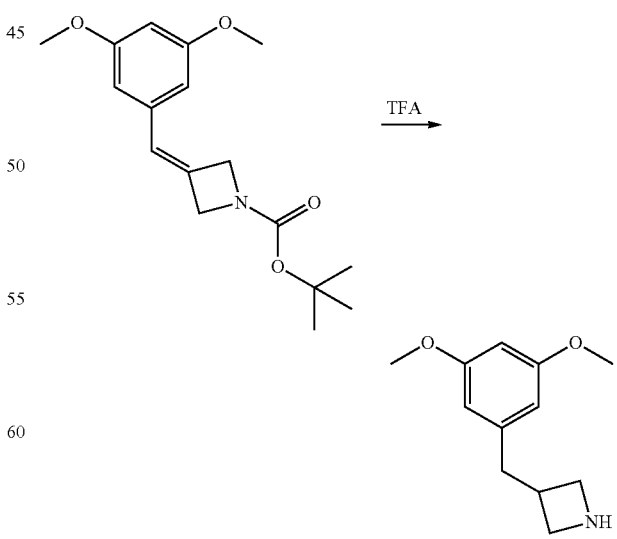

With protection of nitrogen, a mixture of compound 3-(3,5-Dimethoxy-benzyl) -azetidine-1-carboxylic acid tert-butyl ester (1.5 g, 4.88 mmol, 1.0 eq), trifluoroacetic acid (10 mL) and dichloromethane (30 mL) was stirred at 0° C. for 40 minutes. Thin layer chromatography analysis indicated the completion of the reaction. The reaction mixture was concentrated and the residue was dissolved in dichloromethane (20 mL). The solution was adjusted to pH=8-9 with aqueous NaHCO$_3$. The organic layer was separated and the aqueous layer was extracted with dichloromethane (3×20 mL). The combined organic phase was dried over Na$_2$SO$_4$, filtrated and concentrated to give the crude product 3-(3,5-Dimethoxy-benzyl)-azetidine as white solid, which was used for the next step without further purification. H-NMR (300 MHz, CDCl$_3$) δ 6.35 (s, 1H), 6.28 (s, 2H), 4.09 (t, J=10.5 Hz, 2H), 3.83 (t, J=7.2 Hz, 2H), 3.78 (s, 6H), 3.28-3.10 (m, 1H), 2.94 (d, J=8.1 Hz, 2H).

Step 5: Synthesis of 1-[3-(3,5-Dimethoxy-benzyl)-azetidin-1-yl]-ethanone

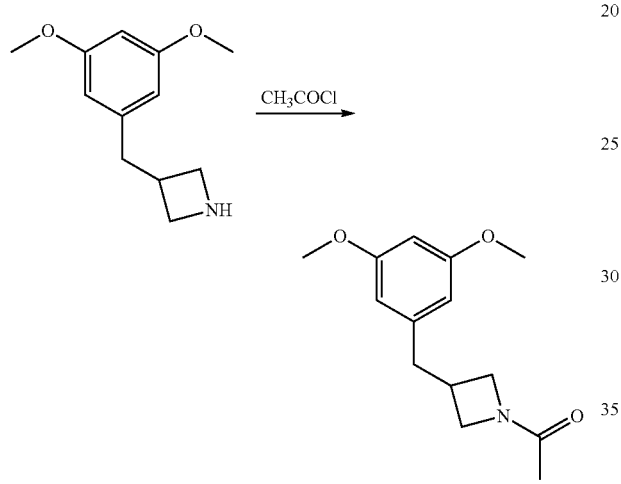

A mixture of 3-(3,5-Dimethoxy-benzyl)-azetidine (1.0 g, 4.83 mmol, 1 eq), triethyl amine (0.98 g, 9.68 mmol, 2 eq) and acetyl chloride (0.46 g, 5.8 mmol, 1.2 eq) in dichloromethane (20 mL) was stirred at room temperature for one hour. Water was added to quench the reaction. The organic layer was separated and the aqueous layer was extracted with ethyl acetate (2×20 mL). The organic layer was combined and washed with brine, dried over Na$_2$SO$_4$, filtrated and concentrated to provide 1-[3-(3,5-Dimethoxy -benzyl)-azetidin-1-yl]-ethanone as yellow oil, which was used for the next step without further purification. H-NMR (300 MHz, CDCl$_3$) δ 6.35-6.30 (m, 3H), 4.30-4.00 (m, 2H), 3.90-3.70 (m, 8H), 3.00-2.80 (m, 3H), 1.86 (s, 3H).

Step 6: Synthesis of 1-[3-(3,5-Dihydroxy-benzyl)-azetidin-1-yl]-ethanone

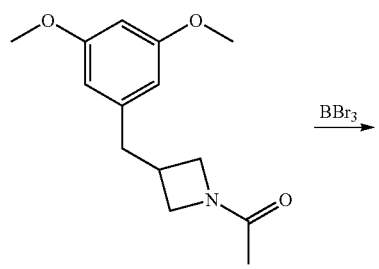

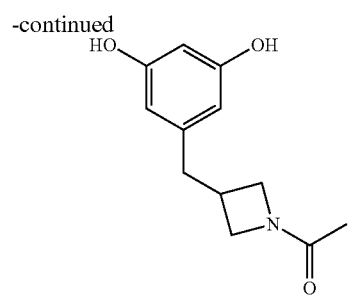

A solution of BBr$_3$ (7.7 g, 30.84 mmol, 8.0 eq) in dichloroethane (30 ml) was slowly added to the solution of 1-[3-(3,5-Dimethoxy-benzyl)-azetidin-1-yl]-ethanone (0.96 g, 3.86 mmol, 1.0 eq) in dichloromethane (100 mL) under nitrogen over 20 minutes at −5 to 0° C. The resulting reaction mixture was stirred at room temperature for another 2.5 hours. Thin layer chromatography analysis indicated the completion of the reaction. An aqueous solution of NH$_4$Cl (80 mL) was added to quench the reaction. The organic layer was separated and the aqueous layer was extracted with ethyl acetate (4×100 mL). The combined organic layer was washed with brine, dried over Na$_2$SO$_4$, filtrated and concentrated to give a crude product as yellow solid. The crude product was purified by column chromatography to provide 1-[3-(3,5-Dihydroxy-benzyl)-azetidin-1-yl]-ethanone.
H-NMR (300 MHz, CD$_3$OD) δ 6.14 (m, 3H), 4.28-4.20 (m, 1H), 4.00-3.95 (m, 1H), 3.95-3.85 (m, 1H), 3.60-3.50 (m, 1H), 2.95-2.80 (m, 1H), 2.78 (m, 2H), 1.86 (s, 3H).

Step 7: Synthesis of 1-(3-(3,5-dihydroxy-4-((1R,6R)-3-methyl-6-(prop-1-en-2-yl)cyclohex-2-enyl)benzyl)azetidin-1-yl)ethanone (KLS-13019):

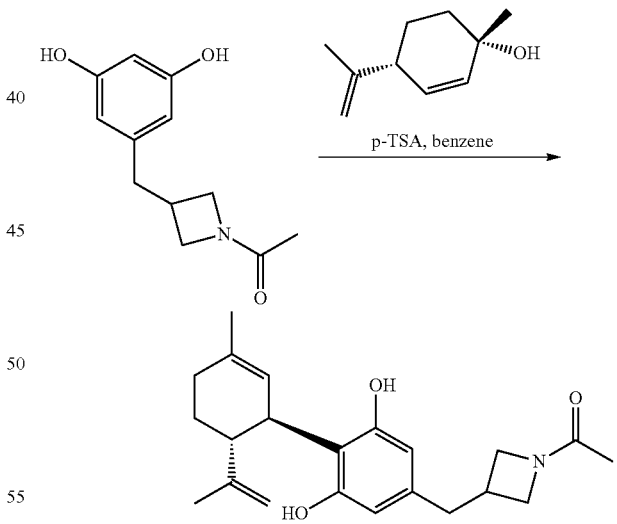

To a solution of 1-[3-(3,5-Dihydroxy-benzyl)-azetidin-1-yl]-ethanone (350.0 mg, 1.58 mmol, 1 eq) and BF$_3$-Et$_2$O (673 mg, 4.74 mmol, 3 eq) in dichloromethane/tetrahydrofuran (4:1, 50 mL) was added a solution of 4-(R)-Isopropenyl-1-(S)-methyl-cyclohex-2-enol (241 mg, 1.58 mmol, 1 eq) in dichloromethane/tetrahydrofuran (4:1, 3 mL) at room temperature over 15 minutes. After the addition, the mixture was stirred at room temperature for additional 50 minutes. Thin layer chromatography analysis showed 20-30% conversion of 1-[3-(3,5-Dihydroxy -benzyl)-azetidin-1-yl]- ethanone. The reaction was stopped at that point. An aqueous solution of NaHCO₃ (20 mL) was added to quench the reaction. The aqueous layer was extracted with ethyl acetate/tetrahydrofuran (1:1) (3×20 mL). The combined organic phase was dried over Na₂SO₄, filtrated and concentrated to dryness. The residue was purified through column chromatography to give the crude product 1-(3-(3,5-dihydroxy-4-((1R,6R)-3-methyl-6-(prop-1-en-2-yl)cyclohex-2-enyl)benzyl)azetidin-1-yl)ethanone with 70-80% purity and the intermediate 1-[3-(3,5-Dihydroxy-benzyl)-azetidin-1-yl]-ethanone recovered. The crude 1-(3-(3,5-dihydroxy-4-((1R,6R)-3-methyl-6-(prop-1-en-2-yl)cyclohex-2-enyl)benzyl)azetidin-1-yl)ethanone was further purified by preparative Thin layer chromatography to provide 1-(3-(3,5-dihydroxy-4-((1R,6R)-3-methyl-6-(prop-1-en-2-yl)cyclohex-2-enyl)benzyl)azetidin-1-yl)ethanone. The recovered 1-[3-(3,5-Dihydroxy-benzyl)-azetidin-1-yl]-ethanone was subsequently converted to compound 1-(3-(3,5-dihydroxy-4-((1R,6R)-3-methyl-6-(prop-1-en-2-yl)cyclohex-2-enyl)benzyl)azetidin-1-yl)ethanone using the same procedure. The two batches were combined to give 1-(3-(3,5-dihydroxy-4-((1R,6R)-3-methyl-6-(prop-1-en-2-yl)cyclohex-2-enyl)benzyl)azetidin-1-yl)ethanone. LCMS (ESI): m/z 356 (M+1), m/z 378 (M+Na). H-NMR (300 MHz, CDCl₃) δ 6.35-6.15 (br s, 2H), 6.15-5.95 (br s, 1H), 5.55 (s, 1H), 4.65 (s, 1H), 4.55 (s, 1H), 4.25-4.15 (m, 1H), 4.15-4.00 (m, 1H), 3.95-3.85 (m, 1H), 3.85-3.65 (m, 2H), 2.90-2.70 (m, 3H), 2.45-2.35 (m, 1H), 2.30-2.00 (m, 3H), 1.90-1.80 (m, 7H), 1.67 (s, 3H).

Example 3

Synthesis of ethyl 3-(3,5-dihydroxy-4-((1R,6R)-3-methyl-6-(prop-1-en-2-yl)cyclohex-2-enyl)benzyl)azetidine-1-carboxylate Step 1: Synthesis of 3-Oxo-azetidine-1-carboxylic acid ethyl ester:

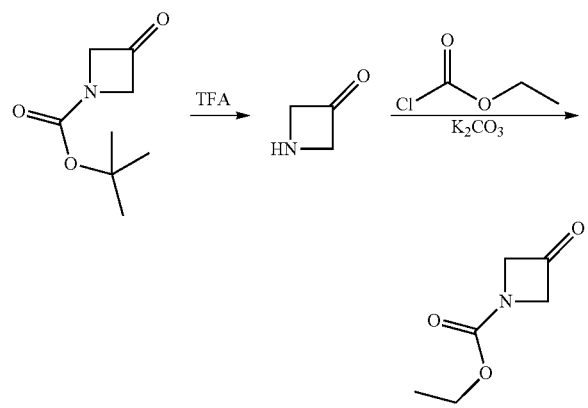

A solution of 3-Oxo-azetidine-1-carboxylic acid tert-butyl ester (4.3 g, 25.1 mmol, 1 eq) in 30% trifluoroacetic acid in dichloromethane was stirred at room temperature for 2 hours. Thin layer chromatography analysis indicated the disappearance of the 3-Oxo-azetidine-1-carboxylic acid tert-butyl ester. The reaction mixture was concentrated to dryness on a rotavapor to give crude Azetidin-3-one. The crude Azetidin-3-one was dissolved in tetrahydrofuran (20 mL) and treated with ethyl chloroformate (2) (4.07 g, 37.7 mmol, 1.5 eq). To the resulting mixture, an aqueous solution of K₂CO₃ (10.4 g, 75.3 mmol, 3 eq) in water (20 mL) was added dropwise at 0° C. After the addition, the reaction mixture was allowed to warm to room temperature and stirred for 1.5 hours. Thin layer chromatography analysis indicated the completion of the reaction. The reaction mixture was extracted with ethyl acetate (3×30 mL), back washed by brine (30 mL), dried and concentrated to provide 3-Oxo-azetidine-1-carboxylic acid ethyl ester as solid. H-NMR (300 MHz, CDCl₃) δ 4.77 (s, 4H), 4.20 (q, J=7.1 Hz, 2H), 1.30 (t, J=7.1 Hz, 3H).

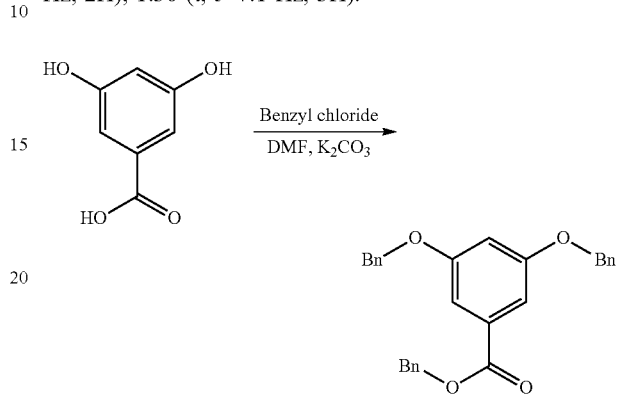

Step 2: Synthesis of 3,5-bis-benzyloxy-benzoic acid benzyl ester: To a solution of 3,5-dihydroxybenzoic acid (8.0 g, 51.9 mol, 1.0 eq) in N, N-dimethylformamide (25 mL) was added K₂CO₃ (28.6 g, 0.2076 mol). The mixture was stirred at room temperature for 30 minutes. A solution of benzyl chloride (21.6 g, 171.3 mmol, 3.3 eq) in N, N-dimethylformamide (25 mL) was added and the resulting suspension was stirred at 70° C. overnight. The progress of the reaction was monitored by thin layer chromatography. After the starting material was consumed, water (50 mL) was added to quench the reaction. The quenched reaction mixture was extracted with ethyl acetate (3×50 mL). The combined organic phase was washed with 10% brine (3×50 mL), dried over Na₂SO₄, filtered and concentrated in vacuo to give crude product 3,5-bis-benzyloxy-benzoic acid benzyl ester as brown solid, which was used for the next step without further purification. H-NMR (300 MHz, CDCl₃) δ 7.50-7.28 (m, 17H), 6.84 (s, 1H), 5.37 (s, 2H), 5.09 (s, 4H).

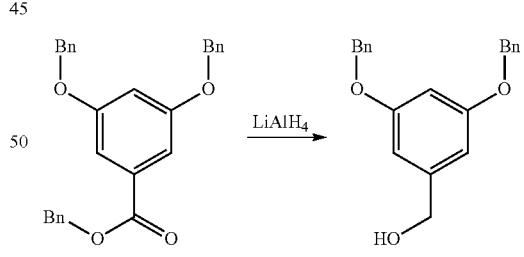

Step 3: Synthesis of (3,5-Bis-benzyloxy-phenyl)-methanol

To a suspension of LiAlH₄ (14 g, 0.368 mol, 4 eq) in tetrahydrofuran (100 mL), was added the solution of 3,5-bis-benzyloxy-benzoic acid benzyl ester (39 g, 0.092 mol, 1 eq) in tetrahydrofuran (100 mL) over 20 minutes and the resulting mixture was stirred at room temperature for one hour. Thin layer chromatography analysis showed the completion of the reaction. To the reaction mixture was then slowly added water (40 mL), 15% KOH aqueous solution (40 mL), and water (120 mL) in order. The resulting solid was filtered off. The organic phase was separated off and the aqueous layer was extracted with ethyl acetate (100 mL). The combined organic layer was dried and concentrated. The residue was purified through column chromatography (ethyl acetate/hexane=1/8) to give the desired product (3,5-Bis -benzyloxy-phenyl)-methanol. H-NMR (300 MHz, CDCl₃) δ 7.50-7.30 (m, 10H), 6.66-6.50 (m, 3H), 5.06 (s, 4H), 4.65 (d, J=6.0 Hz, 2H).

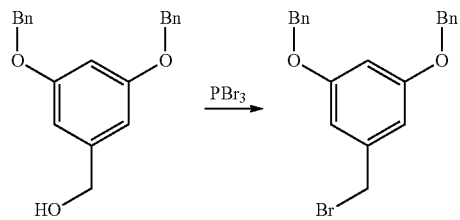

Step 4: Synthesis of 1,3-Bis-benzyloxy-5-bromomethyl-benzene: To a solution of (3,5-Bis-benzyloxy-phenyl)-methanol (18 g, 56 mmol, 1.0 eq) in acetonitrile (100 mL) was added the solution of phosphorous tribromide (22.8 g, 84 mmol, 1.5 eq) in acetonitrile (50 mL) dropwise at 0 to 5° C. After the addition, the reaction mixture was continued stirring at 0-5° C. for 2 hours. Thin layer chromatography showed the completion of the reaction. Water (50 mL) was added over 30 minutes. The solid formed was filtered. The solid was re-dissolve in ethyl acetate (100 mL) and washed by brine (100 mL), dried and concentrated to obtain crude product 1,3-Bis-benzyloxy-5-bromomethyl-benzene which was used without further purification. H-NMR (300 MHz, CDCl₃) δ 7.45-7.33 (m, 10H), 6.67 (s, 2H), 6.58 (s, 1H), 5.05 (s, 4H), 4.44 (s, 2H).

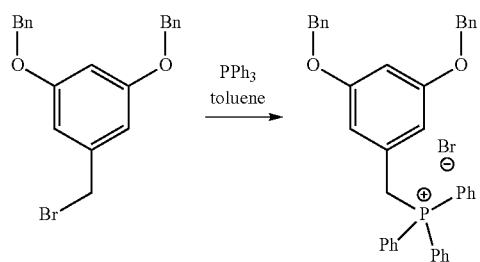 [SMILES: BrCc1cc(OCc2ccccc2)cc(OCc2ccccc2)c1 ; c1ccc(COc2cc(C[P+](c3ccccc3)(c3ccccc3)c3ccccc3)cc(OCc3ccccc3)c2)cc1 ; [Br-]]

Step 5: Synthesis of (3,5-Bis-benzyloxy-benzyl)-triphenylphosphonium bromide: A solution of 1,3-bis-benzyloxy-5-bromomethyl-benzene (16 g, 42 mmol, 1.0 eq) and triphenylphosphine (12 g, 46.2 mmol, 1.1 eq) in toluene (100 ml) was refluxed for 3-4 hours. The starting material 1,3-bis-benzyloxy-5-bromomethyl-benzene was completely consumed as indicated by thin layer chromatography. The reaction mixture was cooled to room temperature. The solid formed was collected by filtration. The solid was sonicated in methanol/petroleumether (1:20, 220 mL) for one hour, filtered and the filter cake was washed by petroleumether (3×20 mL) to give product (3,5-Bis-benzyloxy-benzyl)-triphenylphosphonium bromide as white solid which was used without further purification. H-NMR (300 MHz, CDCl₃) δ 7.89-7.78 (m, 3H), 7.77-7.68 (m, 12H), 7.40-7.21 (m, 10H), 6.62 (s, 1H), 6.22 (s, 2H), 5.08 (s, 1H), 5.03 (s, 1H), 4.82 (s, 4H).

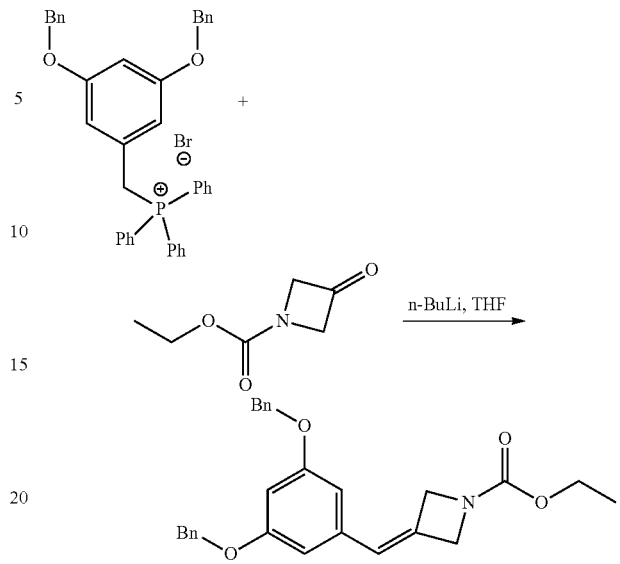

Step 6: Synthesis of 3-(3,5-Bis-benzyloxy-benzylidene)-azetidine-1-carboxylic acid ethyl ester: Under the protection of nitrogen, n-butyl lithium in hexane (2.5M, 15.1 mL, 37.75 mmol, 2 eq) was added to a suspension of (3,5-Bis-benzyloxy-benzyl) -triphenylphosphonium bromide (8.1 g, 12.59 mmol, 1.0 eq) in dry tetrahydrofuran (150 mL) at −5 to 0° C. over 20 minutes. After stirred at 0° C. for 20 minutes, a solution of 3-oxo-azetidine-1-carboxylic acid ethyl ester (3.6 g, 25.17 mmol, 2 eq) in tetrahydrofuran (100 mL) was added dropwise. After the addition, the ice-salt cooling bath was removed and the reaction was allowed warm to room temperature and continued stirring for additional one hour. Thin layer chromatography indicated the disappearance of 3-oxo -azetidine-1-carboxylic acid ethyl ester. Water (150 mL) was added to quench the reaction. The mixture was extracted by ethyl acetate (3×100 mL). The combined organic phase was washed with brine (100 mL), dried and concentrated. The crude product was purified by column chromatography (ethyl acetate/hexane=1/10) to provide the desired product 3-(3,5-Bis-benzyloxy-benzylidene)-azetidine-1-carboxylic acid ethyl ester. H-NMR (300 MHz, CDCl3) δ 7.77-7.37 (m, 10H), 6.54-6.53 (m, 1H), 6.33 (d, J=1.9 Hz, 2H), 6.19 (s, 1H), 5.05 (s, 4H), 4.78 (s, 2H), 4.68 (s, 2H), 4.21-4.13 (q, J=7.1 Hz, 2H), 1.30 (t, J=7.1 Hz, 3H).

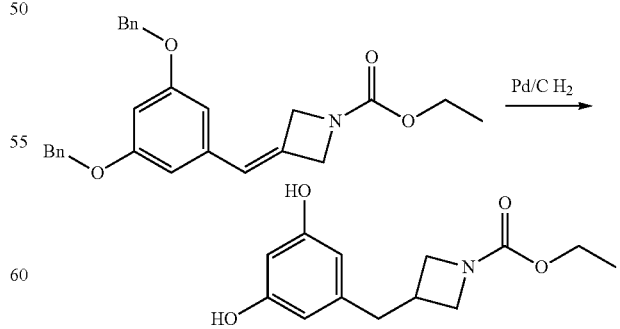

Step 7: Synthesis of 3-(3,5-dihydroxy-benzyl)-azetidine-1-carboxylic acid ethyl ester: A suspension of 3-(3,5-Bis-benzyloxy-benzylidene)-azetidine-1-carboxylic acid ethyl ester (4.0 g, 9.3 mmol, 1 eq) and 10% palladium on carbon (1.0 g, 0.1 eq) in ethyl acetate (400 mL) was stirred under hydrogen balloon at room temperature for 4 hours. Thin layer chromatography showed the completion of the reaction. The palladium on carbon catalyst was filtered off through Celite. The filtrate was concentrated to give a crude product 3-(3,5-dihydroxy-benzyl)-azetidine-1-carboxylic acid ethyl ester, which was used directly for the next step without further purification. LCMS (ESI): m/z 252 (M+1). H-NMR (300 MHz, CDCl$_3$) δ 6.24-6.19 (m, 2H), 5.98 (brs, 1H), 4.17-4.11 (m, 2H), 4.06-4.01 (m, 2H), 3.70-3.67 (m, 1H), 2.77 (brs, 2H), 1.30-1.23 (m, 3H).

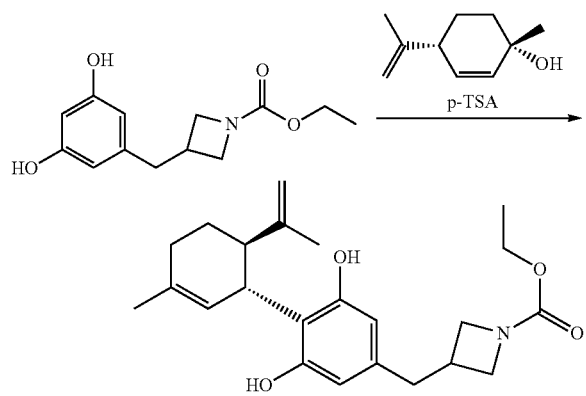

Step 8: Synthesis of ethyl 3-(3,5-dihydroxy-4-((1R,6R)-3-methyl-6-(prop-1-en-2-yl)cyclohex-2-enyl)benzyl)azetidine-1-carboxylate: Four parallel batches were carried out as follows. To a suspension of 3-(3,5-dihydroxy-benzyl)-azetidine-1-carboxylic acid ethyl ester (0.45 g, 1.79 mmol, 1.2 eq) in chloroform (45 mL), was added p-toluenesulfonic acid (68 mg, 0.39 mmol, 0.26 eq) and 4-(R)-isopropenyl-1-(S)-methyl-cyclohex-2-enol (0.23 g, 1.5 mmol, 1 eq) and the resulting mixture was stirred at room temperature for 10 minutes. Thin layer chromatography analysis indicated ~60-70% conversion of the starting material 3-(3,5-dihydroxy-benzyl)-azetidine-1-carboxylic acid ethyl ester. A saturated NaHCO$_3$ solution was added to the reaction mixture to adjust the pH to 9-10. The organic phase was separated and the aqueous phase was extracted with dichloromethane (2×50 mL). The combined organic phase was dried over Na$_2$SO$_4$, filtered and concentrated to provide crude ethyl 3-(3,5-dihydroxy-4-((1R,6R)-3-methyl-6-(prop-1-en-2-yl) cyclohex-2-enyl)benzyl)azetidine-1-carboxylate. The four batches of crude ethyl 3-(3,5-dihydroxy-4-((1R,6R)-3-methyl-6-(prop-1-en-2-yl)cyclohex-2-enyl)benzyl)azetidine-1-carboxylate from the four parallel batches were combined and purified by column chromatography (ethyl acetate/hexane=1/3) and then further purified by preparative HPLC to provide ethyl 3-(3,5-dihydroxy-4-((1R,6R)-3-methyl-6-(prop-1-en-2-yl)cyclohex-2-enyl)benzyl)azetidine-1-carboxylate. HPLC: 99%. LCMS (ESI): m/z 408 (M+Na). H-NMR (300 MHz, CDCl3) δ 6.18-6.03 (m, 3H), 5.56 (s, 1H), 5.12 (s, 1H), 4.64 (s, 1H), 4.53 (s, 1H), 4.15-4.04 (m, 4H), 3.90-3.86 (m, 1H), 3.70-3.65 (m, 2H), 2.86-2.74 (m, 3H), 2.43-2.35 (m, 1H), 2.24-2.21 (m, 1H), 2.13-2.08 (m, 1H), 1.86-1.76 (m, 5H), 1.66 (s, 3H), 1.25 (t, J=7.1 Hz, 3H).

Formulations

The present invention also relates to compositions or formulations which comprise the functionalized 1,3-benzenediols according to the present invention. In general, the compositions of the present invention comprise an effective amount of one or more functionalized 1,3-benzenediols and salts thereof according to the present invention and one or more excipients which are effective for providing the treatment and prevention of hepatic encephalopathy.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known therapeutic agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound (s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more functionalized 1,3-benzenediols according to the present invention and one or more excipients; from about 0.01 mg to about 100 mg of one or more functionalized 1,3-benzenediols according to the present invention and one or more excipients; and from about 0.1 mg to about 10 mg of one or more functionalized 1,3-benzenediols according to the present invention; and one or more excipients.

Procedures

The following procedures can be utilized in evaluating and selecting compounds as neuroprotective agents against ethanol and ammonia toxicity.

Cell cultures: All compounds were screened with dissociated hippocampal cultures derived from embryonic day 18 rats as the primary test system. With this preparation, primary neurons were used to test for toxicity as well as neuroprotection in a highly relevant experimental system to hepatic encephalopathy (HE). In brief, hippocampal tissue was obtained commercially through Brain Bits (Springfield, Ill.) and cultures prepared as previously described (Brewer, 1995). The hippocampal neurons were platted at low density (10,000 cell/well) in a 96-well format and maintained in serum-free medium consisting of Neurobasal Medium supplemented with B27 and GlutaMAX (Gibco). Pre-coated poly-D-lysine coated plates will be used because of the adherence and survival of hippocampal neurons and glia on this matrix support.

In vitro neuroprotection testing: Potent neuroprotection from oxidative stress associated with ethanol and ammonia treatment is the primary goal in the treatment of HE. The central objective of all neuroprotective assays was their relevancy to oxidative stress related to HE and other or diseases associated with oxidative stress in general. These studies use phenotypic assays of neuroprotection because the molecular target(s) mediating the action of cannabidiol-like protecting substances is unknown. Both the amount of ethanol and ammonia used in the assays, as well as the time of treatment and duration of the experiment, were designed to be relevant to HE (Ong et al, 2003). Further, all time parameters employed in these studies were empirically determined to be within the limits of reversible toxic events after treatment with cannabidiol (Hamelink et al., 2005) and cannabidiol-like substances, yet using amounts of ethanol (30 mM) and ammonia (300 µM ammonium acetate) that were relevant to the disease.

In regard to ethanol toxicity, a critical feature was the amount of ethanol used to treat the hippocampal neurons. The effective working concentration of ethanol that was empirically determined to produce toxicity in the hippocampal cultures was 30 mM. With respect to blood alcohol levels needed to produce intoxication in human, this amount of ethanol results in severe intoxication. For a perspective set by the National Institute on Alcohol Abuse and Alcoholism, "binge drinking" has been defined as blood alcohol levels exceeding 0.08 g percent (20 mM) or higher. Thus, the amount used in the in vitro test system is relevant.

In regard to ammonia toxicity and HE, the important clinical feature of blood ammonia levels was taken from the studies of Ong et al., 2003. In severe cases of HE (stages 3 and 4), arterial ammonia levels were observed a 150-200 µM. In all the current studies, ammonium acetate was used to model the ammonia toxicity (Warren, 1957). The working concentration of ammonium acetate utilized in the present acute toxicity studies was 300 µM. No additional toxicity was produced from that observed with 300 µM ammonium acetate when tested up to 1 mM ammonium acetate. In addition to testing for neuroprotection from ammonium acetate and ethanol separately, the protective effect of program compounds tested against the toxicity produced by a combination of 30 mM ethanol and 300 µM ammonium acetate was also evaluated to further demonstrate the relevance to HE.

Vital Dyes Utilized

Carboxyfluorescein (CFDA) was used a vital stain for all neuroprotection studies. With the use of the CytoFluor fluorimeter, the CFDA assay was employed to assess the viability of neurons. CFDA is a dye that becomes fluorescent upon cell entry and cleavage by cytosolic esterases (Petroski and Geller, 1994). Neuronal specificity is obtained relative to astrocytes because the cleaved dye is extruded extracellularly by glia with time, while dye in neurons remains intracellular. Previous experience with this assay showed a good correlation with neuronal cell counts stained immunocytochemically with neuron specific enolase antibodies, a reference marker for neuronal identity in complex cultures. To further assess the culture responses, a propidium iodide method was used as previously described (Sarafian et al., 2002) to measure the number of dead cells. Propidium iodide becomes fluorescent when binding to the DNA of dead cells. Cultures were treated within the period of culture vulnerability for toxins relevant to HE: between days 11 and 22 after cell plating. The test agents were evaluated with the two assays during a 5 hour test period. For all assays, a 96-well format was used. For the screen, log concentration-effect studies were conducted 10 nM to 100 µM with 5 replications. Cultures were given a complete change of medium prior to the initiation of the treatment period. Testing for neuroprotection from ammonium acetate and ethanol was tested separately and as a combination of 30 mM ethanol and 300 µM ammonium acetate to demonstrate the relevance to HE.

Experimental details for the CFDA assay (Petroski, R. E.; Geller, H. M Selective labeling of embryonic neurons cultures on astrocyte monolayers with 5(6)-carboxyfluorescein diacetate (CFDA). *J. Neurosci. Methods* 1994, 52, 23-32.): Compounds of the disclosure were dissolved in 10 mM in dimethyl sulfoxide and then diluted with Dulbecco's phosphate buffered saline (DPBS; Sigma:D-5780) prior to testing. A compound of the disclosure was added to the hippocampal cultures for a five hour period. Compounds were tested from 10 nM to 100 µM. At the conclusion of the test period, the cultures were tested for the amount of neuronal viability by the CFDA method. For the neuronal viability assay, 1 mg of 5,6-Carboxyfluorescein diacetate (CFDA) dye (Sigma) was dissolved in 100 ml of DPBS (Gibco:D-5780) and kept in the dark until added to the hippocampal cultures. After a complete change of medium on the day of testing, hippocampal test cultures, 100 µl CFDA dye solution was added for 15 min of incubation at 37 degrees in the dark. At the conclusion of the incubation period, the dye was removed from the cultures and washed once with 100 µl of DPBS. After removal of the first wash, a second wash of DPBS was added to the culture and then incubated for 30 min to allow the efflux of dye out of glia in the cultures. At the conclusion of the 30 min efflux period, the culture efflux medium was removed and 100 µl of 0.1% triton-X in water 100 was added to the cultures to before reading at Ex490/Em517 in a CytoFluor fluorimeter. Results were expressed in relative fluorescent units (RFU).

Experimental details for the propidium iodide assay (Sarafian, T. A.; Kouyoumjian, S.; Tashkin, D.; Roth, M. D. Synergistic cytotoxicity of 9-tetrahydrocannabinol and butylated hydroxyanisole, *Tox. Letters,* 2002. 133, 171-179.): Compounds of the disclosure were dissolved in dimethyl sulfoxide to 10 mM. Serial dilutions to the target concentrations were made in Dulbecco's phosphate buffered saline (DPBS; Sigma:D-5780) prior to testing. A compound of the disclosure was added to the hippocampal cultures for a 5 hour test period. Compounds were tested from 10 nM to 100 µM. At the conclusion of the test period, the cultures were tested for the amount of cell death by the propidium iodide method. Propidium iodide (PI) stock solution of 1 mg/ml (1.5 mM) was obtained from Sigma. The PI stock was diluted 1:30 in DPBS for a final working concentration of 50 µM. After removal of the growth medium, 50 µl of the 50 µM PI solution was added to cultures and allowed to incubate in the dark at room temperature for 15 min. The cultures were then assessed for fluorescence intensity at Ex536/Em590 nm in a CytoFluor fluorimeter. Results were expressed in relative fluorescent units and as a % of control values.

Potent neuroprotection is the defining action that characterizes this program's approach to the treatment of neurological disease. In particular, previous studies have indicated that cannabidiol has neuroprotective actions (Nagayama et al., 1999), suggesting that cannabidiol analogs would be of utility in the treatment of neurodegeneration. In addition to the studies of neuroprotection from ethanol and ammonium, additional studies on the efficacy of program compounds in preventing excitotoxicity and oxidative stress related to neurological applications that include epilepsy, Alzheimer's disease and neuropathic pain. Both the amount of glutamate and hydrogen peroxide used in the assays, as well as the time of treatment and duration of the experiment, were designed to be relevant to epilepsy, a probably application for cannabidiol-like compounds. Further, time parameters employed in these studies were empirically determined to be within the limits of reversible toxic events, yet using amounts of glutamate and hydrogen peroxide that were relevant to the disease. In regard to glutamate toxicity, a critical feature was the duration of treatment of the hippocampal neurons. The rational for using a short 5 minute treatment with glutamate was based on the observation of Randall and Thayer (1992). Their study demonstrated that a short-term treatment with glutamate produced a delayed but substantial increase in intracellular calcium that overloaded the neurons and produced cell death. The rationale is that this intense burst of glutamate and resulting calcium overload is relevant to seizures and therefore was important data to capture in the screening assay. The amount of glutamate (30 µM) employed in our screening was based on the basal levels of glutamate observed in microdialysis measurements of hippocampus from epileptogenic patients (Cavus et al., 2008). In regard to hydrogen peroxide, the amount employed (10 µM) was detected in the hippocampus of rats after kainate-induced status epilepticus (Jarrett et al, 2008). To produce neural damage and death with these amounts of glutamate and hydrogen peroxide, the cultures were changed to a medium with significant depletion of antioxidant components in the defined medium supplement B-27 just prior to treatment with the compounds. This was performed to obtain a significant and reproducible toxic signal in the hippocampal neurons and because loss of antioxidant control may be a component of epileptogenesis (Waldbaum and Patel, 2010; Wu et al., 2010).

Experimental Details of the Propidium Iodide Neuroprotection Assay:

Neuroprotection from oxidative stress: Compounds of the disclosure were dissolved to 10 mM in Dulbecco's phosphate buffered saline (DPBS; Sigma: D-5780) prior to testing. To test for neuroprotection from hydrogen peroxide, day 11 hippocampal cultures were given a complete change of medium containing 100 µl of Neurobasal medium with B27 that contained no antioxidants. Twenty four hours after the change in medium, the hydrogen peroxide neuroprotection studies were started. A compound of the disclosure was added to the hippocampal cultures for a 4 hour test period in concentrations that ranged from 1 pM to 300 µM. Concurrent with the treatment of a compound of the disclosure, 10 µM hydrogen peroxide was added for the 4 hour test period. At the conclusion of the test period, the cultures were tested for the amount of cell death by the propidium iodide method. Propidium iodide (PI) stock solution of 1 mg/ml (1.5 mM) was obtained from Sigma. The PI stock was diluted 1:30 in DPBS for a final working concentration of 50 µM. After removal of the growth medium, 50 µl of the 50 µM PI solution was added to cultures and allowed to incubate in the dark at room temperature for 15 min. The cultures were then assessed for fluorescence intensity at Ex536/Em590 nm in a CytoFluor fluorimeter. Results were expressed in relative fluorescent units and EC50's calculated from the dose response of the compounds of the disclosure.

Neuroprotection from Excitotoxicity:

For glutamate neuroprotection studies with the propidium iodide assay, several modifications were made from the method described for the hydrogen peroxide assay. For the glutamate neuroprotection assay, day 19 hippocampal cultures were given a complete change of medium containing 100 µl of Neurobasal medium with B27 that contained no antioxidants. Twenty four hours after the change in medium, the glutamate neuroprotection studies were started. The day 20 cultures were treated for 5 min with 30 µM glutamate dissolved in DPBS. After this short treatment, the medium containing the glutamate was removed from the cultures and fresh medium with antioxidants added. The compound of the disclosure was then added to the hippocampal cultures for a 4 hour test period in concentrations that ranged from 1 pM to 300 µM. At the conclusion of the test period, the cultures were tested for the amount of cell death by the propidium iodide method. Propidium iodide (PI) stock solution of 1 mg/ml (1.5 mM) was obtained from Sigma. The PI stock was diluted 1:30 in DPBS for a final working concentration of 50 µM. After removal of the growth medium, 50 µl of the 50 µM PI solution was added to cultures and allowed to incubate in the dark at room temperature for 15 min. The cultures were then assessed for fluorescence intensity at Ex536/Em590 nm in a CytoFluor fluorimeter. Results were expressed in relative fluorescent units and EC50's calculated from the dose response of the compound of the disclosure.

Experimental Details of the CFDA Neuroprotection Assay:

Neuroprotection from Oxidative Stress:

Compounds of the disclosure were dissolved to 10 mM in Dulbecco's phosphate buffered saline (DPBS; Sigma:D-5780) prior to testing. To test for neuroprotection from hydrogen peroxide, day 11 hippocampal cultures were given a complete change of medium containing 100 µl of Neurobasal medium with B27 that contained no antioxidants. Twenty four hours after the change in medium, the hydrogen peroxide neuroprotection studies were started. The compound of the disclosure was added to the day 12 hippocampal cultures for a 4 hour test period in concentrations that ranged from 1 nM to 300 µM. Concurrent with the treatment of the compound of the disclosure, 10 µM hydrogen peroxide was added for the 4 hour test period. At the conclusion of the test period, the cultures were tested for the amount of neuronal viability by the CFDA method. For the neuronal viability assay, 1 mg of 5,6-Carboxyfluorescein diacetate (CFDA) dye (Sigma) was dissolved in 100 ml of DPBS (Gibco:D-5780) and kept in the dark until added to the hippocampal cultures. After a complete change of medium of day 12 hippocampal test cultures, 100 µl CFDA dye solution was added for 15 min of incubation at 37 degrees in the dark. At the conclusion of the incubation period, the dye was removed from the cultures and washed once with 100 µl of DPBS. After removal of the first wash, a second wash of DPBS was added to the culture and then incubated for 30 min to allow the efflux of dye out of glia in the cultures. At the conclusion of the 30 min efflux period, the culture efflux medium was removed and 100 µl of 0.1% triton-X in water 100 was added to the cultures to before reading at Ex490/Em517 in a CytoFluor fluorimeter. Results were expressed in relative fluorescent units (RFU) and EC50's calculated from the dose response of the compound of the disclosure.

Neuroprotection from Excitotoxicity:

For the glutamate neuroprotection studies with the CFDA assay, several modifications were made from the method described for the hydrogen peroxide assay. For the glutamate neuroprotection assay, day 19 hippocampal cultures were given a complete change of medium containing 100 µl of Neurobasal medium with B27 that contained no antioxidants. Twenty four hours after the change in medium, the glutamate neuroprotection studies were started. The day 20 cultures were treated for 5 min with 30 µM glutamate dissolved in DPBS. After this short treatment, the medium containing the glutamate was removed from the cultures and fresh medium with antioxidants added. The compound of the disclosure was then added to the hippocampal cultures for a 4 hour test period in concentrations that ranged from 1 pM to 300 µM At the conclusion of the test period, the cultures were tested for the amount of neuronal viability by the CFDA method. For the neuronal viability assay, 1 mg of 5,6-Carboxyfluorescein diacetate (CFDA) dye (Sigma) was dissolved in 100 ml of DPBS (Gibco:D-5780) and kept in the dark until added to the hippocampal cultures. After a complete change of medium of day 20 hippocampal test cultures, 100 µl CFDA dye solution was added for 15 min of incubation at 37 degrees in the dark. At the conclusion of the incubation period, the dye was removed from the cultures and washed once with 100 µl of DPBS. After removal of the first wash, a second wash of DPBS was added to the culture and then incubated for 30 min to allow the efflux of dye out of glia in the cultures. At the conclusion of the 30 min efflux period, the culture efflux medium was removed and 100 µl of 0.1% triton-X in water 100 was added to the cultures to before reading at Ex490/Em517 in a CytoFluor fluorimeter. Results were expressed in relative fluorescent units (RFU) and $EC_{50}$'s calculated from the dose response of the compound of the disclosure. Results were expressed in relative fluorescent units and $EC_{50}$'s calculated from the dose response of the compound of the disclosure.

Prevention of Reactive Oxygen Species Increases Associated with Hydrogen Peroxide Day 14 cerebral cortical cultures were utilized to study the increase in reactive oxygen species (ROS) produced after treatment with the oxidative stressor hydrogen peroxide. Prior to treatment, the medium of the cultures was replaced with B27 neural basal medium without antioxidants for 18 hours. To detect the ROS produced by hydrogen peroxide, hippocampal neurons were incubated with the fluorescent dye carboxy-2',7'-difluorodihydrofluorescein diacetate (CD-FFDA) obtained from Molecular Probes (Catalog # C13293). The dye was dissolved in dimethyl sulfoxide at a concentration of 10 mM as a working stock solution. This stock solution of CDFFDA was diluted a 1:1000 in DPBS and added to the cultures for one hour AT 37° C. After the one hour loading of the dye, the cultures were washed two times with DPBS. The cultures loaded with the ROS-sensitive dye were then placed back into B27 medium neural basal medium without antioxidants before treatment with compounds of the disclosure. The cultures were treated with a dose response to compounds of the disclosure and then placed back into the incubator for re-equilibration of the medium (10 minutes). The cultures were then treated with 30 μM hydrogen peroxide for three hours and the fluorescence measured at Ex/Em 485/508. Background fluorescence was subtracted from values obtained from wells without cells.

Seizure-related assays: Previous studies have indicated that cannabidiol can prevent seizures (Consroe and Wolkin, 1977). Another means of evaluating the cannabidiol-related compounds is for their antiseizure effects.

Maximal electroshock test: The most definitive assay for antiseizure activity is the maximal electroshock (WS) test (Swinyard, E. A. Laboratory evaluation of antiepileptic drugs: review of laboratory methods, *Epilepsia*, 1969, 10, 107-119.). This model, which is highly predictive of efficacy in human epilepsy, is utilized to demonstrate antiseizure activity in mice after i.p. administration and in rats after oral administration. With both rodent assays, the duration of action is of high importance as well as the potency of the response.

Results for representative compounds according to the present invention are listed in Table 5.

TABLE 5

Exemplary compounds of the disclosure and their potencies in assays of neuroprotective activity in hippocampal cultures

| Example Number | NP* from Ethanol PI | NP* from Ethanol CFDA $EC_{50}$ | NP** from AmAc PI |
|---|---|---|---|
| 1 | 2 μM | 5 μM | 3 μM |
| 2 | 46 nM | 175 nM | 38 nM |
| 3 | 20 nM | 30 nM | 50 nM |

| Example Number | NP** from AmAc CFDA | NP*** from ethanol + AmAc PI $EC_{50}$ | NP*** from ethanol + AmAc CFDA |
|---|---|---|---|
| 1 | 2 μM | 1.2 μM | 3 μM |
| 2 | 61 nM | 203 nM | 127 nM |
| 3 | 105 nM | 61 nM | 87 nM |

*NP = Neuroprotection from 30 mM ethanol in hippocampal cultures
**NP = Neuroprotection from 300 μM Ammonium Acetate (AmAc) in hippocampal cultures
***NP = Neuroprotection from 30 mM Ethanol plus 300 μM Ammonium Acetate in hippocampal cultures
$EC_{50}$ = the concentration of compound of the disclosure required to produce 50% of the maximal observed protection value (control level).

Full efficacy protection levels are defined as values that were not statistically different from untreated controls.

Pharmacokinetic Profile of Exemplary Compounds of the Disclosure.

Figure 2:
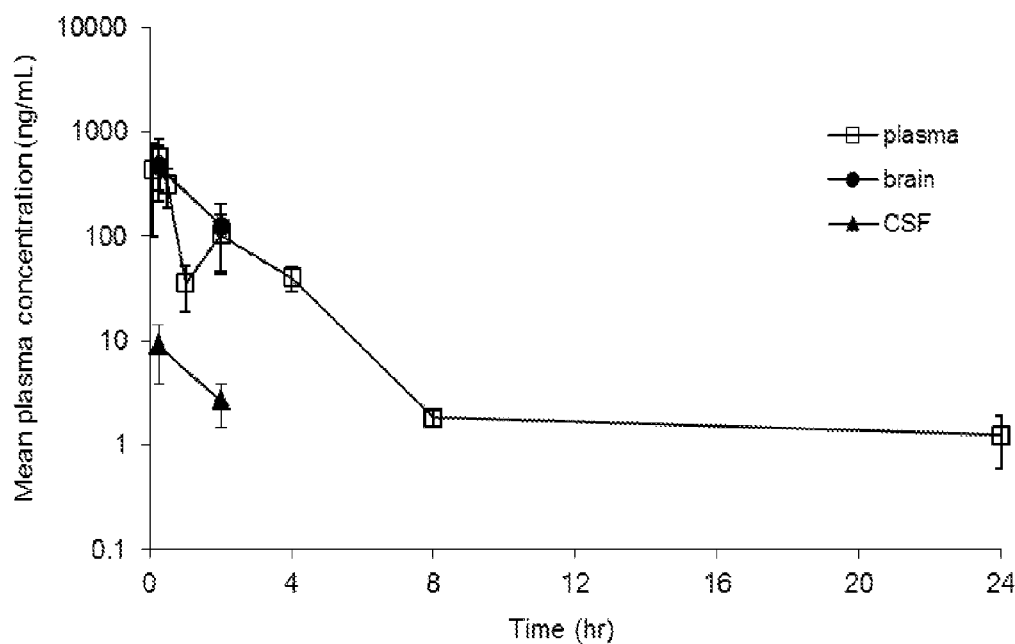
FIG. 2: Mean plasma concentration-time profiles of KLS-13019 (example 2) after single 10 mg/kg PO administration in CD1 mice (N=3/time point).

The pharmacokinetic profile of compounds of the disclosure are determined in CD1 mice by administering IV and PO doses of the compounds of the disclosure to the CD1 mice. Plasma samples are drawn at 0.083, 0.25, 0.5, 1.0, 2.0, 4.0, 8.0, and 24 hours to determine the plasma concentration of the compounds of the disclosure. Brain and CSF samples were collected at 0.25 hours, 2 hours, and 8 hours post dosing. IV doses were prepared as solutions in 5% Dimethylacetamide (DMAC), 5% Solutol HS 15 and 90% Saline at 0.4 mg/mL PO doses were prepared as solutions in 5% Dimethylacetamide (DMAC), 5% Solutol HS 15 and 90% Saline at 1 mg/mL. Experimental results for exemplary compounds of the disclosure are described in tables 6-9 and FIGS. 1 and 2.

TABLE 6

(FIG. 1): PK parameters of KLS-13019 (example 2) after an IV dose of 2 mg/kg in CD1 mice.

| PK parameters | Unit | Value |
|---|---|---|
| CL | L/hr/kg | 4.55 |
| $V_{ss}$ | L/kg | 3.19 |
| $AUC_{last}$ | hr * ng/mL | 431 |
| $AUC_{INF}$ | hr * ng/mL | 440 |
| Terminal $t_{1/2}$ | hr | 3.24 |
| $MRT_{INF}$ | hr | 0.702 |

TABLE 7

(FIG. 1): PK parameters of KLS-13019 (example 2) after a PO dose of 10 mg/kg in CD1 mice.

| PK parameters | Unit | Value |
|---|---|---|
| $T_{max}$ | hr | 0.250 |
| $C_{max}$ | ng/mL | 1089 |
| $AUC_{last}$ | hr * ng/mL | 1436 |
| $AUC_{INF}$ | hr * ng/mL | 1475 |
| Terminal $t_{1/2}$ | hr | 5.36 |
| F | % | 67.1 |

TABLE 8

(FIG. 2): PK parameters of KLS-13019 (example 2) after single 10 mg/kg PO administration in CD1 mice to determine brain and CSF penetration.

| PK parameters | Unit | Value |
|---|---|---|
| $T_{max}$ | hr | 0.250 |
| $C_{max}$ | ng/mL | 565 |
| $AUC_{last}$ | hr * ng/mL | 617 |
| $AUC_{INF}$ | hr * ng/mL | 627 |
| Terminal $t_{1/2}$ | hr | 5.31 |

TABLE 9

(FIG. 2): Individual and mean brain and CSF concentration-time data of KLS-13019 (example 2) after a PO dose of 10 mg/kg in CD1 mice

| | Sampling time (hr) | Concentration (ng/mL) Individual | | | Mean (ng/mL) | SD | CV (%) |
|---|---|---|---|---|---|---|---|
| Brain | 0.25 | 581 | 650 | 177 | 469 | 256 | 54.4 |
| | 2 | 162 | 181 | 34.9 | 126 | 79.4 | 63.1 |
| | 8 | BQL | BQL | BQL | BQL | NA | NA |
| CSF | 0.25 | 13.0 | 10.6 | 3.24 | 8.95 | 5.09 | 56.8 |
| | 2 | 3.60 | 3.00 | 1.35 | 2.65 | 1.17 | 44.0 |
| | 8 | BQL | BQL | BQL | BQL | NA | NA |

TABLE 9-continued (FIG. 2): Individual and mean brain and CSF concentration-time data of KLS-13019 (example 2) after a PO dose of 10 mg/kg in CD1 mice

| | Sampling time (hr) | Concentration (ng/mL) Individual | | | Mean (ng/mL) | SD | CV (%) |
|---|---|---|---|---|---|---|---|
| Brain/ CSF | 0.25 | 44.7 | 61.3 | 54.6 | 53.5 | 8.37 | 15.6 |
| | 2 | 45.0 | 60.3 | 25.9 | 43.7 | 17.3 | 39.5 |
| | 8 | NA | NA | NA | NA | NA | NA |
| Brain/ Plasma (%) | 0.25 | 80.1 | 87.4 | 78.7 | 82.1 | 4.66 | 5.67 |
| | 2 | 115 | 136 | 101 | 117 | 17.6 | 15.0 |
| | 8 | NA | NA | NA | BQL | NA | NA |
| CSF/ Plasma (%) | 0.25 | 1.79 | 1.42 | 1.44 | 1.55 | 0.208 | 13.4 |
| | 2 | 2.55 | 2.26 | 3.91 | 2.91 | 0.884 | 30.4 |
| | 8 | NA | NA | NA | BQL | NA | NA |

What is claimed is:

1. A method for treating or preventing oxidative stress in a neuronal tissue, said method comprising administering to a subject an amount of at least one compound effective to treat or prevent the oxidative stress in the neuronal tissue, wherein the at least one compound is:
   a) 5-(2-(1H-1,2,3-triazol-1-yl)ethyl)-2-((1R,6R)-3-methyl-6-(prop-1-en-2-yl)cyclohex-2-enyl)benzene-1,3-diol;
   b) 1-(3-(3,5-dihydroxy-4-((1R,6R)-3-methyl-6-(prop-1-en-2-yl)cyclohex-2-enyl)benzyl)azetidin-1-yl)ethanone;
   c) ethyl 3-(3,5-dihydroxy-4-((1R,6R)-3-methyl-6-(prop-1-n-2-yl)cyclohex-2-enyl)benzyl) azetidine-1-carboxylate; or a pharmaceutically acceptable salt thereof.

2. The method of claim 1, wherein the at least one compound is isotopically labeled with 1 to 10 deuterium atoms.

3. The method of claim 1, wherein the at least one compound is administered in a composition further comprising at least one excipient.

4. The method of claim 1, wherein the at least one compound is 1-(3-(3,5-dihydroxy-4-((1R,6R)-3-methyl-6-(prop-1-en-2-yl)cyclohex-2-enyl)benzyl)azetidin-1-yl)ethanone or a pharmaceutically acceptable salt thereof.

5. The method of claim 1, wherein the subject is a human.

6. The method of claim 4, wherein the treating or preventing the oxidative stress treats or prevents at least one condition or disease associated with the oxidative stress, said at least one condition or disease being selected from the group consisting of hepatic encephalopathy, epilepsy, neuropathic pain, traumatic head injury, stroke, Chronic Traumatic Encephalopathy (CTE), Post Cardiac Arrest Hypoxic Ischemic Encephalopathy, Epileptic Encephalopathy, Parkinson's disease, Alzheimer's, Huntington's disease and amyotrophic lateral sclerosis (ALS).

* * * * *